(12) United States Patent
Hutcheson et al.

(10) Patent No.: US 8,795,989 B2
(45) Date of Patent: Aug. 5, 2014

(54) ENZYMIC PRODUCTION OF NEOAGAROBIOSE

(75) Inventors: Steven W. Hutcheson, Columbia, MD (US); Ronald M. Weiner, Potomac, MD (US); Nathan A. Ekborg, Beverly, MA (US)

(73) Assignee: University of Maryland, College Park, MD (US)

( * ) Notice: Subject to any disclaimer, the term of this patent is extended or adjusted under 35 U.S.C. 154(b) by 979 days.

(21) Appl. No.: 12/112,912

(22) Filed: Apr. 30, 2008

(65) Prior Publication Data

US 2009/0053776 A1   Feb. 26, 2009

Related U.S. Application Data

(60) Provisional application No. 60/914,791, filed on Apr. 30, 2007.

(51) Int. Cl.
*C12P 19/12* (2006.01)
*C12N 9/38* (2006.01)
*C12N 11/00* (2006.01)

(52) U.S. Cl.
USPC .......................................... 435/100; 435/207

(58) Field of Classification Search
CPC .............................. C12P 19/12; C12N 9/2468
USPC .................................................. 435/100, 207
See application file for complete search history.

(56) References Cited

PUBLICATIONS

Chica et al. Curr Opin Biotechnol. Aug. 2005; 16(4):378-84.*
Witkowski et al. Biochemistry. Sep. 7, 1999; 38(36): 11643-50.*
Seffernick et al. (J Bacteriol. Apr. 2001; 183 (8): 2405-10.*
Ekborg et al. Environ. Microbiol. 2006, pp. 3396-3405.*
Copeland et all. Accession No. Q21HB4, Apr. 18, 2006.*
Theoritical Molecular weight of amino acid sequence of SEQ Id No. 9.*
Allouch, J., W. Halbert, B. Henrissat, and M. Czjzek. 2004. Parallel substrate binding sites in a beta-agarase suggest a novel mode of action on double-helical agarose. Structure. 12:623-32.
Allouch, J., M. Jam, W. Helbert, T. Barbeyron, B. Kloareg, B. Henrissat, and M. Czjzek. 2003. The three-dimensional structures of two beta-agarases. J Biol Chem. 278:47171-80.
Andrykovitch, G., and I. Marx. 1988. Isolation of a New Polysaccharide-Digesting Bacterium from a Salt Marsh. Appl Environ Microbiol. 54:1061-1062.
Aoki, T., T. Araki, and M. Kitamikado. 1990. Purification and characterization of a novel beta-agarase from *Vibrio* sp. AP-2. Eur J Biochem. 187:461-5.
Araki, T., M. Hayakawa, Z. Lu, S. Karita, and T. Morishita. 1998. Purification and characterization of agarases from a marine bacterium, *Vibrio* sp. PO-303. J Mar Biotechnol. 6:260-265.

Barbeyron, T., S. L'Haridon, E. Corre, B. Kloareg, and P. Potin. 2001. *Zobellia galactanovorans* gen. nov., sp. nov., a marine species of Flavobacteriaceae isolated from a red alga, and classification of. Int J Syst Evol Microbiol. 51:985-97.
Belas, R. 1989. Sequence analysis of the agrA gene encoding beta-agarase from *Pseudomonas atlantica*. J Bacteriol. 171:602-5.
Bendtsen, J.D., H. Nielsen, G. von Heijne, and S. Brunak. 2004. Improved prediction of signal peptides: SignalP 3.0. J Mol Biol. 340:783-95.
d'Enfert, C., I. Reyss, C. Wandersman, and A.P. Pugsley. 1989. Protein secretion by gram-negative bacteria. Characterization of two membrane proteins required for pullulanase secretion by *Escherichia coli* K-12. J Biol Chem. 264:17462-8.
Edgar, R.C. 2004. Muscle: multiple sequence alignment with high accuracy and high throughput. Nucleic Acids Res. 32:1792-7.
Ekborg, N.A., J.M. Gonzalez, M.B. Howard, L.E. Taylor, S.W. Hutcheson, and R.M. Weiner. 2005. *Saccharophagus degradans* gen. nov., sp. nov., a versatile marine degrader of complex polysaccharides. Int J Syst Evol Microbiol. 55:1545-9.
Eng, JK, McCormack AL, and Yates, JR. An approach to correlate tandem mass spectral data of peptides with amino acid sequences in a protein database. Journal of the American Society for Mass Spectrometry, 5, 976-989, 1994.
Ensor, L., S. Stosz, and R. Weiner. 1999. Expression of multiple complex polysaccharide-degrading enzyme systems by marine bacterium strain 2-40. J Ind Microbiol Biotechnol. 23:123-126.
Finn, R.D., J. Mistry, B. Schuster-Bockler, S. Griffiths-Jones, V. Hollich, T. Lassmann, S. Moxon, M. Marshall, A. Khanna, R. Durbin, S.R. Eddy, E.L. Sonnhammer, and A. Bateman. 2006. Pfam: clans, web tools and services. Nucleic Acids Res. 34:D247-51.
Gasteiger, E., C. Hoogland, A. Gattiker, S. Duvaud, M.R. Wilkins, R.D. Appel, and A. Bairoch. 2005. Protein Identification and Analysis Tools on the ExPASy Server. In The Proteomics Protocols Handbook. vol. J. Walker, editor Humana Press, 571-607.
Gonzalez, J.M., and R.M. Weiner. 2000. Phylogenetic characterization of marine bacterium strain 2-40, a degrader of complex polysaccharides. Int J Syst Evol Microbiol. 50 Pt 2:831-4.
Hosoda, A., M. Sakai, and S. Kanazawa. 2003. Isolation and characterization of agar-degrading *Paenibacillus* spp. associated with the rhizosphere of spinach. Blosci Biotechnol Biochem. 67:1048-55.
Howard, M.B., N. A. Ekborg, L.E. Taylor, R.M. Weiner, and S.W. Hutcheson. 2003. Genomic analysis and initial characterization of the chitinolytic system of Microbulbifer degradans strain 2-40. J Bacteriol. 185:3352-60.
Juncosa, M., J. Pons, T. Dot, E. Querol, and A. Planes. 1994. Identification of active site carboxylic residues in *Bacillus licheniformis* 1,3-1,4-beta-D-glucan 4-glucanohydrolase by site-directed mutagenesis. J Biol Chem. 269:14530-5.
Kang, N.Y., Y.L. Choi, Y.S. Cho, B.K. Kim, B.S. Jeon, J.Y. Cha, C.H. Kim, and Y.C. Lee. 2003. Cloning, expression and characterization of a beta-agarase gene from a marine bacterium, *Pseudomonas* sp. SK38. Biotechnol Lett. 25:1165-70.
Kobayashi, R., M. Takisada, T. Suzuki, K. Kirimura, and S. Usami. 1997. Neoagarobiose as a novel moisturizer with whitening effect. Biosci Biotechnol Biochem. 61:162-3.

(Continued)

*Primary Examiner* — Tekchand Saidha
*Assistant Examiner* — Younus Meah
(74) *Attorney, Agent, or Firm* — Dykema Gossett PLLC

(57) ABSTRACT

The present invention is directed to methods and systems of producing neoagarobiose, useful in whitening melanoma cells and in cosmetics, using polypeptides having neoagarobiosebiohydralase activity, including Aga86E from *Saccharophagus degradans*. The reaction can be enhanced by including other agarases, including Aga16B, also from *S. degradans*.

15 Claims, 15 Drawing Sheets

(56) References Cited

PUBLICATIONS

Letunic, I., R.R. Copley, B. Pils, S. Pinkert, J. Schultz, and P. Bork. 2006. SMART 5: domains in the context of genomes and networks. Nucleic Acids Res. 34:D257-60.

Metzgar, D., J.M. Bacher, V. Pezo, J. Reader, V. Doring, P. Schimmel, P. Marliere, and V. de Crecy-Lagard. 2004. *Acinetobacter* sp. ADP1: an ideal model organism for genetic analysis and genome engineering. Nucleic Acids Res. 32:5780-90.

Morrice, L.M., M.W. McLean, W.F. Long, and F.B. Williamson. 1983a. Beta-agarases I and II from *Pseudomonas atlantica*. Substrate specificities. Eur J Biochem. 137:149-54.

Morrice, L.M., M.W. McLean, F.B. Williamson, and W.F. Long. 1983b. beta-agarases I and II from *Pseudomonas atlantica*. Purifications and some properties. Eur J Biochem. 135:553-8.

Murphy, K.C. 1998. Use of *bacteriophage lambda* recombination functions to promote gene replacement in *Escherichia coli*. J Bacteriol. 180:2063-71.

Ohta, Y., Y. Hatada, S. Ito, and K. Horikoshi. 2005. High-level expression of a neoagarobiose-producing beta-agarase gene from *Agarivorans* sp. JAMB-A11 in *Bacillus subtilis* and enzymic properties of the recombinant enzyme. Biotechnol Appl Biochem. 41:183-91.

Ohta, Y., Y. Nogi, M. Miyazaki, Z. Li, Y. Hatada, S. Ito, and K. Horikoshi. 2004b. Enzymatic properties and nucleotide and amino acid sequences of a thermostable beta-agarase from the novel marine isolate, JAMB-A94. Biosci Biotechnol Biochem. 68:1073-81.

Page, R.D. 1996. TreeView: an application to display phylogenetic trees on personal computers. Comput Appl Biosci. 12:357-8.

Perkins, D.N., D.J. Pappin, D.M. Creasy, and J.S. Cottrell. 1999. Probability-based protein identification by searching sequence databases using mass spectrometry data. Electrophoresis. 20:3551-67.

Plotkin, J.B., H. Robins, and A.J. Levine. 2004. Tissue-specific codon usage and the expression of human genes. Proc Natl Acad Sci U S A. 101:12588-91.

Potin, P., C. Richard, C. Rochas, and B. Kloareg. 1993. Purification and characterization of the alpha-agarase from *Alteromonas agariyticus* (Cataldi) comb. nov., strain GJ1B. Eur J Biochem. 214:599-607.

Schroeder, D.C., M.A. Jaffer, and V.E. Coyne. 2003. Investigation of the role of a beta(1-4) agarase produced by *Pseudoalteromonas gracilis* B9 in eliciting disease symptoms in the red alga *Gracilaria gracilis*. Microbiology. 149:2919-29.

Schultz, J., F. Milpetz, P. Bork, and C.P. Ponting. 1998. SMART, a simple modular architecture research tool: identification of signaling domains. Proc Natl Acad Sci U S A. 95:5857-64.

Sugano, Y., H. Kodama, I. Terada, Y. Yamazaki, and M. Noma. 1994a. Purification and characterization of a novel enzyme, alpha-neoagarooligosaccharide hydrolase (alpha-NAOS hydrolase), from a marine bacterium, *Vibrio* sp. strain JT0107. J Bacteriol. 176:6812-8.

Sugano, Y., T. Matsumoto, H. Kodama, and M. Noma. 1993. Cloning and sequencing of agaA, a unique agarase 0107 gene from a marine bacterium, *Vibrio* sp. strain JT0107. Appl Environ Microbiol. 59:3750-6.

Sugano, Y., T. Matsumoto, and M. Noma. 1994b. Sequence analysis of the agaB gene encoding a new beta-agarase from *Vibrio* sp. strain JT0107. Biochim Biophys Acta. 1216:105-8.

Swartz, M.N., and N. Gordon. 1959. Agarase from an agar-digesting bacterium. J Bacteriol. 77:403-9.

Thompson, J.D., T.J. Gibson, F. Plewniak, F. Jeanmougin, and D.G. Higgins. 1997. The CLUSTAL_X windows interface: flexible strategies for multiple sequence alignment aided by quality analysis tools. Nucleic Acids Res, 25:4876-82.

Thompson, J.D., D.G. Higgins, and T.J. Gibson. 1994. Clustal W: improving the sensitivity of progressive multiple sequence alignment through sequence weighting, position-specific gap penalties and weight matrix choice. Nucleic Acids Res. 22:4673-80.

Turvey, J.R., and J. Christison. 1967. The hydrolysis of algal galactans by enzymes from a *Cytophaga* species. Biochem J. 105:311-6.

Uetanabaro, A.P., C. Wahrenburg, W. Hunger, R. Pukall, C. Sproer, E. Stackebrandt, V.P. de Canhos, D. Claus, and D. Fritze. 2003. *Paenibacillus agarexedens* sp. nov., nom. rev., and *Paenibacillus agaridevorans* sp. nov. Int J Syst Evol Microbiol. 53:1051-7.

Wilkins, M.R., I. Lindskog, E. Gasteiger, A. Bairoch, J.C. Sanchez, D.F. Hochstrasser, and R.D. Appel. 1997. Detailed peptide characterization using PEPTIDEMASS—a World-Wide-Web-accessible tool. Electrophoresis. 18:403-8.

Xu, Q., M. Morrison, K.E. Nelson, E.A. Bayer, N. Atamna, and R. Lamed. 2004. A novel family of carbohydrate-binding modules identified with *Ruminococcus albus* proteins. FEBS Lett. 566:11-6.

Zhong, Z., A. Toukdarian, D. Helinski, V. Knauf, S. Sykes, J.E. Wilkinson, C. O'Bryne, T. Shea, C. DeLoughery, and R. Caspi. 2001. Sequence analysis of a 101-kilobase plasmid required for agar degradation by a Microscilla Isolate. Appl Environ Microbiol. 67:5771-9.

Van der Meulen, H.J., and W. Harder. 1975. Production and characterization of the agarase of Cytophaga flevensis. Antonie Van Leeuwenhoek. 41:431-47.

Whitehead, L.A., S.K. Stosz, and R.M. Weiner. 2001. Characterization of the agarase system of a multiple carbohydrate degrading marine bacterium. Cytobios. 106 Suppl 1:99-117.

Bibb, M.J., G.H. Jones, R. Joseph, M.J. Buttner, and J.M. Ward. 1987. The agarase gene (dag A) of *Streptomyces coelicolor* A3(2): affinity purification and characterization of the cloned gene product. J Gen Microbiol. 133:2089-96.

Altschul, S.F., W. Gish, W. Miller, E.W. Myers, and D.J. Lipman. 1990. Basic local alignment search tool. J Mol Biol. 215:403-10.

Duckworth, M., and W. Yaphe. 1970. Thin-layer chromatographic analysis of enzymic hydrolysates of agar. J Chromatogr. 49:482-7.

Coutinho, P., and B. Henrissat. 1999. Carbohydrate-active enzymes: an integrated database approach. In Recent advances in carbohydrate engineering. vol. H. Gilbert, G. Davies, B. Henrissat, and b. Swensson, editors. The Royal Society of Chemistry, Cambridges. 3-12.

Kelly, S., V. Coyne, D. Sledjeski, C. Fuqua, and R. Weiner. 1990. Identification of a tyrosinase from a periphytic marine bacterium. FEMS Microbiol. Lett. 67:275-280.

Shieh, W.Y., and W.D. Jean. 1998. Alterococcus agarolyticus, gen. nov., sp.nov., a halophilic thermophilic bacterium capable of agar degradation. Can J Microbiol. 44:637-45.

Coutinho, Pedro M., Henrissat, Bernard. The modular structure of cellulases and other carbohydrate-active enzymes: an integrated database approach. 1999. Genetics, Biochemistry and Ecology of Cellulose Degradation. 15-23.

Ha, Jeong-Chul, Kim, Gu-Taek, Kim, Sung-Koo, Oh, Tae-Kwang, Yu, Ju-Hyun, Kong, In-Soo. 1997. Beta-Agarase from *Pseudomonas* sp. W7: purification of the recombinant enzyme from *Escherichia coli* and the effects of salt on its activity. Biotechnology and Applied Biochemistry. 1:1-6.

* cited by examiner

| | | |
|---|---|---|
| Aeromonas β-Aga | 1 ------------------------SAGSGKTWQLQT-MSDQFNYQAGTSNKPAAFT-NRW | SEQ ID NO:14 |
| Pa. atlantica DagA | 1 ----------------WSSFSIPAQAGAGKSWQLQS-MSEFNYIAQPNNKPAAFN-NRW | SEQ ID NO:15 |
| Zobellia AgaA | 1 --------------------------GMTWQLQDNMSESFNYTSSEGNRPTAFT-SKW | SEQ ID NO:16 |
| Microb. JAMB-A7 | 1 ----------------WDGTPVPADAGPGNTWFLHP-ISDDFNYSAPASGKSATFF-ERW | SEQ ID NO:17 |
| S. degradans AgaB | 1 ----------------------------TWELQS-LSDDFNYAAPANGKRTIFY-SRW | SEQ ID NO:18 |
| Pm. ND137 agarase | 1 ----------------DGLAVPADAGDGKTWQLQSSLSDDFSTSAPAEGKSQAFY-ERW | SEQ ID NO:19 |
| Microb. JAMB-A94 | 1 ----------------DGVPVPANPESGKTWFLHP-ISDDFNYEAPAAGKSIRFY-ERW | SEQ ID NO:20 |
| Pm. ND137 AagA | 1 --------------------PVPANAGNGKVWELQA-MSDDFNYSSLDNYHEFT-RRW | SEQ ID NO:21 |
| Zobellia AgaB | 1 ----------LVEEVDWKDIPVPADAGPNMKWEFQE-ISENPEYEAPADNKGSEFL-EKW | SEQ ID NO:22 |
| Micros. MS116 | 1 TLLITWIAFLGAKAQDWSGIPVPASAGQGKTWQLQSAASDDFNYIFNETSQLINFGSNKW | SEQ ID NO:23 |
| Pa. CY24 AgaA | 1 ------------------------------------------SGKPSSFT-SKW | SEQ ID NO:24 |
| S.c. A3 DagA | 1 ----------AADLEWEQYPVPAAPGGNRSWQLLPSHSDDFNYI----GKPQTFR-GRW | SEQ ID NO:25 |

| | | |
|---|---|---|
| Aeromonas β-Aga | 35 NASYINWLGPGDTEFSSGHEVTTGGALGLQATEK-----AGTNKVLSGIVSSKAIFTYP |
| Pa. atlantica DagA | 43 NASYINWLGPGDTEFSAGHSVTTGGALGLQATEK-----AGTNKVLSGITSSKAIFTYP |
| Zobellia AgaA | 32 KPSYINWTGPGSIEFNAAQAWTNSSCLAIQAQP-----AGNGKSYNGIITSKNKIQYP |
| Microb. JAMB-A7 | 43 SEGFINPWLGPGETEFNPSTDSQNLVIKASRK-----AGITKIHAGAIHSNESVTYP |
| S. degradans AgaB | 29 SEGFINAWLGPGQTEFYGPNASVEGGSLHIKATRK-----PGITQIYTGAIHSNESFTYP |
| Pm. ND137 | 43 SEGFINWQGPGLIDYHNPNSRVENGELMITATRK-----AGTNEVYTGAIHTNESVQYP |
| Microb. JAMB-A94 | 42 KEGFINPWTGPGLTEWHPHYSAVVSGGKLAITSGRK-----PGTNQWYLGSITSKAPLTYP |
| Pm. ND137 AagA | 39 HEGFINPWTGPGLTEMIDGHAYMTDGNLGIAATRK-----PGTDKVRAGSITSECIFTYP |
| Zobellia AgaB | 49 DDFYHNAWAGPGLTEMKREDSIYADGELKMWATRK-----PGSDKINMGCITSKIDRWYP |
| Micros. MS116 | 61 YNFYSNGWDGPGTYMQYNEVSGGKLVLPASKNPSTTKMGVPGVNAGCITSNNRVKYP |
| Pa. CY24 agaA | 12 KDAYFHNWTGPGLTYNSSDESWVGDRNLIISASRK-----QGTNQVNAGVMTSKTKVKYP |
| S.c. A3 DagA | 45 LDQHKDGWSGPANSLYSARHSWVADRNLIVEGRK-----APDGRMYCGYMTSKTPVEYP |

FIG.2

| | | |
|---|---|---|
| Aeromonas β-Aga | 90 | LYLEAMVKPSNNTMANAVWMLSSDSTQEIDAMESYGSDRVG-----QEWFDQRMHVSHHV |
| Pa. atlantica DagA | 98 | LYLEAMVKPTNNTMANAVWMLSADSTQEIDAMESYGSDRIG-----QEWFDQRMHVSHHI |
| Zobellia AgaA | 86 | VMMEIKAKIMDQVLANAFWTLTDDETQEIDIMEGYGSDRG------GTWFAQRMHLSHHT |
| Microb. JAMB-A7 | 98 | LYMEARVQVTNLTMANAFWLLSSDSTQEIDVLESYGSDRPS-----ETWFDERLHLSHHV |
| S. degradans AgaB | 84 | LYLEARTKITNLTLANAFWLLSSDSTEEIDVLESYGSDRAT-----ETWFDERLHLSHHV |
| Pm. ND137 | 98 | VMIETSSKIMDQVLANAVWMLSSDSTQEIDIVEAYGSSRAD-----QTWFAERMHLAHHV |
| Microb. JAMB-A94 | 97 | VMMEARAKLSNMVLASDFWFLSADSTEEIDVLEAYGSDRPG-----QEWYAERLHLSHHV |
| Pm. ND137 AagA | 94 | LYMETKAKISKLVLASDVWLLSADSTQEIDVLEAYGSDRAG-----QEWFAERIHLSHHV |
| Zobellia AgaB | 104 | VMIEARAKVMNSTLASDVWLLSADDTQEIDILEAYGADYSESAGKDHSYFSKKVHISHHV |
| Micros. MS116 | 121 | VFVEASVSVANIALASDVWLLSPDDTQEIDIIECYGGAGSN-----NAYFAQFIHLSHHS |
| Pa. CY24 AgaA | 67 | IFLEANIKVSNLELSSNFWLLSENDQREIDVLEVYGGARQD-------WFAKNMSTNFHV |
| S.c. A3 DagA | 99 | LYTEVLMRVSGLKLSSNFWLLSRDDVNEIDVIECYGNESLHG---------KIMNTAYHI |

FIG.2
(CONTINUED)

```
Aeromonas β-aga     145  FIREPFQDYQPKDAGAWVY-------NSGETYRNKFR---------RYGVHMKDAWNLDY
Pa. atlantica DagA  153  FIRDPFQDYQPKDAGSWVY-------NNGETYRNKFR---------RYGVHMKDAWNLDY
Zobellia AgaA       140  PIRNPFTDYQPMGDATWYY-------NGGTPWRSAYS---------RYGCYWRDPSTLEY
Microb. JAMB-A7     153  FIREPFQDYQPKDGSWYP----N-PNGGTWRDQMI---------RIGIYWVDPWTLEY
S. degradans AgaB   139  FIRQPFQDYQPKDAGSWYP----N-PDGGTWRDQPF---------RIGVYWIDPWTLEY
Pm. ND137           153  FIRDPFQDYQPKDAGAWY-------ADGRLWFEQYS---------RVGVYWRDPWHLEY
Microb. JAMB-A94    152  FIRDPFQDYQPTDAGSWYA----D-GKGTKWRDAPF---------RVGVYWRDPWHLEY
Pm. ND137 AagA      149  FIRDPFQDYQPTDAGSWYT----D-GQGTVWSDDFF---------RIGVHMKDPWNLDY
Zobellia AgaB       164  FIRDPFQDYQPKDAGSWF-------EDGTVWNKEFF---------RFGVYWRDPWHLEY
Micros. MS116       176  PMRNPFQDYQPRDLNSWG----K-SGVSSWCDYCWNNGNRK-YVRVGVNWVGKHPEY
Pa. CY24 AgaA       120  FFRNNDNSISSDFNDQTHN----TPTWGNYKREGFR---------RFGVYWKSPTEYF
S.c. A3 DagA        150  PQRNPFTELARSQKGYFADGSYGYNGETCQVFSDGAGQPLLRNGPHRYGVHMISATEFCP
```

```
Aeromonas β-Aga     189  YIDGVLVRSVSGP----------------------------------  SEQ ID NO:14
Pa. atlantica DagA  197  YIDGVLVRSVSGP----------------------------------  SEQ ID NO:15
Zobellia AgaA       184  YIDGVKVRTVIR-----------------------------------  SEQ ID NO:16
Microb. JAMB-A7     198  WVNGEHVRTVIGP----------------------------------  SEQ ID NO:17
S. degradans AgaB   184  WVNGELVRTVSGP----------------------------------  SEQ ID NO:18
Pseudom. ND137      196  YIDGQLVRTVSGV----------------------------------  SEQ ID NO:19
Microb. JAMB-A94    197  YMDGVLVRTVSGQ----------------------------------  SEQ ID NO:20
Pm. ND137 AagA      194  YIDGQLVRSVSGP----------------------------------  SEQ ID NO:21
Zobellia AgaB       207  YIDGVLVRTVSGK----------------------------------  SEQ ID NO:22
Micros. MS116       229  YIDGELVRVLRDKAFATKVNGTWYYTYPTMTNGSLDFSGGYQSVVQYATGSSYSFSTLQA  SEQ ID NO:23
Pa. CY24 AgaA       166  YINGQKTTKGAWS----------------------------------  SEQ ID NO:24
S.c. A3 DagA        210  YFNGRLVRELNRS----------------------------------  SEQ ID NO:25
```

FIG.2
(CONTINUED)

```
V. JT0107 AgaA      1 ---------SESALRQSMPTELPS--DYMNENYG---PVHSGFVSQGAVSPYANNLITK  SEQ ID NO:27
Agar. JAMB-A11      1 -----------SALRQSMPTELPS--DYMNENYG---PVHSGFVSQGAVSPYANNLITK  SEQ ID NO:28
Uncult. AguC        1 -KSAWSSFHISSQLRADMPTWLPSYNEAAGANYGYRRSVHSGSLKGETFSPYRANLARK  SEQ ID NO:29
S. degradans_AgaA   1 -DAALPTFHISSPLRAEMPTWLPQIDEPLGLNEGYRREVHIGALFGETFSPYRANLQRK  SEQ ID NO:30
S. degradans_AgaD   1 -EKSPAIFHLASPTRAAMPNWLPDYHPLANHYNVRRSAHSGFLKGEAVSPYSANLERK  SEQ ID NO:31
S.c. A3 hyd.        1 -KSALPIRTKMSETRADLPCKLPKYRTRACEGRGYAPDTLAGHVAQGETFSPYKANVARK  SEQ ID NO:32
V. JT0107 AgaB      1 -KDKRSGKEVASEVRRSMPTWLPEDDVLAENYDYANWVHSGALKGGEVFSPYGANLQRK  SEQ ID NO:33
Azoto. AcOP         1 YGQSCKPPVEQAAEPERVLPAALMEEEPDNVQMAP----EGGTPAPGQPAPAKQPTAAPP  SEQ ID NO:34

V. JT0107 AgaA     47 HASED---MWR---DITVKRMKDWGFNTLGNWTDPALYANGDMPYVANGWSTSGADRLPV
Agar. JAMB-A11     45 HASED---MWR---DITVKRMKDWGFNTLGNWTDPALYANGDMPYVANGWSTSGADRLPV
Uncult. AguC       60 YATQDEETLMQYWRDATIKRMHNWGFISFGNWVDASFYQMNNLLPYFANGWIEG---DFKI
S. degradans_AgaA  60 YGISDEAALMSKWETTVNRMLSWGFISFGNWTDPAYYQMDRIPYFANGWIEG---NFKI
S. degradans_AgaD  60 YGELYPGSYLDKWREVTVDRMLNWGFTSLGNWTDPAYYDNNRIPFFANGWMEG---DFKI
S.c. A3 hyd.       60 YPCSN---YSSWRDNTVDRMLSWGFISFGNWTDPEMIDNDRIPYFAHGWIKG---DFKI
V. JT0107 AgaB     60 YCGIFS-EAEKVKSIHTIDRMKDWGFTTLGNWADPMYDNKKVAMVANGWIPG---DHAR
Azoto. AcOP        57 CVVQFFD--ALRWEGHTLDRLQAWGENILGNWSDLSLGAMERIPYTIPLLERG---DYAT V. JT0107 AgaA    101 KQIGSGYWGPLPDMPDANPATNAATMAAEIKALMEGNEEYLVGIEVDNEMSWGNVTDVEG
Agar. JAMB-A11     99 KQIGSGYWGPLPDMPDANPATNAATMAAEIKALMEGNEEYLVGIEVDNEMSWGNVTDVEG
Uncult. AguC      117 VNSGNDYWGAMPDPFDPVPTQRTDKVIAQIANEVK-NNPWCVGVEIDNEKSWG----SMG
S. degradans_AgaA 117 VSSGNDYMSPLPDPFDPLPKERAYHIAEQIGREVK-MNPWCVGVEIDNEKSWG----QEG
S. degradans_AgaD 117 VSSGADFNGAMPLMPDPEPKVRAMETARVWSELIK-NSPWCVGVEIDNEKSPG----RPD
S.c. A3 hyd.      114 VSIGIDYWGPMPDPFDPAPSDAARTARAVADEVA-DSPLAIGVSMDNEISWG----NAG
V. JT0107 AgaB    116 LPIKNDYWGPLHDPFDPEPVNSVKAMTKKLMTEVDKNDPWMGVEVDNEISWG----NTK
```

FIG.3

```
Azoto. AcOP      112  SIGHDNWGGMPDPFDPRFAMAVERAIAIATRDHR-NDPWVIGYFADNELSWA----APG V. JT0107 AgaA   161  SRYAQTLAVFNTDGTDATTSPAKNSFIWFLENQRYTGGIADLNAAWGTDYASWDATSP--
Agar. JAMB-A11   159  SRYAQTLAVFNTDGTDATTSPAKNSFIWFLENQRYTGGIADLNAAWGTDYASWDAMRP--
Uncult. AguC     172  TPSLQYGLVINGLKKANDSPLKQEFIRHLKNKYQN--IENLNTAWDLKNTSWAQLSQ--
S. degradans_AgaA 172 AVQTQYGLVINTLSPAAEDSPTKAQFVMLMQQKYGA--ITELNRAWNVELNSWQEFAN--
S. degradans_AgaD 172 SDKAQYGIPIHTLGRPSEGVPTRQAFSKLLKAKYKT--IAALNNAWGLKLSSWAEFDLG-
S.c. A3 hyd.     169  SFSTRYGWVIDIMSRDAAESPTKSAFSDELEEKYGI--IDALNAAWQTTIVPSWEALRSG-
V. JT0107 AgaB   172  NDANHYGLVVNALSYDMKKSPAKAAFTEHLKEKYWA--IEDLNTSWGVKVASWAEFEKS-
Azoto. AcOP      167  TDPKARYALAYGTLRQTTIDMPAKRAFLKLLRDRYRN--QQGLSAAWGIELPAWELMEDPG
```

FIG. 3
(CONTINUED)

```
V. JT0107 AgaA        219  ---AQELAYVAGMEADMQFLAWQFAFQYFNTVNTALKAELPNHLYLGSRFADWGRTPDVV
Agar. JAMB-A11        217  ---AQELAYVAGMEADMQFLAWQFAFQYFNTVNTALKAELPNHLYLGSRFADWGRTPDVV
Uncult. AguC          228  --PVELVLFNEKMLGDFSELLYLYADAYFSRVNQAFRKHMPNHLYMGPRFAHWAMTPEVL
S. degradans_AgaA     228  --GVVLTQFSDAVVADLSVMLEHYAGQYFKIVREAVKHYLPNHMYLGARFADWGMTPEIR
S. degradans_AgaD     229  -VDVKALPVTDTLRADYSMLLSAYADQYFKVMHGAVEHYMPNHLYLGARFPDWGMPMEVV
S.c. A3 hyd.          226  --SADLGSDETAKESDYSALMTLYATQYFKTVDAELDKVMPDHLYAGSRFASWGRTPEVV
V. JT0107 AgaB        229  --FDHRSRLSKNMKKDYAEMLEMLSAKYFSTVRAELKKVLPNHLYGAPPFADWGVTPEIA
Azoto. AcOP           225  FEAPLPSPEHPAIEEDLQRFQQLFADTYFKTIAESLKWHADHLLLGCRFAIS--TPEAV V. JT0107 AgaA        276  SAAAAVVDVMSYNIYKDSIAAADWDADALSQIEAIDKPVIIGEFHFGALDSGSFAEGVVN
Agar. JAMB-A11        274  SAAAAVVDVMSYNIYKDSIAAADWDADALSQIEAIDKPVIIGEFHFGALDSGSFAEGVVN
Uncult. AguC          286  KAAAKYTDVMSYNYYREGIDQP-----YWDFLAELDKPSIIGEFHNGALDSGLLNPGLIH
S. degradans_AgaA     286  RSAAKYADVMSYNYYKEGVSNK-----FWHFLEELDKPSIIGEFHNGALDSGLLNPGVVH
S. degradans_AgaD     288  KAAAKYADVMSYNSYKEGLPKQ-----KWAFLAELDKPSIIGEFHIGAMDHCSYHPGLIH
S.c. A3 hyd.          284  EAASKYVDIMSYNEYREGLHPS-----EWAFLEELDKPSLIGEFHMGTTTIGQPHPGLMS
V. JT0107 AgaB        287  KGAAPYVDVMSYNLYARDINSKG----DWSKLAELDKPSIIGEFHFGSIDSGLFHGGIVS
Azoto. AcOP           283  EACAKYCDVLSFNFYTREPQHG-----YDFEALRKLDKPMLVSEFHFGSRDRGPFWGVAE V. JT0107 AgaA        336  ATSQQDRADKMVSFYESVNAHKNFVGAHWFQYIDSPLTGRAMDGENYNVGFVSNTDTPYT
Agar. JAMB-A11        334  ATSQQDRADKMVSFYESVNAHKNFVGAHWFQYIDSPLTGRAMDGENYNVGFVSNTDTPYT
Uncult. AguC          341  AESQFDRGEKYKSYLNSVIDNPYFVGAHWFQYIDSPLTGRAYDGENYNVGFVSVADIPYP
S. degradans_AgaA     341  ASSQADRGKKYAEYMNSVIDNPYFVGAHWFQYIDSPLTGRAYDGENYNVGFVSIITDIPYT
S. degradans_AgaD     343  AASQADRGEMYKDYMQSVIDNPYFVGAHWFQYMDSPLTGRAYDGENYNVGFVDVTDTPYQ
S.c. A3 hyd.          339  AGTQAERARMYAEYMEQLIDNPYMVGGHWFQYADSPMTGRALDGENYNIGFVSVIDRPYP
```

FIG.3
(CONTINUED)

```
V. JT0107 AgaB      343  AASQQDRAKKYTNYMNSHADNPYFVGAHWFQYIDSPTTGRAMDGENYNVGFVSHTDTPYV
Azoto. AcOP         339  VYKEEEGPAYAHFLERALAEFFIVCMHWFQYLDQPATCRLLDGENGHIGLVGVTERPFA V. JT0107 AgaA      396  LMTDAAREFNCGMYGTDCSS-----                SEQ ID NO:27
Agar. JAMB-A11      394  LMTDAAREFNCGMYGTDCSSLSNA-                SEQ ID NO:28
Uncult. AguC        401  PLMKAAQEVNRNYQKREGK-----                 SEQ ID NO:29
S. degradans_AgaA   401  SLVDAAREVNKALYSRKPGE-----                SEQ ID NO:30
S. degradans_AgaD   403  EMVDAAKEVNAKENTERLGSK----                SEQ ID NO:31
S.c. A3 hyd.        399  EIVAAAREVNQRLNDRRYGNLATAE                SEQ ID NO:32
V. JT0107 AgaB      403  PLMEAAKKFNQDVYMLRYKK-----                SEQ ID NO:33
Azoto. AcOP         399  GFMERLRKAN---------------                SEQ ID NO:34
```

FIG.3
(CONTINUED)

```
S. degradans_AgaC   1 --LDVNPYIRHSVGGVDSFDRRKFIIIPASNTENDWFCGNDASLGFANESDDLITEFLEG    SEQ ID NO:35
Micros. MS109       1 --MDMCFNVKHMVCNVSMFDRNKFVIIPADVPEREMECDN----F----T-EDLRKDFLCR    SEQ ID NO:36
Microb. JAMB-A94    1 --MIVNANIKHSVKGISDFGNRHIIAHITIYEKDWEGHA----------DKLNYLVNT     SEQ ID NO:37
S. degradans_AgaE   1 --VSVNANFKRSVNGVFDFGRRRHIAHIALHEPDWVGHT----------DKLNYLFNT     SEQ ID NO:38
Micros. MS115       1 VQVDVNLNVKHSVGGVSDPGRDRHNIMESSITEPDWQGEE----------AKNDYLITD    SEQ ID NO:39
PA. atlantica AgrA  1 --MVVNLNVKHSVEGKSFPERQHIIGLESTINANDMQGEE----------DKLLCYMNEE   SEQ ID NO:40
Rh. baltica AgrA    1 --LPVKFIDIPYRTLGADRPRVPVNVRVDLQHELSIAGHVD---------LERQKFFRY    SEQ ID NO:41

S. degradans_AgaC  59 YDVYFGRDTGGISNHLS-QILEDPANPGFADEANMTSRGNDTKGWITVNPSEIAIKQRQH
Micros. MS109      51 YDVYLGRNTGGITWYLNQVTEDPEHPGYANPADVEAIGRNLKNQYAVNSVWQAYEHR--
Microb. JAMB-A94   48 LDVILGRDNGTATWSFL-DTKEDPANENMPDLDYMVIRGKELRENYEANPFYKRFSADR-
S. degradans_AgaE  48 LDVYMGRDNGSATWSFN-DITEDPAKPNMPNMDYMIERGKGLREAHDXNPLPKRFSAEX-
Micros. MS115      50 LDTMLGRDNGSATWSFA-STPQDPNNFHPSVDSMCSFGDWLKGEYESLTNRHQYESRA-
PA. atlantica AgrA 48 LDVYFGRDNGGTVWNIN-QAIEDPANIGYADPQMLIARGQAQFETNWGINKSALHQYDGR
Rh. baltica AgrA   49 YAAPGTSDPSFERWASE-RNFSPGRQIFKLDPALVVGYGPGEKLKEDPNNKGAADLTFFD S. degradans_AgaC  118 EHRNTIMEIGSQQHPFMPDGKLTGCGWALSQTETEAEPPGTATGHYMANFLAKFYKQS-E
Micros. MS109      109 ----NQQIIAAKLEPFMPDGQLTNCGWAFSQTDTEVEPPCTATEYMCRFIRDAFG---E
Microb. JAMB-A94   106 ----TELIAGTNPHPTYPTLSWNANGSTWED--WQPMHIETS-SANMGMLKHYYANS-S
S. degradans_AgaE  106 ----QLIIAGTNPHALYPTLSWFPNAFTWSG--WQPKNIETS-SANVGLMKEIYFANA-S
Micros. MS115      108 ----SGMIPGTNAHFTYPTLSWYANGSTWTDPQWQPKDVQIS-ADWVIEYLGKFFAHS-P
PA. atlantica AgrA107 ----GDLMIGGQPRAHYLGNTSPCCGGSAWQ-----AKGCDAVGDFLQYMNEFFRSAGE
Rh. baltica AgrA   108 R---HDSSPPKTIPEFEATDYAMCLNDYPEFMSVEHVGRGTPLIEHFCDAANLAAAHIAE S. degradans_AgaC  177 SDPNCQPKPVYMEVWNEPLYDLVDAATNP----TTPEKVPLFHNTVADERKLN----
Micros. MS109      162 GGTAQQPRPDYMELINEPVWHLVDYGD-------ESAEKVPRFHNGVAKAERQTV----
```

FIG.4

```
Microb. JAMB-A94   158 NGYIGDPMPKEWEVINEPDMERKTYKFMV----INQEAIMEYINLVAQEIRSKIGNEAP
S. degradans_AgaE  158 NGYVEEQLPEYWEVVNEPDMGYKTQFMV----INQEAIMEYINLVAQEIRDILGAEAP
Micros. MS115      162 S-VDGEPLPKYWEVVNEPDMEYMIKFMV----ISDEKIMEYINLVAQGVKERLGTDAP
PA. atlantica AgrA 158 PVTKGHLAPVYPEVLNEPLYQVTDAPHELGLEQPIPPIDIETFHNDVADAFRQN-----
Rh. baltica AgrA   165 QQRDGGRTAKWWEVKNESTLKAEWDYHYQK--EHDSWALLAEFHNAVAERVHAKTP----
```

```
S. degradans_AgaC  227 ------------------------------D-DVLIGGYTVAEPDFDSNN
Micros. MS109      210 ------------------------------P-DIQIGGYCIAEPNHEING
Microb. JAMB-A94   213 LIGGMTWGQHDFYRRDGISRYADNAYDQWIVADDPAEEAAAEEFFRQAMAITVDDTRDQN
S. degradans_AgaE  213 PIGGMTWGQHDFYRRDGISRFADDSYDQWITNDDQVLQAEARAFYRNAMAITVDDTRDQD
Micros. MS115      216 LIGGMTWGLHDLFAGDGLSRYQPDYLDQYLD-------AETASEFYRNAAATQMEGNQNQP
PA. atlantica AgrA 213 ------------------------------THEKIGGFTVAEPIFEQRE
Rh. baltica AgrA   219 ------------------------------SVNVGGPTSAMMQLHVNQ
```

```
S. degradans_AgaC  246 FERMENRDKAPIDIAGEKMDFISIHLYDFPNFQN-TQ-RY-----RKGSNVEATFDMLDH
Micros. MS109      229 FQEWNNRWKLFMDISGEYMDYVSIHLYDFPSINNGKQ-LY-----RKGSNMEATFDMMSQ
Microb. JAMB-A94   273 WYQMDVMWKGFMDAAGHNMDFYSMHVYDKPGVNSDAKSTL-----RNNGHLPAMLDMEW
S. degradans_AgaE  273 WYQMDVMWKGFMDAAGGNMDFYSIHIYDKEGENVGDTTVV-----RGGHITSAMLDMEW
Micros. MS115      269 WYQMDVQWKGFIDAAGANMDFYSVHFYDKPTYNASGG-AV-----RSGGHVEATLDMEW
PA. atlantica AgrA 232 FARMEERMKLFIDTSGSHMDVYSTMFYDLEDDNR----------FKGSRLEATLDMIDQ
Rh. baltica AgrA   237 FGLYRDQTR-PMDLTREHLDFYSRIFYEDMGSLGAWERRDKGYSGYLLGRLEATLDMLQA
```

```
S. degradans_AgaC  299 YTTLTLG--APLPLIVSEYGAPDHALFKAPWTPYRDGLKLKALNSLLMSMLERPDTLIKT
Micros. MS109      283 YSFLKFG--EVKPFMISEYGAQMHDYFGA-WSPYRDWLHLKSVMSMKQFMERPHIENKI
```

FIG.4
(CONTINUED)

```
Microb. JAMB-A94  328  YDMYQNGQANRKPIVISEYGAVQGGWNTLAHQPRPESEVLKSFNAMLMQILERPDYVIKS
S. degradans_AgaE 328  YDVKRNGFNNRKPIMLSEYGSVNGAWDNRAHEERYDIASKAFNGMLMQFLERPDYVIKS
Micros. MS115     323  YDMQKFGVSNRKPWISEYGAVQGSMTYLPHDNRYDWECIKPFNSMLMQFLERPDYIYT
PA. atlantica AgrA281  YSLLALG--ETKPHVISEYGGFNRPMENAPWSALRDWNFLKTASPMLMQFLSRPDSVLTS
Rh. baltica AgrA  296  HMEE---TDNVKPIILHECGSLQACRGAA-----DYWLRLKSPSAFLHKLASRPHQIDLS S. degradans_AgaC 357  IPFLPMKAEWGRDGVP--------YNDRLMRQKFEAEGETGNEMVITDLVKFYQLWADVN
Micros. MS109     340  INPLPVKAEWGTKGVND----T--YNHRLMRRENEPISYTG-QMVISELVKTYQLWSEVN
Microb. JAMB-A94  388  MPFTPAKPLWGYYPGGCGYEEVRNCTAPYHYSLLIEPVLNSDWQKSYIKFYELWADID
S. degradans_AgaE 388  LPFTPAKPLWGYLPGGCGYDDAVACTTRYHYAMLIEDELNSGNWENSSYIKFYELWADID
Micros. MS115     383  LPFTPIKAQWGDVD-----QNGDGTPEYNYQYKLMRDDDHDGNWESDYIKFYELWSEVK
PA. atlantica AgrA339  IPFMPIKALWGTAADG------TPYNWRLIRQQKEAPNETGENWMFTEMVKFYQLWSDVK
Rh. baltica AgrA  348  VPFVFTNMHWNPTSG---------NVARVPTEGASARGPLADFQPIPVADFFELWRDFD S. degradans_AgaC 409  GTRVISYA---ADMILVDSYVDGSTLYLILNNLEFNDEILHLTDLGLNNNSFVSGTMRE
Micros. MS109     393  GTRIDIYS---PNADILVDGYVECKNAYLILNNLNFEPAEIDLKSHGLSDNNEVSIEIKH
Microb. JAMB-A94  448  GTRVDSMS---SDPDVQVQSYVNNELFIINNLETVDTTIDLTVAGLNNAQLQNWELRN
S. degradans_AgaE 448  GTRVDSKS---SDVIVQVDSYVKGNELFVILNNLEAADTIVNLDVS--GIASVQNRELRN
Micros. MS115     438  GTRIDIKS---TDPDIQIDAYVDGKDVFLILNNLENQATTIHLNLYEDFGNNVQNWNIKH
PA. atlantica AgrA393  GTRVDIFS---TNSDFLIDSYVQNDKAYVLISNLTEQAEKIWHKYGAPASSQPITRIKI
Rh. baltica AgrA  398  GRRLPVATNDLAHVGLNATAVYQGNRLQIALTNMTSHQLSVHLSDIAGDALHASSIQQPI
```

FIG.4
(CONTINUED)

```
S. degradans_AgaC  466  LHTV-DGNPVLSESALANIPTNLITIGGEATIVLALNFENDIAISEISEEIKYYAIIYKQ-
Micros. MS109      450  LYLD-GDAPVLSTSVESSVPESLLAAEGIMIELIMEEPIEPVQSSIEKKYYADIYLQ-
Microb. JAMB-A94   505  MHFDNNFDTQLERHHMKQVPIKVTLAADAILVLRYTLNSTIAIRQSVDEKKVFGNESVSGG
S. degradans_AgaE  503  MHFD-IQETHLERHMSAAPKTVTLAADAIWVLRYTLASSVAMNIMEKKYFGESVSGG
Micros. MS115      495  LHLTGTSTVTLENNDHATAPESVQLAGDGIMVIKYIYGSAVNIHNSIEKKFYGESLSG-
PA. atlantica AgrA 450  LYLK-GAAPRLMKQVMRQISKKSRLLLKRLW------------------------
Rh. baltica AgrA   458  LRYN-DGEVIYEDAISLSDSNAIEVDAEETTVLIEIFDQTIQPNRILLRQFAMYAGTAVP S. degradans_AgaC  524  -----AITANTDISFAINNVALGD---QGEAILRLGIGRDHGLSLQPS-------VSVNG
Micros. MS109      508  -----EIVSETPITFNIENVEVGE---YGEAMLRMGIGRQHGKSLAPS-------VLFNG
Microb. JAMB-A94   565  SVPHRISVAGGAKNLQVNNVSVPS--GYAESQLRLIVALYPSQDTPDSLLQIDTLIING
S. degradans_AgaE  562  IEPHRISVAGGAKILYINNVSVPS--GYSEAILRITVSLYPDEDDKVGGHLSLDSIIVNG
Micros. MS115      554  TVPNRVSIPNGEMIMQINGVDVPADASKAEAMLRITCALYNDDINQVG-HLSIDKLIVNG
PA. atlantica AgrA      ------------------------------------------------------------
Rh. baltica AgrA   517  --------ADQTQIFQLDIDDASD---IESAELVMGVHRIKGLEQAVS-------GTFNG S. degradans_AgaC  569  VDVEVPSDIRGYDQFHNGTGRPNFYGVIEIPVEYSALQTSNTMVVNFPDSTGFVTTAALQ
Micros. MS109      553  QNIHVPKNFRGDDQED----RATFFGVLEIPVSYDLIKQKNEVQITFSDDGGHVSSVAMQ
Microb. JAMB-A94   623  HTIEIPIDWRGRKENS----VERYFNTLEIPVPVDVLQKNNTIISVDFRHNG-ELIVANLV
S. degradans_AgaE  620  TAIEAPIDWKGPKANR----AERFFGVLDIPVPVELLQSTNTIAVDFRHNG-ELIVANLI
Micros. MS115      613  TEIETPLDWRG-TNQV----RNRYFSTLEIPVPVGLLQTNNTFTVDFHHVG-EVAVVNLQ
PA. atlantica AgrA      ------------------------------------------------------------
Rh. baltica AgrA   559  HRFESHPEWTH--------QFDQLLAPLEIPISKDWLQNNNQIQLEPQPGLTITSVHLIC
```

FIG.4
(CONTINUED)

| | | |
|---|---|---|
| S. degradans_AgaC | 629 MFNTSTSITRPMQ | SEQ ID NO:35 |
| Micros. MS109 | 609 MFNFSVPIER--- | SEQ ID NO:36 |
| Microb. JAMB-A94 | 676 IKEYTTTPVEH-- | SEQ ID NO:37 |
| S. degradans_AgaE | 675 VSEFTSEPNR--- | SEQ ID NO:38 |
| Micros. MS115 | 667 TWEFSKVPGRS-- | SEQ ID NO:39 |
| PA. atlantica AgrA | ------------- | SEQ ID NO:40 |
| Rh. baltica AgrA | 611 DSISEALDSKHSQ | SEQ ID NO:41 |

FIG.4
(CONTINUED)

```
E1    1  -GAADYVIEAENPVAQGGTIVDGQPNKVSVYSVNGATAINYVRADYTDYQINVATHGYY    SEQ ID NO:42

E2    1  PSPQLVKTEAEANAQSGTFADGQPTPVSMYIVNGKTAINFVNKGDAVEYNLVAPAAGSY    SEQ ID NO:43

B2    1  PSTASIAMEAENPNAVGGTFSDGQAPVSMYIVNGNTAINYVRQGDYADYTIAVAQAGNY    SEQ ID NO:44

E3    1  PVSGSFKLEAEHFQKVGG--------EVQIYSLSPGNAVNYFNSGDYLEFVMLDAGGLY    SEQ ID NO:45

B1    1  ---------GKEGSAVAG--------DTFTGFNPSGANNINYNTLGDVADYTVNFPAAGNY  SEQ ID NO:46

E1   60  NVQYAIGTSVASGAAIRLLVQNGS-SWESQGQINVPV-GHNDSIQPLNASH-EVILPAGI

E2   61  ALKYSIGTSVASGSEVLFFVLKNN-VWVSQGKTPVPA-VGWDNITSVASAQ-TVELAAGS

B2   61  TISYQAGSGVTGG-SIEFLVNENG-SNASKTVIAVPN-QGWNDFQPLNGG--SVYILSAGI

E3   53  EASFRVGTGVASDVAVGLMVTDHKGDLTLKSVTPVTDQGGNDAFYNLTAQS-QLNIYSGI

B1   45  TVNLIAASPVTSGLGADILVDSSY-----AGTIPVSSTGANEIYNTFSLPSSIYIASAGN

E1  117  VNLRVVGAGSNDWQWNLDSISLTL-                                   SEQ ID NO:42

E2  118  NKVKLVGAGINDWQWNLDFFELTL-                                   SEQ ID NO:43

B2  116  HQVRLHGAGSNNWQWNLDKFILSN-                                   SEQ ID NO:44

E3  112  NTIRITGAGSADMWDSITLTR-                                      SEQ ID NO:45

B1  100  HTIRVQSSGGSANQWNGDELRFTQT                                   SEQ ID NO:46
```

ENZYMIC PRODUCTION OF NEOAGAROBIOSE

STATEMENT REGARDING FEDERALLY SPONSORED RESEARCH OR DEVELOPMENT

The subject matter of this application was in part funded by the National Science Foundation (DEB0109869) and from Maryland Sea Grant. The government has certain rights in this invention.

CROSS-REFERENCE TO RELATED APPLICATION

The present application claims priority to U.S. Provisional Application Ser. No. 60/914,791, ENZYMIC PRODUCTION OF NEOAGAROBIOSE, filed on Apr. 30, 2007 and is hereby incorporated in its entirety by reference.

INCORPORATION-BY-REFERENCE OF MATERIAL SUBMITTED ON A COMPACT DISC

Not applicable.

FIELD OF THE INVENTION

The invention is directed to compositions and methods for the production of degradation products of agar, agarose, and derivatives thereof, including the production of neoagarobiose.

BACKGROUND OF THE INVENTION

*Saccharophagus degradans* 2-40 (formerly *Microbulbifer degradans* 2-40) is a rod-shaped, aerobic, marine bacterium isolated from the surface of decomposing saltwater cord grass, *Spartina alterniflora*, in the lower Chesapeake Bay (Andrykovitch and Marx, 1988). *S. degradans* 2-40 is related to a group of marine γ-subgroup proteobacteria capable of degrading complex polysaccharides (CPs) (Ekborg et al., 2005; Gonzalez and Weiner, 2000), a critical function in the marine food web. *S. degradans* 2-40 is unique among these bacteria due to its ability to utilize CPs of algal, higher plant, fungal, and animal origins, such as agar, alginate, cellulose, chitin, β-glucan, laminarin, pectin, pullulan, starch, and xylan, as sole carbon and energy sources (Andrykovitch and Marx, 1988; Ensor et al., 1999; Howard et al., 2003; Kelly et al., 1990). The mechanism by which this bacterium degrades these normally recalcitrant substrates has been established only for the chitinolytic system (Howard et al., 2003).

Agar, a cell wall constituent of many red algae (*Rhodophyta*), exists in nature as a mixture of unsubstituted and substituted agarose polymers that form an agarocolloid gel (Craigie, 1990; Duckworth and Yaphe, 1970). Agarose is composed of repeating neoagarobiose units (3-6-anhydro-L-galactose-α1-3-D-galactose) joined by β1-4 bonds that form a helix in aqueous environments. The galactose moieties of the repeating neoagarobiose units can be methylated, pyruvated, sulfonated, or glycosylated to form various substituted derivatives with different gelling and solubility characteristics. Up to 70% of the algal cell wall can be agar polymers. The remaining material consists of other galactans and embedded xylan and cellulose microfibrils.

Agarolytic organisms are common, but comparatively few agarase systems have been characterized. Agar-degrading agarase systems were first reported by Gran in 1902 (Swartz and Gordon, 1959). Since then, at least 30 bacteria with this capacity have been identified. The vast majority of these bacteria are marine isolates belonging to the following genera: *Agarivorans* (Ohta et al., 2005), *Alterococcus* (Shieh and Jean, 1998), *Alteromonas* (Potin et al., 1993), *Cytophaga* (Turvey and Christison, 1967; Van der Meulen and Harder, 1975), *Microbulbifer* (Ohta et al., 2004a; Ohta et al., 2004b), *Microscilla* (Zhong et al., 2001), *Pseudoalteromonas* (Belas, 1989; Morrice et al., 1983a; Morrice et al., 1983b; Schroeder et al., 2003), *Pseudomonas* (Ha et al., 1997; Kang et al., 2003), *Vibrio* (Aoki et al., 1990; Araki et al., 1998; Sugano et al., 1994a; Sugano et al., 1993; Sugano et al., 1994b), and *Zobellia* (Allouch et al., 2003; Barbeyron et al., 2001). Agarase activity has also been observed in bacteria isolated from terrestrial environments, such as *Paenibacillus* spp. (Hosoda et al., 2003; Uetanabaro et al., 2003) and *Streptomyces coelicolor* (Bibb et al., 1987).

Each of these organisms is thought to degrade agar by using one of two biochemical pathways that employ a variety of secreted agarases. Most known agarolytic bacteria use secreted β-agarases to cleave agarose initially at the β1,4 linkages between neoagarobiose units. In this pathway, β-agarase I is thought to endolytically degrade agarose to neoagarooligosaccharides, with neoagarotetraose as the smallest product (Morrice et al., 1983a; Morrice et al., 1983b). These neoagarooligosaccharides appear to be degraded further by a β-agarase II to yield neoagarohexaose, neoagarotetraose, and neoagarobiose (Morrice et al., 1983a; Morrice et al., 1983b). This enzyme can have both endolytic and exolytic activities. A neoagarobiose hydrolase then cleaves neoagarobiose to its constituent monosaccharides. A few bacterial species employ an α-agarase pathway in which the α1,3 linkage within neoagarobiose units is cleaved initially. For example, *Alteromonas agarlyticus* secretes a depolymerizing agarase that yields agarotetraose (Potin et al., 1993). While the activities of these enzymes have been demonstrated and some have been purified, the nucleotide sequences of comparatively few agarase genes have been determined. GH16, GH50, and GH86 domains have been reported to be present in β-agarases and GH96 domains in α-agarases (see the Carbohydrate Active Enzymes (CAZY) database; (Coutinho and Henrissat, 1999a)). There is at least one report of a partial amino-terminal sequence of an α-neoagarooligosaccharide hydrolase (Sugano et al., 1994a).

*S. degradans* 2-40 is capable of rapid growth on agarose as the sole carbon source, degrading agar nearly twice as quickly as *Pseudoalteromonas atlantica*, and appears to produce multiple agarases (Whitehead et al., 2001). The mechanism by which *S. degradans* 2-40 degrades agar is thought to involve a β-agarase system (Whitehead et al., 2001). Recently, the genome sequence of *S. degradans* 2-40 was completed to enable the application of genomic approaches to the characterization of this agarolytic system.

There are numerous applications of agar and its enzymatically derived by-products. Neoagarobiose is highly sought for cosmetic applications, including moisturizers, and for its ability to whiten melanoma cells. Neoagarobiose is desirable for moisturizer formulations because it has a higher hygroscopic ability than glycerol or hyaluronic acid, typical moisturizing reagents. Besides being able to whiten melanoma cells, it also has low cytotoxicity (Kobayashi et al., 1997) and is hypoallergenic. Neoagarobiose is not readily available commercially, due to a challenges in its synthesis, and difficulty to produce from primary sources, such as agar.

Publications referred to throughout the specification are herein incorporated by reference in their entireties.

SUMMARY OF THE INVENTION

In a first aspect, the invention is drawn to methods of producing neoagarobiose, comprising: (a) providing a substrate selected from the group consisting of agar, agarose, neoagarotetraose, agarooligosaccharides, and derivatives thereof; (b) contacting the substrate with an Aga86E polypeptide, thereby creating a reaction mix; and (c) incubating the reaction mix under suitable conditions and sufficient time to produce neoagarobiose from the substrate. The Aga86E polypeptide can be provided on a solid support, and can be linked to the solid support chemically, by a protein, such as an antibody, or via streptavidin/avidin-biotin couplings, or even by plain adsorption, based on charge. Any solid support material can be used, such as polystyrene, cross-linked agarose, magnetic material, or polyacrylamide.7. The Aga86E polypeptide can be a polypeptide having an amino acid sequence with at least 70%, 80%, 90%, 95% and 100% sequence identity with an amino acid sequence of SEQ ID NO:3. Variants of Aga86E polypeptides can also be used that maintain Aga86E activity and which conserve the amino acid residues that are shown to be conserved in the polypeptides various domains as shown in FIGS. 4 and 5. The reaction mix can further comprises a buffer, the buffer selected from the group consisting of phosphate, Hank's Balanced Salt Solution (HBSS), N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl) piperazine-N'3-propanesulfonic acid (EPPS or HEPPS), glyclclycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), and tris(hydroxymethyl)-aminomethane (Tris).

In some aspects, the method further comprises contacting the substrate with a Aga16B polypeptide. The Ag16B polypeptide can be a polypeptide having an amino acid sequence with at least 70%, 80%, 90%, 95% and 100% sequence identity with an amino acid sequence of SEQ ID NO:1. Variants of Aga16B polypeptides can also be used that maintain Aga16B activity and which conserve the amino acid residues that are shown to be conserved in the polypeptides various domains as shown in FIGS. 2 and 5. In some aspects, the substrate is first contacted with the Aga16B polypeptide.

In a second aspect, the invention is drawn to methods of producing neoagarobiose, comprising: (a) providing a substrate selected from the group consisting of agar, agarose, neoagarotetraose, agarooligosaccharides, and derivatives thereof; (b) contacting the substrate with a first polypeptide having at least 80%, 90%, or 100% sequence identity with an amino acid sequence of SEQ ID NO:9, thereby creating a reaction mix; and (c) incubating the reaction mix under suitable conditions and sufficient time to produce neoagarobiose from the substrate. Variants of the polypeptide comprising an amino acid sequence of SEQ ID NO:9 can also be used, wherein conserved amino acid residues as shown in FIG. 4 are conserved. In some aspects, the method further comprises contacting the substrate with at least one carbohydrate binding module polypeptide having at least 80%, 90% or 100% sequence identity with an amino acid sequence selected from the group consisting of SEQ ID NOs:5, 6 and 7. In yet other aspects, the substrate is contacted with two of the carbohydrate binding module polypeptides of SEQ ID NOs:5, 6 and 7, and in yet other aspects to all three. Variants of polypeptides comprising SEQ ID NOs:5, 6 and 7 can also be used, wherein conserved residues are conserved as shown in FIG. 5. The polypeptides can be fused together in any combination.

In some aspects, the methods further comprise contacting the substrate with a second polypeptide comprising an amino acid sequence having at least 80%, 90% and 100% sequence identity with an amino acid sequence of SEQ ID NO:12. Variants of polypeptides comprising SEQ ID NO:12 can also be used, wherein conserved residues are conserved as shown in FIG. 2. In some aspects, the methods comprising contacting the substrate first with the second polypeptide. Furthermore, the methods can further comprising contacting the substrate with at least one carbohydrate binding module polypeptide having at least 80%, 90% or 100% sequence identity with an amino acid sequence of SEQ ID NO:10 or 11. Variants of polypeptides comprising SEQ ID NOs:10 and 11 can also be used, wherein conserved residues are conserved as shown in FIG. 5. Any of the polypeptides can be provided on solid supports. In some aspects, a single solid support comprises multiple, different polypeptides. In yet other aspects, the polypeptides can be fused in any combination.

In yet another aspect, the invention is drawn to methods of producing neoagarobiose, comprising: (a) providing a substrate selected from the group consisting of agar, agarose, neoagarotetraose, agarooligosaccharides, and derivatives thereof; (b) contacting the substrate with an Aga86E polypeptide of SEQ ID NO:1 and an Aga16B polypeptide of SEQ ID NO:3, thereby creating a reaction mix; and (c) incubating the reaction mix under suitable conditions and sufficient time to produce neoagarobiose from the substrate. In some aspects, the methods coprising contacting the substrate first with the Aga16B polypeptide before being contacted with the Aga86E polypeptide. The reaction mix can incubated at a temperature of about 42° C. Any of the polypeptides can be provided on solid supports. In some aspects, a single solid support comprises multiple, different polypeptides. In yet other aspects, the polypeptides can be fused in any combination.

In yet another aspect, the invention is drawn to systems to produce neoagarobiose, comprising: (a) an isolated Aga86E polypeptide; (b) an isolated Aga16B polypeptide; and (c) a buffer. In some aspects, the systems further comprise a substrate selected form the group consisting of agarose, neoagarotetraose, and agarooligosaccharide. Any of the polypeptides can be provided on solid supports. In some aspects, a single solid support comprises multiple, different polypeptides. In yet other aspects, the polypeptides can be fused in any combination.

BRIEF DESCRIPTION OF THE SEVERAL VIEWS OF THE DRAWING

FIG. 2 shows sequence similarities observed in GH16 domains of known or predicted agarases. Regions of agarases exhibiting sequence similarity to Aga16B were aligned using ClustalW. Black boxes indicate identity. Gray boxes similarity. The signature sequence for a GH16 domain is overlined. The amino acid residues of the region exhibiting the indicated sequence similarity is listed as "residues". Total length of the polypeptide is indicated as the "total". *Aeromonas* b-Aga, *Aeromonas* β-agarase, gi|6073784, residues 32-290/290 total; *Pa. atlantica* DagA, *Pseudoalteromonas atlantica* β-agarase I DagA, gi|1220461, residues 24-290/290 total; *Zobellia* AgaA, *Zobellia galactanvorans* β-agarase AgaA, gi|16650393, residues 35-295/539 total; Microb. JAMB-A7, *Microbulbifer* sp. JAMB-A7 β-agarase AgaA7, gi|37665541, residues 22-307/441 total; *S. degradans* Aga16B, *Saccharophagus degradans* 2-40 β-agarase Aga16B, AAT67062, residues 31-289/593; Pm ND137, *Pseudomonas* sp. ND137 agarase, gi|58219335, residues 23-300/591 total; Microb. JAMB-A94, *Microbulbifer* sp JAMB-A94 β-agarase AgaA, gi|50344693, residues 24-298/433 total; Pm ND137, *Pseudomonas* sp ND137 β-agarase AagA, gi|17826962, residues 25-299/441 total; *Zobellia* AgaB, *Z. galactanvorans* β-agarase AgaB, gi|6650395, residues 54-353/353; Micros. MSI 16, *Microscilla* sp. PRE1 predicted agarase MS116, gi|14484956, residues 22-386/614 total; Pa. CY24 AgaA, *Pseudoalteromonas* sp. CY24 β-agarase AgaA, gi|30043922, residues 54-297/453 total; S.c. A3 DagA, *Streptomyces coelicolor* A3 DagA, gi|21221895, residues 30-309/309 total. SEQ ID NOs are indicated in the figure.

FIG. 3 shows sequence similarities observed in GH50 domains of known or predicted agarases. Regions of agarases exhibiting sequence similarity to the region conserved between AgaA and Aga50D were aligned using ClustalW. V. JT0107 AgaA, *Vibrio* sp. JT0107 AgaA, gi|497893, residues 505-919/995 total; Agar. JAMB-A11, *Agarivorans* sp. JAMB-A11 agarase, gi|67423393, residues 507-923, 995 total; Uncult. AguC, Uncultured bacterium AguC, gi|37222154, residues 353-772/772 total; *S. degradans* AgaA, *Saccharophagus degradans* 2-40 AgaA, gi|48861348, residues 350-769/769 total; *S. degradans* Aga50D, *Saccharophagus degradans* 2-40 Aga50D, gi|48861458, residues 325-747/747 total; S.c. A3 hyd., *Streptomyces coelicolor* A3 putative hydrolase, gi|6469474, residues 366-788/798 total; V. JT0107 AgaB, *Vibrio* sp JT0107 β-agarase AgaB, gi|531270, residues 534-955/955 total; Azoto. AVOP, *Azotobacter vinlandii* AvOP agarase, gi|67157228, residues 427-768/801 total. SEQ ID NOs are indicated in the figure.

FIG. 4 shows sequence similarities observed in GH86 domains of known or predicted agarases. Regions of agarases exhibiting sequence similarity to the region conserved between Aga86C and Aga86E were aligned using Clustal W. *S. degradans* Aga86C, *Saccharophagus degradans* 2-40 Aga86C, gi|48861753, residues 147-787/787 total; Micros. MS109, *Microscilla* sp PRE1 putative β-agarase MS109, pi|14518314, residues 30-647/736 total; Microb. JAMB-A94, *Microbulbifer* sp. JAMB-A94 AgaO, gi|57864209, residues 488-1175/1175 total; *S. degradans* Aga86E, *S. degradans* outer membrane protein Aga86E, gi|48861758, residues 633-1316,1316 total; Micros. MS115, *Microscilla* sp PRE1 putative agarases MS115, gi|14518320, residues 34-700/1330 total; Pa. atlantica AgrA, *Pseudoalteromonas atlantica* β-agarase AgrA, gi|94831, residues 27-505/505 total; Rh. baltica AgrA, *Rhodopirellula baltica* SH1 AgrA, gi|32443741, residues 189-811/811 total. SEQ ID NOs are indicated in the figure.

FIG. 5 shows sequence similarities observed in the predicted CBM domains of *S. degradans* agarases and known CBM6 modules. Modules identified by SMART analysis in Aga16B and Aga86E were aligned using ClustalW. Module designations are indicated in FIG. 1. Amino acid residues shown are: B1, 322-445; B2, 455-493; E1, 9-148, E2, 162-302; E3, 349-483. SEQ ID NOs are indicated in the figure.

DETAILED DESCRIPTION

Figure 1:
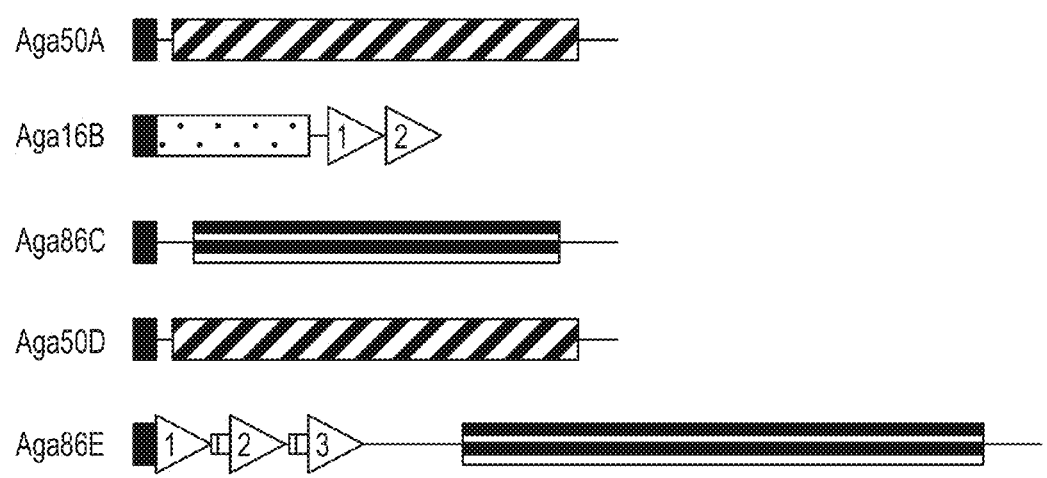
FIG. 1 shows predicted structural features of *S. degradans* agarases. The indicated domains were identified by sequence similarity. Black box, type II protein secretion signal; white dotted box, GH16 domain; cross-hatched box, GH50 domain; horizontally striped box, GH86 domain; vertically striped box, repeated amino acid linker. Filled triangles indicate family 6 carbohydrate binding modules.

The present invention solves the problems of readily providing a source of neoagarobiose. The invention exploits Aga86E of *S. degradans*, which before the discovery by the current inventors, was thought to be yet another β-agarase without any remarkable enzymatic activity. The inventors discovered that Aga86E has the remarkable ability to exolytically degrade agarose and agarooligosaccharides to release neoagarobiose. Aga86E is therefore not an ordinary agarase; it is a neoagarobiosebiohydralase. Furthermore, the inventors discovered that combining the endolytic activity of another β-agarase, Aga16B, the process of degrading agar or agarose to neoagarobiose was even more efficient. The invention exploits these findings, disclosing methods and systems directed to produce neoagarobiose.

In their study that led to the discoveries that brought about the present invention, traditional genomic library screens and protein expression coupled with bioinformatic analysis of the genome sequence and proteomics were used to identify five agarases encoded by *S. degradans* 2-40. Several of the agarases, including Aga86E and Aga16B of the present invention, were found to have unusual structural features, such as multiple carbohydrate binding modules from family 6 (CBM6).

The identification of the *S. degradans* 2-40 agarases was based upon sequence similarity, conserved structural features, agarase activity of expressed genes in *E. coli*, and/or the phenotype of gene replacement mutants.

Aga16B was unequivocally demonstrated by the inventors to be a secreted β-agarase (see the Examples, below). All agarase-positive clones identified in the *S. degradans* 2-40 genomic library included aga16B. The enzyme exhibited sequence similarity to a family of GH16-containing agarases, and the signature sequence for a GH16 catalytic domain was present. When cloned to produce a His-tagged derivative, the purified product had agarase activity in zymograms and endolytically degraded agar similarly to a β-agarase I, producing neoagarotetraose as the smallest product. Analysis of culture filtrates of *S. degradans* 2-40 by mass spectrometry indicated that the enzyme is expressed during bacterial growth where agar was the sole carbon source. Multiple forms of Aga16B were observed in zymograms of affinity-purified preparations. These forms were similar to the forms observed in culture filtrates of *S. degradans* 2-40, suggesting that Aga16B is the predominant β-agarase I secreted by the bacterium.

Aga86E is a special agarase, a neoagarobiosebiohydralase. Sequence similarity to several other agarases, as well as to a probable GH86 domain found only in agarases, was detected. When cloned to create a His-tagged derivative, the purified product was active in degrading agarose, releasing almost specifically neoagarobiose. This is consistent with exolytic degradation of agarose polymers. The active derivatives of Aga86E appear to be amino-terminal truncations of 100 and 86 kDa. These are proteolytic products lacking one or more of the CBMs but formed even in the presence of broad-spectrum protease inhibitors.

Like most other carbohydrases characterized thus far, the *S. degradans* 2-40 agarases are modular. The catalytic domains found in these agarases include GH16, GH50, or GH86 domains. GH16 domains are not specific to agarases and have been found in enzymes with other activities, such as β-galactosidases, endoglucanases, lichenases, and carrageenanases (Allouch et al., 2004). The crystal structure of an agarase-active GH16 domain from *Zobellia galactanivorans* has been characterized (Allouch et al., 2003). This module contains two parallel binding sites that are thought to unwind the helical structure of agarose (Allouch et al., 2004). Since the functional residues are conserved, the endolytic hydrolysis of agarose by Aga16B is similar. There are several regions of sequence conservation within each of the predicted GH50 and GH86 domains that represent conserved active sites and/or binding domains. Like several other GH domains, the GH50 and GH86 domains have been associated with both endolytic and exolytic activities. For example, the GH86 family agarase of a deep-sea *Microbulbifer*-like strain has been reported to endolytically degrade agarose, but the inventors found that the GH86-containing Aga86E surprisingly exolytically degrades agarose to release neoagarobiose.

More unusual are the presence of multiple CBM6 in Aga16B and Aga86E. Aga16B has two homologs of CBM6, whereas Aga86E has three. While CBM are common in other carbohydrases, a survey for CBM in other agarases revealed only two other agarases with CBM-like domains. The CBM6 found in Aga86E and Aga16B form a distinct subclass within the large CBM6 family. Notably, deletion of the CBM6 did not affect the catalytic activity of either enzyme, as the catalytic GH16 and GH86 domains function independently of other domains. These domains increase the affinity of these enzymes for their substrate or disrupt interactions between adjacent polymers (Xu et al., 2004). Phylogenetic analyses indicate that this CBM6 is most similar to the first and second CBM6 of the exo-acting Aga86E.

In the following sections, the invention is described first by defining terms; therein follows a discussion of the Aga86E and Aga16B polypeptides and polynucleotides that can be used to make the polypeptides. Following the presentation of the polypeptides, various ways of using the Aga86E and Aga16B polypeptides are discussed, followed by examples that further elucidate the invention.

DEFINITIONS

The term, "Aga86E/16B polypeptides" refers to any polypeptide, including, full-length polypeptides, and domain fragments, such as CBMs and catalytic domains, that make up Aga86E polypeptide (SEQ ID NO:1) and Aga16B polypeptide (SEQ ID NO:3). The term is meant to be one of convenience and brings no limitation to the present invention. Examples of Aga86E/16 polypeptides are those represented by SEQ ID NOs:1, 3, 5-7, 9-12. Any combination of these sequences when fused together, with or without repeat sequences such as those of SEQ ID NOs:8 and 13, are also Aga86E/16B polypeptides. An "Aga86E/16B polynucleotide" is a polynucleotide that encodes an Aga86E/16B polypeptide.

A "polynucleotide" is a nucleic acid polymer of ribonucleic acid (RNA), deoxyribonucleic acid (DNA), modified RNA or DNA, or RNA or DNA mimetics (such as, PNAs), and derivatives thereof, and homologues thereof. Thus, polynucleotides include polymers composed of naturally occurring nucleobases, sugars and covalent inter-nucleoside (backbone) linkages as well as polymers having non-naturally-occurring portions that function similarly. Such modified or substituted nucleic acid polymers are well known in the art and for the purposes of the present invention, are referred to as "analogues." Oligonucleotides are generally short polynucleotides from about 10 to up to about 160 or 200 nucleotides.

"Aga86E/16B variant polynucleotide" or "Aga86E/16B variant nucleic acid sequence" means a Aga86E/16B variant polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of Aga86E/16B. Variants do not encompass the native nucleotide sequence.

Ordinarily, Aga86E/16B variant polynucleotides are at least about 8 nucleotides in length, often at least about 50, 55, 60 nucleotides in length, or even about 75-200 to wild-type full-length nucleotides in length, or more.

"Percent (%) nucleic acid sequence identity" with respect to Aga86E/16B-nucleic acid sequences is defined as the percentage of nucleotides in a candidate sequence that are identical with the nucleotides in the Aga86E/16B sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

% nucleic acid sequence identity=W/Z·100 where

W is the number of nucleotides cored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

"Consisting essentially of a polynucleotide having a % sequence identity" means, when applied to a polynucleotide, that the polynucleotide does not substantially differ in length, but in sequence. Thus, a polynucleotide "A" consisting essentially of a polynucleotide having 80% sequence identity to a known sequence "B" of 100 nucleotides means that polynucleotide "A" is about 100 nts long, but up to 20 nts can vary from the "B" sequence. The polynucleotide can be longer or shorter due to the addition of 1-15 nucleotides on the termini to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favor specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide, which decreases DNA duplex stability. A common approach is to vary the temperature: higher relative temperatures result in more stringent reaction conditions. (Ausubel et al., 1987) provide an excellent explanation of stringency of hybridization reactions.

To hybridize under "stringent conditions" describes hybridization protocols in which nucleotide sequences at least 60% homologous to each other remain hybridized.

The polynucleotides can be prepared by conventional techniques, such as solid-phase synthesis using commercially available equipment, such as that available from Applied Biosystems USA Inc. (Foster City, Calif.; USA), DuPont, (Wilmington, Del.; USA), or Milligen (Bedford, Mass.; USA). Modified polynucleotides, such as phosphorothioates and alkylated derivatives, can also be readily prepared by similar methods known in the art.

In general, a Aga86E/16B variant that preserves Aga86E/16B-like function and includes any variant in which residues at a particular position in the sequence have been substituted by other amino acids, and further includes the possibility of inserting an additional residue or residues between two residues of the parent polypeptide as well as the possibility of deleting one or more residues from the parent sequence. Useful conservative substitutions are shown in Table 1. Conservative substitutions whereby an amino acid of one class is replaced with another amino acid of the same type fall within the scope of the subject invention so long as the substitution does not materially alter the biological activity of the compound. If such substitutions result in a change in biological activity, then more substantial changes, indicated in Table 2 as exemplary, are introduced and the products screened for its ability to degrade agarose or agarooligosaccharides.

TABLE 1

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |

TABLE 1-continued

Preferred substitutions

| Original residue | Exemplary substitutions | Preferred substitutions |
|---|---|---|
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge or (3) hydrophobicity, or (4) the bulk of the side chain of the target site can modify Aga86E/16B polypeptide function or immunological identity. Residues are divided into groups based on common side-chain properties as denoted in Table B. Non-conservative substitutions entail exchanging a member of one of these classes for another class. Substitutions can be introduced into conservative substitution sites or more preferably into non-conserved sites.

TABLE 2

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis.

"Aga86E/16B polypeptide variant" means an active Aga86E/16B having at least: (1) about 70% amino acid sequence identity with a full-length native Aga86E/16B sequence, (2) a Aga86E/16B sequence lacking a signal peptide, (3) an extracellular domain of a Aga86E/16B, with or without a signal peptide, or (4) any other fragment of a full-length Aga86E/16B sequence. For example, Aga86E/16B variants include those wherein one or more amino acid residues are added or deleted at the N- or C-terminus of the full-length native amino acid sequence. An Aga86E/16B polypeptide variant will have at least about 70% or 80% amino acid sequence identity, preferably at least about 81% amino acid sequence identity, more preferably at least about 82%-98% amino acid sequence identity and most preferably at least about 99% amino acid sequence identity with a full-length native sequence Aga86E/16B sequence. Ordinarily, Aga86E/16B variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in a Aga86E/16B sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Publicly available computer software such as BLAST, BLAST2, ALIGN2 or Megalign (DNAS-TAR) can be used to align polypeptide sequences.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=X/Y·100 where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Useful variants are those that conserve the conserved amino acid residues as shown in FIGS. 2-5, or wherein preferred conservative substitutions have been made.

An "isolated" or "purified" polypeptide, or biologically active fragment is separated and/or recovered from a component of its natural environment. Contaminant components include materials that would typically interfere the use for the polypeptide; such undesirable contaminants would significantly interfere with enzymatic activity (e.g., such as that of the GH domains of the Aga86E and Aga16B polypeptides), or binding activity, such as that of the CBMs. To be substantially isolated, preparations have less than 30% by dry weight of contaminants, more preferably less than 20%, 10% and most preferably less than 5% contaminants. An isolated, recombinantly-produced Aga86E/16B or biologically active portion is usually substantially free of culture medium, i.e., culture medium represents less than 20%, more or less than about 10%, or less than about 5% of the volume of the Aga86E/16B preparation.

Biologically active portions of Aga86E/16B include peptides comprising amino acid sequences sufficiently homologous to, or derived from, the amino acid sequences of Aga86E/16B (SEQ ID NOS:1, 3, 5, 6, 7, 9-12) that include fewer amino acids than the full-length Aga86E/16B, and exhibit at least one activity of a Aga86E/16B. Biologically active portions comprise a domain or motif with at least one activity of native Aga86E/16B, such as endolytic activity on a substrate (Aga16B) or exolytic activity on a substrate (Aga86E), and binding to a carbohydrate moiety (CBMs). A biologically active portion of a Aga86E/16B can be a polypeptide that is 10, 25, 50, 100 or more amino acid residues in length.

Biologically active portions of a Aga86E/16B can have an amino acid sequence shown in SEQ ID NOS:1, 3, 5, 6, 7, 9-12, or be substantially identical to SEQ ID NOS:1, 3, 5, 6, 7, 9-12, and retains the functional activity of the polypeptide of SEQ ID NOS:1, 3, 5, 6, 7, 9-12. Other biologically active Aga86E/16B polypeptides can comprise an amino acid sequence at least 45% identical to the amino acid sequence of SEQ ID NOS:1, 3, 5, 6, 7, 9-12, and retain a functional activity of native Aga86E/16B. Biological activity of Aga86E polypeptides include carbohydrate binding and neoagarobiosebiohydralase activity (e.g., degrading agarose and agarooligosaccharides to neoagarobiose); biological activity of Aga16B polypeptides include carbohydrate binding and degrading agar and agarose to agarooligosaccharides.

"Substantially preserved activity" means that a polypeptide has at least 10% the activity of a wild-type polypeptide when tested in parallel in a biological buffer at an appropriate temperature and for a sufficient time for the reaction to proceed for the wild-type polypeptide with any suitable substrate.

PRACTICING THE INVENTION

Aga86E

In a first embodiment, the invention is direct to methods and systems using Aga86E polypeptides and polynucleotides from *S. degradans* 2-40. The Aga86 polypeptide (SEQ ID NO:3) and the corresponding polynucleotide (SEQ ID NO:4) are shown in Tables 3 and 4, respectively.

TABLE 3

Aga86E polypeptide sequence
(GenBank Accession No. ZP 00315657: SEQ ID NO: 3)

Met Ser Val Leu Pro Leu Ala Ala <u>Gly Ala Ala Asp Tyr Val Ile Glu</u>
1           5               10                  15

<u>Ala Glu Asn Phe Val Ala Gln Gly Gly Thr Tyr Val Asp Gly Gln Pro</u>
            20              25                  30

<u>Asn Lys Val Ser Val Tyr Ser Val Asn Gly Ala Thr Ala Ile Asn Tyr</u>
            35              40                  45

<u>Val Asn Arg Ala Asp Tyr Thr Asp Tyr Gln Ile Asn Val Ala Thr His</u>
            50              55                  60

<u>Gly Tyr Tyr Asn Val Gln Tyr Ala Ile Gly Thr Ser Val Ala Ser Gly</u>
65                  70                  75              80

<u>Ala Ala Ile Glu Leu Leu Val Gln Asn Gly Ser Ser Trp Glu Ser Gln</u>
                85                  90              85

<u>Gly Gln Thr Asn Val Pro Val Gly His Trp Asp Ser Phe Gln Pro Leu</u>
                100                 105                 110

<u>Asn Ala Ser His Glu Val Ile Leu Pro Ala Gly Thr Val Asn Leu Arg</u>
                115                 120                 125

<u>Val Tyr Gly Ala Gly Ser Asn Asp Trp Gln Trp Asn Leu Asp Ser Ile</u>

TABLE 3-continued

Aga86E polypeptide sequence
(GenBank Accession No. ZP 00315657: SEQ ID NO: 3)

<u>Ser Leu Thr Leu</u> Glu Ser Ala Ile Asn *Pro Gln Pro Asp Pro Asp Pro*
130                    135                    140

*Asp Pro Ser Pro* Gln Leu Val Lys Thr Glu Ala Glu Ala Phe Asn Ala
145                    150                    155                    160

Gln Ser Gly Thr Phe Ala Asp Gly Gln Pro Thr Pro Val Ser Ile Tyr
                165                    170                    175

Thr Val Asn Gly Lys Thr Ala Ile Asn Phe Val Asn Lys Gly Asp Ala
                180                    185                    190

Val Glu Tyr Asn Leu Val Ala Pro Ala Gly Ser Tyr Ala Leu Lys
        195                    200                    205

Tyr Ser Ile Gly Thr Ser Val Ala Ser Gly Ser Glu Val Glu Phe Phe
210                    215                    220

Val Leu Lys Asn Asn Val Trp Val Ser Gln Gly Lys Thr Pro Val Pro
225                    230                    235                    240

Ala Val Gly Trp Asp Asn Phe Thr Ser Val Ala Ser Ala Gln Thr Val
        245                    250                    255

Glu Leu Ala Ala Gly Ser Asn Lys Val Lys Leu Val Gly Ala Gly Thr
260                    265                    270

Asn Asp Trp Gln Trp Asn Leu Asp Phe Phe Glu Leu Thr Leu Gly Asn
        275                    280                    285

Val Glu <u>Pro Glu Pro Glu Pro Glu Pro Glu Pro Glu Pro Glu Pro Glu</u>
290                    295                    300

<u>Pro Glu Pro Glu Pro Glu Pro Glu Pro Glu Pro Glu Pro Glu Pro Glu</u>
305                    310                    315                    320

<u>Pro Glu</u> Pro Gln <u>Pro Glu</u> Pro Asp Gly Asp Pro Val <u>Pro Val Ser Gly</u>
                325                    330                    335

<u>Ser Phe Lys Leu Glu Ala Glu His Phe Gln Lys Val Gly Gly Glu Val</u>
                340                    345                    350

<u>Gln Ile Tyr Ser Leu Ser Pro Gly Asn Ala Val Asn Tyr Phe Asn Ser</u>
355                    360                    365

<u>Gly Asp Tyr Leu Glu Phe Tyr Val Asp Leu Asp Ala Gly Gly Leu Tyr</u>
        370                    375                    380

<u>Glu Ala Ser Phe Arg Val Gly Thr Gly Val Ala Ser Asp Val Ala Val</u>
385                    390                    395                    400

<u>Gly Leu Met Val Thr Asp His Lys Gly Asp Leu Thr Leu Lys Ser Val</u>
                405                    410                    415

<u>Thr Pro Val Thr Asp Gln Gly Gly Trp Asp Ala Phe Tyr Asn Leu Thr</u>
        420                    425                    430

<u>Ala Gln Ser Gln Leu Asn Ile Tyr Ser Gly Ile Asn Thr Ile Arg Ile</u>
435                    440                    445

<u>Thr Gly Ala Gly Ser Ala Asp Phe Gln Phe Asn Ile Asp Ser Ile Thr</u>
450                    455                    460

<u>Leu Thr Arg</u> Val Gly Pro Ile Asn Pro Ala Leu Asp Gly Asp Asn Asp
465                    470                    475                    480

Gly Val Pro Asp Thr Ser Asp Asn Cys Pro Ser Ser Pro Ala Asn Glu
        485                    490                    495

Thr Ala Asn Ala Glu Gly Cys Val Pro Ser Gln Leu Asp Thr Asp Glu
                500                    505                    510

Asp Gly Ile Asn Asp Lys Ile Asp Gln Cys Asp Ala Thr Pro Ala Gly
        515                    520                    525

530                    535                    540

TABLE 3-continued

Aga86E polypeptide sequence
(GenBank Accession No. ZP 00315657: SEQ ID NO: 3)

Asp Phe Val Asp Ala Leu Gly Cys Thr Ser Thr Gly Gly Asp Asp
545                 550                 555                 560

Asp Phe Asp Gly Val Leu Asn Gly Ala Asp Gln Cys Gly Asn Thr Pro
                565                 570                 575

Tyr Gly Met Asn Val Asn Ala Gln Gly Cys Ser Val Phe Ser Gly Ser
            580                 585                 590

Asp Ala Asp Asn Asp Gly Val Ala Asn Ser Glu Asp Thr Cys Ala Asn
        595                 600                 605

Thr Pro Ala Leu Glu Phe Ala Asn Glu Gln Gly Cys Ser Ser Ser Gln
    610                 615                 620

Val Ala Asn Thr His Val Val Asn *Val Ser Val Asn Ala Asn Phe Lys*
625                 630                 *635                 640*

*Arg Ser Val Asn Gly Val Phe Asp Phe Gly Arg Arg His Met Thr*
                *645                 650                 655*

*Ala His Thr Ala Ile His Glu Pro Asp Trp Val Gly His Thr Asp Lys*
            *660                 665                 670*

*Leu Asn Tyr Leu Phe Asn Thr Leu Asp Val Tyr Met Gly Arg Asp Asn*
        *675                 680                 685*

*Gly Ser Ala Thr Trp Lys Phe Asn Asp Thr Thr Glu Asp Pro Asn Lys*
    *690                 695                 700*

*Pro Asn Trp Pro Asn Met Asp Tyr Met Val Glu Arg Gly Lys Gly Leu*
*705                 710                 715                 720*

*Arg Glu Ala His Asp Gln Asn Pro Leu Phe Lys Arg Phe Ser Ala Glu*
                *725                 730                 735*

*Lys Gln Leu Leu Ile Ala Gly Thr Asn Pro His Ala Leu Tyr Pro Thr*
            *740                 745                 750*

*Leu Ser Trp Phe Pro Asn Ala Phe Thr Trp Ser Gly Trp Gln Pro Lys*
        *755                 760                 765*

*Asn Ile Glu Thr Ser Ala Ala Trp Val Gly Gln Tyr Met Glu His Tyr*
    *770                 775                 780*

*Phe Ala Asn Ala Ser Asn Gly Tyr Val Gly Glu Gln Leu Pro Glu Tyr*
*785                 790                 795                 800*

*Trp Glu Val Val Asn Glu Pro Asp Met Lys Met Lys Thr Gly Gln Phe*
                *805                 810                 815*

*Met Val Thr Asn Gln Glu Ala Ile Trp Glu Tyr His Asn Leu Val Ala*
            *820                 825                 830*

*Gln Glu Ile Arg Asp His Leu Gly Ala Glu Ala Pro Pro Ile Gly Gly*
        *835                 840                 845*

*Met Thr Trp Gly Gln His Asp Phe Tyr Arg Arg Asp Gly Ile Ser Arg*
    *850                 855                 860*

*Phe Ala Asp Asp Ser Tyr Asp Gln Trp Ile Thr Asn Asp Asp Gln Val*
*865                 870                 875                 880*

*Leu Gln Ala Glu Ala Arg Ala Phe Tyr Arg Asn Ala Met Ala Thr Thr*
                *885                 890                 895*

*Val Asp Asp Thr Arg Asp Gln Asp Trp Tyr Gln Trp Asp Val Met Trp*
            *900                 905                 910*

*Lys Gly Phe Met Asp Ala Ala Gly Asp Asn Met Asp Phe Tyr Ser Val*
        *915                 920                 925*

*His Ile Tyr Asp Trp Pro Gly Glu Asn Val Gly Asp Thr Thr Val Val*
    *930                 935                 940*

*Arg Arg Gly Gly His Thr Ser Ala Met Leu Glu Met Met Glu Trp Tyr*
*945                 950                 955                 960*

TABLE 3-continued

Aga86E polypeptide sequence
(GenBank Accession No. ZP 00315657: SEQ ID NO: 3)

Asp Val Lys Arg Asn Gly Phe Asn Asn Arg Lys Pro Ile Val Leu Ser
           965                          970                         975

Glu Tyr Gly Ser Val Asn Gly Ala Trp Asp Asn Arg Ala His Glu Glu
           980                          985                         990

Arg Tyr Asp Ile Ala Ser Ile Lys Ala Phe Asn Gly Met Leu Met Gln
           995                         1000                       1005

Phe Leu Glu Arg Pro Asp Tyr Val Ile Lys Ser Leu Pro Phe Thr
          1010                       1015                      1020

Pro Ala Lys Pro Leu Trp Gly Tyr Leu Pro Gly Gly Cys Gly Tyr
          1025                       1030                      1035

Asp Asp Ala Val Ala Cys Thr Thr Arg Tyr His Tyr Ala Met Leu
          1040                       1045                      1050

Ile Glu Asp Glu Leu Asn Ser Gly Asn Trp Glu Trp Ser Ser Tyr
          1055                       1060                      1065

Ile Lys Phe Tyr Glu Leu Trp Ala Asp Ile Asp Gly Thr Arg Val
          1070                       1075                      1080

Asp Ser Lys Ser Ser Asp Val Asp Val Gln Val Asp Ser Tyr Val
          1085                       1090                      1095

Lys Gly Asn Glu Leu Phe Val Ile Leu Asn Asn Leu Glu Ala Ala
          1100                       1105                      1110

Asp Thr Thr Val Asn Leu Asp Val Ser Gly Ile Ala Ser Val Gln
          1115                       1120                      1125

Asn Val Glu Leu Arg Asn Met His Phe Asp Ile Gln Glu Thr His
          1130                       1135                      1140

Leu Asp Arg His His Met Ser Ala Ala Pro Lys Thr Val Thr Leu
          1145                       1150                      1155

Ala Ala Asp Ala Thr Val Val Leu Arg Tyr Thr Leu Ala Ser Ser
          1160                       1165                      1170

Val Ala Val Asn Asn Thr Val Val Glu Lys Lys Tyr Phe Gly Glu
          1175                       1180                      1185

Ser Val Ser Gly Gly Ile Glu Pro His Arg Ile Ser Val Ala Gly
          1190                       1195                      1200

Gly Ala Lys Thr Leu Tyr Ile Asn Asn Val Ser Val Pro Ser Gly
          1205                       1210                      1215

Tyr Ser Glu Ala Ile Leu Arg Leu Thr Val Ser Leu Tyr Pro Asp
          1220                       1225                      1230

Glu Asp Asp Lys Val Gly Gly His Leu Ser Leu Asp Ser Ile Thr
          1235                       1240                      1245

Val Asn Gly Thr Ala Ile Glu Ala Pro Ile Asp Trp Lys Gly Pro
          1250                       1255                      1260

Lys Ala Asn Arg Ala Glu Arg Phe Phe Gly Val Leu Asp Ile Pro
          1265                       1270                      1275

Val Pro Val Glu Leu Leu Gln Ser Thr Asn Thr Ile Ala Val Asp
          1280                       1285                      1290

Phe Arg His Asn Gly Glu Leu Thr Val Ala Asn Leu Ile Val Ser
          1295                       1300                      1305

Glu Phe Thr Ser Glu Pro Asn Arg
          1310                       1315

TABLE 4

| Aga86E polynucleotide sequence (SEQ ID NO: 4) |
|---|

```
atgcgaaatt taaataaaaa taaagtacat atattgcgag cagcaattgc tgcaagcatg     60
agtgtactgc cacttgctgc tggtgccgcc gattatgtaa tcgaagcgga aaactttgtg    120
gcgcagggtg gcacctacgt ggacggacaa cccaataaag ttagcgttta tagtgttaat    180
ggcgcaaccg ctattaacta tgtaaaccga gcagactata ccgattacca aattaatgta    240
gctacccacg gttattacaa tgtgcaatat gctattggta catctgtagc cagtggtgcg    300
gctattgagt tactcgtaca aaatggcagt agctgggaat cgcaggggca acaaatgtg     360 cctgttggtc attgggatag ttttcagcct ttaaatgcaa gtcatgaggt aatcttacct    420
gcgggcactg taaatttacg tgtatatggt gcggggtcta atgattggca atggaattta    480
gattctattt ctctcaccct agagagcgct attaaccctc agcctgatcc agatcccgat    540
cctagccctc aattagtaaa aactgaagcc gaagccttta atgcgcagag cggaactttc    600
gccgatggtc agcctacacc ggtgagtatt tatactgtta atggaaaaac ggcgataaac    660
tttgtaaaca aggcgatgc cgttgaatac aacttagttg ctccggctgc cggttcatac    720
gcattaaaat actctattgg taccagtgtt gcttccggta gtgaagtaga gttttttgtt    780
ttaaaaaata atgtttgggt ttcacagggt aaaacacctg tgccggctgt tggttgggat    840
aactttacct ctgttgccag tgcgcaaacc gttgagttag ctgctggctc aaataaagtt    900
aaacttgttg gtgctggcac taatgactgg cagtggaatt tagatttctt cgagctcacc    960
ctgggaaatg ttgaaccaga accagaacca gaaccagagc cagaaccaga gccagagcca   1020
gagccagagc cagagccaga gccagagcca gaaccagagc cagaaccaga acctcagcca   1080
gagcccgatg gcgaccccgt tcctgtaagt ggctcgttta agttagaagc cgagcacttt   1140
caaaaggtag gtggcgaagt acaaatttat tctctatcgc caggcaacgc ggttaattat   1200
tttaacagcg gtgattacct agagttctat gtcgacttag atgcaggcgg tttgtatgaa   1260
gccagcttca gagtgggtac tggtgtggcc tctgatgtag ccgttggcct aatggttaca   1320
gatcacaaag gtgacttaac attgaagagt gttacacccg taacggatca aggtggttgg   1380
gatgcatttt ataatctcac cgcgcaaagc cagctgaata tttatagtgg tataaacact   1440
attcgtatta caggtgcagg gtctgctgat tttcaattta atattgatag catcactttg   1500
actcgtgttg ggccaattaa cccagcgcta gatggggata acgatggtgt accagataca   1560
```

TABLE 4-continued

Aga86E polynucleotide sequence (SEQ ID NO: 4)

```
tcagataact gcccaagtag ccccgccaat gaaacggcaa acgctgaagg ttgtgtaccg
1620 tcgcaattag acactgatga agatggtatt aacgataaaa ttgatcaatg cgatgcaaca
1680 ccagcaggag attttgttga cgccttaggt tgtacaagta ctggtggtga cgacgatgac
1740 tttgatggcg ttttaaacgg tgccgatcaa tgtggtaata cgccttacgg tatgaacgtt
1800 aatgcccaag ggtgtagtgt gttttctgga agcgatgccg ataacgacgg tgttgcaaac
1860 agcgaagaca cctgcgcaaa tacgcctgcg ttagaattcg ctaacgaaca gggttgttct
1920 tcgtcgcaag tggcaaatac acatgttgtt aacgtaagtg ttaatgctaa ctttaagcgc
1980 tctgtaaatg gtgtatttga tttcggccgc cgtcgtcaca tgactgctca cacggctatt
2040 cacgagccag attgggtagg gcataccgat aagttaaatt acctattcaa caccctagat
2100 gtttacatgg ggcgtgataa cggttcggca acgtggaagt taacgacac taccgaagat
2160 cctaataagc ccaactggcc aaatatggac tacatggttg agcgcggtaa agggttgcga
2220 gaagcgcatg accaaaaccc attgttcaaa cgttttagtg ccgaaaaaca attattaatt
2280 gccggtacta acccgcacgc gttgtaccct accttaagtt ggttccctaa cgcgtttacc
2340 tggagcggtt ggcagcctaa aaatattgaa acatctgcag catgggtggg acagtatatg
2400 gagcattatt ttgcgaacgc ttcaaacggc tatgtaggtg agcagctgcc cgagtattgg
2460 gaagtagtaa acgaaccgga tatgaaaatg aaaaccggtc agtttatggt aaccaatcaa
2520 gaggccatct gggagtacca caacttggtt gcgcaagaaa ttcgcgatca ccttggcgca
2580 gaagcacctc ccattggtgg tatgacttgg ggacagcacg acttctatcg tcgcgatggc
2640 atttcgcgtt ttgccgatga ctcttacgat cagtggatta caaacgatga ccaagtattg
2700 caggcagaag ctcgcgcttt ttatcgcaat gctatggcta ccactgtaga tgatactcgc
2760 gaccaagatt ggtatcagtg ggatgtaatg tggaaaggct ttatggatgc ggccggcgac
2820 aacatggact tttactctgt gcacatttat gactggccag gagagaatgt tggtgatact
2880 actgttgttc gtcgtggtgg gcacacctct gccatgctag aaatgatgga gtggtacgat
2940 gtaaaacgta acggctttaa caaccgtaaa ccaatcgtac tttcggagta cggctcagtt
3000 aatggggctt gggataatcg cgcccacgaa gagcgttacg atattgcaag tatcaaagcg
3060 tttaatggca tgttaatgca gttcctagag cgcccagact acgtaataaa atctctacca
3120
```

TABLE 4-continued

Aga86E polynucleotide sequence (SEQ ID NO: 4)

```
tttactcctg ccaaaccttt gtggggctac ctgcctggtg gttgtggcta cgatgatgca
3180 gtggcctgta ctactcgtta ccattacgcc atgttaattg aggatgagct caacagtggt
3240 aattgggaat ggtcttctta cataaagttc tacgagttgt gggcagatat agacggcact
3300 cgtgtcgatt ctaaatcgtc tgatgtggat gtacaggttg actcttatgt gaaaggtaac
3360 gagctgttcg ttattcttaa caacttagaa gcggccgaca caacggtcaa ccttgatgta
3420 agcggtatag ccagcgtgca aaatgttgaa ttgcgcaaca tgcatttcga tattcaagag
3480 acgcatcttg atcgccatca tatgagcgct gcacctaaaa cggttactct agccgccgat
3540 gcgactgtgg tattacgtta tacgcttgca agcagtgttg cggtaaataa caccgtagta
3600 gagaaaaagt actttggtga gagtgtaagt ggcggtatag aaccacatcg catttcggtt
3660 gcaggcggtg ctaaaacgct ttatatcaat aacgtttcgg ttccaagtgg ctacagcgaa
3720 gcaatattgc gcttaactgt atcgctttac ccagacgaag acgataaagt gggcggccat
3780 ttaagcctag atagcattac tgttaacggc actgccatag aggcgccaat agattggaaa
3840 ggcccgaaag caaaccgtgc agaacgattc ttcggcgtac ttgatattcc agtacctgta
3900 gaattattgc aatctactaa taccatcgca gtggacttcc gccacaatgg tgagttaacg
3960 gtagcaaact taattgtgtc ggaatttact tctgagccaa atagataa
4008
```

Any derivatives of Aga86E can be used in the invention, provided that the catalytic activity of the polypeptide is substantially preserved (e.g., the polypeptide has at least 10% the activity per polypeptide of wild-type Aga86E in phosphate buffer at 42° C. for 1 hour with any suitable substrate, such as agarose or agarooligosaccharides).

The wild-type Aga86E has three carbohydrate binding modules (CBM6s) located in the amino-terminus of Aga86E as follows: CBM6-E1, aa 9 to 148 (SEQ ID NO:5), CBM6-E2, aa 162 to 302 (SEQ ID NO:6), and CBM6-E3, aa 349 to 483 (SEQ ID NO:7); these are underscored once in Table 3. A repetitive linker sequence of (P-X) separate the first and second CBM6 of Aga86E (italicized in Table 3; SEQ ID NO:8, wherein X is any amino acid); the second and third CBM6 are separated by an (E-P) repeat (SEQ ID NO:13; double-underscored in Table 3). Aga86E also has four thrombospondin type 3 repeats between aa 511 and 643. A cleavable type II secretion signal is located at the amino terminus.

A glycoside hydrolase-like domain is found from aa 633 to 1316 aa (single underscored and italicized; SEQ ID NO:9); this domain harbors the catalytic activity of the Aga86E polypeptide.

Thus, in one embodiment, the invention utilizes a polypeptide comprising SEQ ID NO:9. In another embodiment, the invention utilizes a polypeptide comprising SEQ ID NO:9 and at least one CBM, comprising at least one selected from the group consisting of SEQ ID NOs:5, 6 and 7. In yet other embodiments, the invention uses a polypeptide comprising SEQ ID NO:9 and at least two CBMs, wherein the CBMs are separated by a plurality of repeat sequences of SEQ ID NO:8 and/or SEQ ID NO:13, wherein the number of repeats can be, in any combination of SEQ ID NOs:8 and 9: 1, 2, 3, 4, 5, 6, 7, 8, 9, 10, 11, 12, 13, 14, 15, 16, 17, 18, 19, 20, 25, 30, 40, 50 or more. In another embodiment, the invention exploits the full-length Aga86E polypeptide (SEQ ID NO:3).

The invention is also directed to methods and systems using Aga16B polypeptides and polynucleotides from *S. degradans* 2-40. The Aga16B polypeptide (SEQ ID NO:1) and the corresponding polynucleotide (SEQ ID NO:2) are shown in Tables 5 and 6, respectively.

TABLE 5

| Aga16B polypeptide |
|---|

Met Arg Pro Ser Cys Ala Phe Phe Ser Thr Pro Leu Met Ala Ala Asp
1               5                       10                  15

Trp Asp Gly Ile Pro Val Pro Ala Asp Pro Gly Asn Gly Asn *Thr Trp*
            20                  25                  30

*Glu Leu Gln Ser Leu Ser Asp Asp Phe Asn Tyr Ala Ala Pro Ala Asn*
        35                  40                  45

*Gly Lys Arg Thr Thr Phe Tyr Ser Arg Trp Ser Glu Gly Phe Ile Asn*
    50                  55                  60

*Ala Trp Leu Gly Pro Gly Gln Thr Glu Phe Tyr Gly Pro Asn Ala Ser*
65              70                  75                      80

*Val Glu Gly Gly His Leu Ile Ile Lys Ala Thr Arg Lys Pro Gly Thr*
                85                  90                  95

*Thr Gln Ile Tyr Thr Gly Ala Ile His Ser Asn Glu Ser Phe Thr Tyr*
            100                 105                 110

*Pro Leu Tyr Leu Glu Ala Arg Thr Lys Ile Thr Asn Leu Thr Leu Ala*
        115                 120                 125

*Asn Ala Phe Trp Leu Leu Ser Ser Asp Ser Thr Glu Glu Ile Asp Val*
    130                 135                 140

*Leu Glu Ser Tyr Gly Ser Asp Arg Ala Thr Glu Thr Trp Phe Asp Glu*
145             150                 155                 160

*Arg Leu His Leu Ser His His Val Phe Ile Arg Gln Pro Phe Gln Asp*
                165                 170                 175

*Tyr Gln Pro Lys Asp Ala Gly Ser Trp Tyr Pro Asn Pro Asp Gly Gly*
            180                 185                 190

*Thr Trp Arg Asp Gln Phe Phe Arg Ile Gly Val Tyr Trp Ile Asp Pro*
        195                 200                 205

*Trp Thr Leu Glu Tyr Tyr Val Asn Gly Glu Leu Val Arg Thr Val Ser*
210             215                 220

*Gly Pro Glu Met Ile Asp Pro Tyr Gly Tyr Thr Asn Gly Thr Gly Leu*
225             230                 235                 240

*Ser Lys Pro Met Gln Val Ile Phe Asp Ala Glu His Gln Pro Trp Arg*
            245                 250                 255

*Asp Glu Gln Gly Thr Ala Pro Pro Thr Asp Ala Glu Leu Ala Asp Ser*
        260                 265                 270

*Ser Arg Asn Gln Phe Leu Ile Asp Trp Val Arg Phe Tyr Lys Pro Val*
    275                 280                 285

*Ala* Ser Asn Asn Gly Gly Gly Asp Pro Gly Asn Gly Gly Thr Pro Gly
290                 295                 300

Asn Gly Gly Ser Gly Asp Thr Val Val Val Glu Met Ala Asn Phe Ser
305                 310                 315                 320

Ala *Thr Gly Lys Glu Gly Ser Ala Val Ala Gly Asp Thr Phe Thr Gly*
            325                 330                 335

*Phe Asn Pro Ser Gly Ala Asn Asn Ile Asn Tyr Asn Thr Leu Gly Asp*
        340                 345                 350

*Trp Ala Asp Tyr Thr Val Asn Phe Pro Ala Ala Gly Asn Tyr Thr Val*
    355                 360                 365

*Asn Leu Ile Ala Ala Ser Pro Val Thr Ser Gly Leu Gly Ala Asp Ile*
370                 375                 380

*Leu Val Asp Ser Ser Tyr Ala Gly Thr Ile Pro Val Ser Ser Thr Gly*
385             390                 395                 400

*Ala Trp Glu Ile Tyr Asn Thr Phe Ser Leu Pro Ser Ser Ile Tyr Ile*
            405                 410                 415

TABLE 5-continued

| Aga16B polypeptide |
| --- |
| Ala Ser Ala Gly Asn His Thr Ile Arg Val Gln Ser Ser Gly Gly Ser
                420                 425                 430 |
| Ala Trp Gln Trp Asn Gly Asp Glu Leu Arg Phe Thr Gln Thr Asp Ala
                435                 440                 445 |
| Asp Thr Gly Thr Asn Pro Pro Ser Thr Ala Ser Ile Ala Val Glu Ala
                450                 455                 460 |
| Glu Asn Phe Asn Ala Val Gly Gly Thr Phe Ser Asp Gly Gln Ala Gln
465                 470                 475                 480 |
| Pro Val Ser Val Tyr Thr Val Asn Gly Asn Thr Ala Ile Asn Tyr Val
                485                 490                 495 |
| Asn Gln Gly Asp Tyr Ala Asp Tyr Thr Ile Ala Val Ala Gln Ala Gly
                500                 505                 510 |
| Asn Tyr Thr Ile Ser Tyr Gln Ala Gly Ser Gly Val Thr Gly Gly Ser
                515                 520                 525 |
| Ile Glu Phe Leu Val Asn Glu Asn Gly Ser Trp Ala Ser Lys Thr Val
                530                 535                 540 |
| Thr Ala Val Pro Asn Gln Gly Trp Asp Asn Phe Gln Pro Leu Asn Gly
545                 550                 555                 560 |
| Gly Ser Val Tyr Leu Ser Ala Gly Thr His Gln Val Arg Leu His Gly
                565                 570                 575 |
| Ala Gly Ser Asn Asn Trp Gln Trp Asn Leu Asp Lys Phe Thr Leu Ser
                580                 585                 590 |
| Asn |

TABLE 6

| Aga16B polynucleotide (SEQ ID NO: 2) |
| --- |
| atgcgcccta gctgcgcctt cttcagtacc cctcttatgg ctgcagattg ggacggaatt
 60 |
| cctgtcccag cggacccagg gaatggcaac acctgggagc tacagtccct ttctgacgat
 120 |
| ttcaactatg cggccccagc taacggcaaa cgcaccacct tctatagccg ctggagcgaa
 180 |
| ggctttatca atgcttggct cggcccgggg caaaccgagt tttacggccc caatgcttcg
 240 |
| gtagaaggcg gccaccttat tattaaggcc actcgcaagc caggtactac tcaaatttac
 300 |
| actggagcaa ttcactccaa tgaaagtttt acctacccat gtatttgga agcgcgcacc
 360 |
| aaaattacaa acctcaccct cgccaacgca ttttggctac taagctcaga ttccaccgaa
 420 |
| gagattgatg tgctggagtc ttacggcagc gaccgtgcaa cagaaacgtg gtttgacgaa
 480 |
| cgcctacact taagccatca cgttttatc cgccagccat ttcaagacta ccaaccgaaa
 540 |
| gatgcaggca gctggtaccc caaccccgat ggcggcactt ggcgcgacca ttttttccgt
 600 |
| ataggtgttt attggataga cccatggaca ctggagtatt acgtgaatgg cgaattagtg
 660 |
| cgcactgtaa gcggcccaga aatgattgac ccgtacggtt acaccaacgg cacaggccta
 720 |

TABLE 6-continued

Aga16B polynucleotide (SEQ ID NO: 2)

```
agtaaaccca tgcaagttat tttcgatgca gagcatcagc cttggcgcga cgaacaaggt
780 actgccccac ccaccgacgc agagctagcc gactcgagtc gcaatcaatt cttaattgac
840 tgggtgcgat tctacaaacc cgtggcaagc aacaatggtg gcggcgaccc aggcaatggc
900 ggcaccccag gtaatggtgg cagtggcgat actgtagtgg tagaaatggc caacttctct
960 gccacaggta aagaaggctc tgcagttgca ggcgacactt tcacaggctt caacccagc
1020 ggcgcgaaca acatcaacta caacaccttt ggggattggg cagactacac ggtgaacttc
1080 cccgctgccg gtaattacac cgtaaaccta attgcagcct cgccggttac atctgggctg
1140 ggtgcagata ttttggtaga cagcagttac gcaggcacca tacctgttag cagcaccgga
1200 gcttgggaga tatacaacac ctttagcttg cccagctcga tttatatcgc aagcgcaggc
1260 aatcatacta ttcgcgtaca aagctccggc ggtagcgctt ggcagtggaa cggcgacgaa
1320 cttcgcttta cccaaacgga tgcggataca ggcaccaatc cacccagtac agccagcata
1380 gcggttgaag ccgaaaactt taacgcggtg ggcggcacct ttagcgatgg tcaagctcaa
1440 cctgttagcg tttacaccgt taacggcaac actgccatta actacgtaaa ccaaggcgat
1500 tatgccgact acaccattgc tgttgcccaa gcgggtaact acaccattag ctatcaagct
1560 ggcagtggcg taacaggtgg tagcatagag tttttggtta acgaaaacgg aagctgggcc
1620 agtaaaaccg ttaccgccgt accaaaccaa ggttgggata acttccaacc cttaaacgga
1680 ggcagcgttt acctaagcgc aggcacccac caagttcgtt tacacggcgc tggcagcaac
1740 aactggcagt ggaacctaga taagttcacg cttagcaact aa
1782
```

Any derivatives of Aga16B can be used in the invention, provided that the catalytic activity of the polypeptide is substantially preserved (e.g., the polypeptide has at least 10% the activity per polypeptide of wild-type Aga16B in phosphate buffer at 42° C. for 1 hour with any suitable substrate, such as agar or agarose).

The wild-type Aga16B has two CBM6s located in the carboxy-terminus of Aga16B as follows: CBM6-B1, aa 322 to 445 (SEQ ID NO:10), and CBM6-B2, aa 455 to 593 (SEQ ID NO:11); these are underscored once in Table 5.

A glycoside hydrolase-like domain is found from aa 31 to 289 (single underscored and italicized; SEQ ID NO:12); this domain harbors the catalytic activity of the Aga16B polypeptide.

Thus, in one embodiment, the invention utilizes a polypeptide comprising SEQ ID NO:12. In another embodiment, the invention utilizes a polypeptide comprising SEQ ID NO:12 and at least one CBM, comprising at least one selected from the group consisting of SEQ ID NOs:10 and 11. In another embodiment, the invention exploits the full-length Aga16B polypeptide (SEQ ID NO:1).

The two catalytic domains of Aga86E and Aga16B can be fused into a single polypeptide. Thus in yet another embodiment, the invention utilizes a polypeptide comprising SEQ ID NO:9 and SEQ ID NO:12. In a further embodiment, the invention utilizes a polypeptide comprising SEQ ID NOs:9 and 12 along with at least one CBM selected from the group consisting of SEQ ID NOs:5, 6, 7, 10, and 11. The CBMs can be separated from each other with any number of repeats of SEQ ID NOs:8 and 13, including 1, 2, 3, 4, 5, 6, 7, 8, 9, 10, 11, 12, 13, 14, 15, 16, 17, 18, 19, 20, 25, 30, 40, 50 or more sets of repeats. Noteworthy, too, is that the catalytic domain of Aga86E (SEQ ID NO:9) can be combined with any CBM (SEQ ID NOs:5, 6, 7, 10 and 11), which CBMs can be separated by any number of repeats, such as 1, 2, 3, 4, 5, 6, 7, 8, 9, 10, 11, 12, 13, 14, 15, 16, 17, 18, 19, 20, 25, 30, 40, 50 or more sets of repeats of SEQ ID NOs:8 and 13, while the Aga16B catalytic domain (SEQ ID NO: 12) is absent.

Substrates

In one embodiment of the invention, at least one polypeptide having a catalytic activity is contacted with a suitable substrate. The substrate is selected from the group consisting of agar, agarose, neoagarotetraose, agarooligosaccharides, and derivatives thereof. Derivatives include partially cross-linked molecules, substituted molecules, and the like. In some embodiments, the substrates can be molten.

In some embodiments, the ultimate product of contacting a substrate with a polypeptide having catalytic activity is neoagarobiose (formula T), shown below. Neoagarobiose is a disaccharide of β-D-galactose and 3,6-anhydro-α-L-galactose, which when linked together, constitutes agarose. In one embodiment, an Aga86E polypeptide is contacted with agarose or an agarooligosaccharide to produce neoagarobiose. In another embodiment, agar or agarose is contacted with an Aga16B polypeptide, to produce mixed-length agarooligosaccharides; these agarooligosaccharides are then contacted with an Aga86E polypeptide to produce from exolytic cleavage, neoagarobiose.

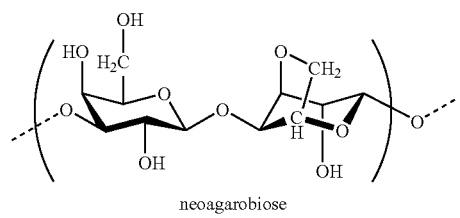

neoagarobiose (I)

Making Aga86E/16B polypeptides

The invention is directed to using Aga86E/16B polypeptides, and biologically-active portions, derivatives, fragments, analogs or homologs thereof. Aga86E/16B polypeptides can be isolated from cells and tissues, produced by recombinant DNA techniques or chemically synthesized.

An Aga86E/16B "chimeric polypeptide" or "fusion polypeptide" comprises Aga86E/16B fused to a non-Aga86E/16B polypeptide, or fused with various combinations of CBM6 and GH86 or GH16 domains. A non-Aga86E/16B polypeptide is not substantially homologous to Aga86E/16B (SEQ ID NOS:1, 3, 5, 6, 7, 9-12). An Aga86E/16B fusion polypeptide can include any portion to an entire Aga86E/16B, including any number of biologically active portions.

Other fusion partners can aid in purify Aga86E/16B polypeptides, such as Histidine tags, and for linking to solid supports, such as nickel-coated supports.

Fusion polypeptides can be easily created using recombinant methods. A polynucleotide encoding Aga86E/16B can be fused in-frame with a non-Aga86E/16B encoding polynucleotide, to the Aga86E/16B N- or C-terminus, or internally. Fusion genes can also be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel et al., 1987).

Any vector can be used, including plasmids, viral vectors, etc. Recombinant expression vectors that comprise a Aga86E/16B (or fragment(s)) regulate a Aga86E/16B transcription by exploiting one or more host cell-responsive (or that can be manipulated in vitro) regulatory sequences that is operably-linked to Aga86E/16B.

Vectors can be introduced in a variety of organisms and cells, which methods, organisms and cells are well-known to those of skill in the art. Alternatively, the vectors can be transcribed and translated in vitro, for example, using T7 promoter regulatory sequences and T7 polymerase.

Solid Supports

In some embodiments, the Aga86E/16B polypeptides are linked to solid supports. The advantage of this approach is that the Aga86E/16B polypeptides can easily be removed from the reaction mix, essentially purifying the resulting products, such as neoagarobiose.

The solid support can be any material known to those of ordinary skill in the art to which the polypeptides can be attached. For example, the solid support can be a test well in a microliter plate or a nitrocellulose or other suitable membrane. Alternatively, the support can be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent can be immobilized on the solid support using a variety of techniques known to those of skill in the art, which are amply described in the patent and scientific literature. "Immobilization" refers to both noncovalent association, such as adsorption, and covalent attachment (that can be a direct linkage between the agent and functional groups on the support or can be a linkage by way of a cross-linking agent). In such cases, adsorption can be achieved by contacting the binding agent, in a suitable buffer, with the solid support for a suitable amount of time. Such binding should not interfere with the ability of the bound polypeptide to carry out its function, whether to cleave a polysaccharide or bind carbohydrates. Alternatively, the polypeptides can be bound to microparticles that have previously been coated with streptavidin (or avidin) or biotin. Alternatively, the polypeptides can be bound using microparticles that have been previously coated with anti-Aga86E/16B antibodies or derivatives thereof. Moreover, the solid support can be derivatized to allow reactivity with various functional groups on the polypeptides. Such derivatization requires the use of certain coupling agents such as maleic anhydride, N-hydroxysuccinimide and 1-ethyl-3-(3-dimethylaminopropyl)carbodiimide. Many useful coupling agents are currently available from Pierce Biotechnology, Inc. (Thermo Scientific; Rockford, Ill.).

Substrate Degradation

The methods of the invention include contacting a substrate with at least an enzymatically active domain of Aga86E, such as the GH domain of SEQ ID NO:9 or a functional derivative thereof. The digestion of the substrate, especially when the substrate is agar or agarose, can be hastened by the addition of Aga86E CBMs, and further so by the addition of an Aga16B enzymatically active domain (or in some cases, pre-contacting the substrates with a enzymatically active domain of Aga16B, such as that of SEQ ID NO:12 and functional derivatives thereof), and further addition of CBMs particular to Aga16B. In one embodiment, a substrate is contacted with an Aga86E polypeptide of SEQ ID NO:1; in yet another embodiment, the substrate is contacted with Aga86E polypeptide of SEQ ID NO:1 and an Aga16B polypeptide of SEQ ID NO:3. A substrate can be contacted sequentially with Aga16B polypeptides, and the enzymatically-produced products (agarooligosaccharides of various lengths) then contacted with Aga86E polypeptides. It is unnecessary to remove any remaining Aga16B polypeptides from the reaction mix before contacting the reaction mix with an Aga86E polypeptide.

In one embodiment, the polypeptides are linked to solid supports. One solid support may comprise all of the Aga16B/Aga86E polypeptides; in other embodiments, one solid support may comprise only Aga16B polypeptides, and another solid support may comprise only Aga86E polypeptides. In one embodiment, the substrate is first incubated with Aga16B polypeptides linked to solid supports, followed by the addition of Aga86E polypeptides linked to solid supports. Optionally, before adding the Aga86E polypeptide-coated supports, the Aga16B polypeptide-coated solid supports are first removed. Removal can be accomplished by any physical method, such as simple centrifugation, or in the case of magnetic supports, using magnetic fields, or a combination of physical separation methods.

The substrates and Aga86E/16B polypeptides are suspended in solution for the reaction to optimally proceed. In most embodiments, a biological buffer is used; such buffers can maintain desirable pH and other reaction conditions. Any suitable buffer can be used. Examples of suitable biological buffers include Hank's Balanced Salt Solution (HBSS), sodium phosphate-based buffers, N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glyclclycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), and tris(hydroxymethyl)-aminomethane (Tris). Salt solutions that can be used to manipulate osmotic conditions include Alseverr's Solution, Dulbecco's Phosphate Buffered Saline (DPBS), Earle's Balanced Salt Solution, Gey's Balanced Salt Solution (GBSS), Puck's Saline A, Tyrode's Salt Solution, St. Thomas Solution and University of Wisconsin Solution.

In some cases, water alone is sufficient.

The Aga86E/16B polypeptides can be used over a wide range of pH. Optimal pHs are those that are slightly alkaline, such as pH 7.2-8.0. But any pH can be used that does not affect the substrate or polypeptide integrity, such as pH 5, 6, 7, 8, 9, and 10, or any increment therein.

The Aga86E/16B polypeptides are contacted with a substrate, creating a reaction mix, in a buffer for a time sufficient to produce neoagarobiose. The time can vary due to the activity of a particular lot of Aga86E/16B polypeptides, the combination of the various domains used in the reaction mix, the amount of substrate, the type of substrate, the concentration of the enzymatically active domains, etc. Generally, the reaction mix is incubated from 1 minute to 5 days; more typical times include 30 minutes, 60 minutes, 2 hours, 4 hours, 8 hours, 12 hours, 24 hours, etc. The optimal reaction time for a particular production of Aga86E/16B polypeptides, substrates, etc., can easily be determined by one of skill in the art.

Temperature can influence the speed at which the digestion proceeds. In some embodiments, a temperature of approximately 42° C. is desirable. However, other temperatures can be used, from 25° C. to 50° C., such as 25, 26, 27, 28, 29, 30, 31, 32, 33, 34, 35, 37, 40, 42, 45, 47 and 50° C. The temperature can be varied during the incubation time.

In some embodiments, the reaction mix is agitated and/or aerated during substrate digestion.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1

Materials and Methods

Bacterial Strains and Plasmids

*Saccharophagus degradans* 2-40T (ATCC 43961; DSMZ17024; American Type Culture Collection (ATCC); Manassus, Va.) was grown in minimal medium containing (per liter) 2.3% INSTANT OCEAN® (Aquarium Systems, Mentor, Ohio), 0.5% ammonium chloride, and 50 mM Tris-HCl, pH 7.6. Carbon sources were added to a final concentration of 0.2%. Agar (1.5%) was added to solid media. Cultures of *S. degradans* 2-40 were incubated at 28° C. *Escherichia coli* EPI300, DH5α, and Tuner strains were grown at 37° C. in Luria-Bertani (LB) broth or agar supplemented with the appropriate antibiotics. Antibiotics were added to media at the indicated concentrations (in μg/ml): ampicillin, 200; chloramphenicol, 30; and kanamycin (Kan), 50.

Molecular Biology Protocols

DNA manipulations were performed using standard procedures. Restriction enzymes and T4 DNA ligase were obtained from New England Biolabs (Ipswich, Mass.). The pETBlue-2 expression vector was purchased from Novagen (Madison, Wis.). All other reagents and substrates were obtained from Sigma-Aldrich (St. Louis, Mo.) unless otherwise noted. Polymerase chain reactions (PCRs) employed either Taq (Invitrogen, Carlsbad, Calif.) or ProofPro (Continental Lab Products, San Diego, Calif.) polymerase by use of the manufacturer's recommended conditions. The nucleotide sequences of plasmid DNA or gel-purified PCR products were obtained at the UMBI sequencing facility.

Construction and Initial Screen of the *S. degradans* Genomic Library.

Genomic DNA was isolated from *S. degradans* 2-40 by using cetyltrimethylammonium bromide (Sambrook and Russell, 2001). The chromosomal DNA was used to construct a genomic library composed of 40-kb fragments cloned into pCC1Fos (Beta version; Epicentre Technologies, Madison, Wis.) by following the manufacturer's recommendations. The fosmid was packaged into lambda phage and used to transfect *E. coli* EPI300 (Epicentre). A pitting phenotype on LB agar plates was used initially to screen $Cm^r$ transfectants for agarase activity.

Determination of the Nucleotide Sequences of aga50A and aga16B

Sau3A fragments of 5 to 10 kb were ligated into BamHI-digested pUC19 and transformed into *E. coli* DH5α. Random pUC19 derivatives were selected, and a partial DNA sequence of the insert was obtained by using commercially available M13REV and the M13(−21) primers. The nucleotide sequences of candidate agarases were completed by primer walking using synthetic oligonucleotides (Table 7)

TABLE 7

Sequences used in cloning and manipulating agarases

| Primer | Sequence | SEQ ID NO: | Use |
|---|---|---|---|
| aga16B-f | aactgcagatccatgaaaaccacaaatgc | 47 | Cloning of aga16B |
| aga16B-r | ccatcgatcttatctaggttccactgcca | 48 | Cloning of aga16B |
| ga16B968R | ccatcgatacctgtggcagagaagttg | 49 | Truncation of aga16B |
| ga16B853R | ccatcgatgtagaatcgcacccagtcaat | 50 | Truncation of aga16B |
| aga16B736F | cttggcgcgccggcgcgacgaacaaggta | 51 | Truncation of aga16B |
| aga16B1371R | ccatcgaatgtactgggtggattggtg | 52 | Truncation of aga16B |
| aga86E-f | cttggcgcgccgagtcgcttttatcat | 53 | Cloning of aga86E |
| aga86E-r | ccatcgattctatttggctcagaagt | 54 | Cloning of aga86E |
| aga16B767R | ccatcgatgcgccaaggctgatgctgt | 55 | Cloning of aga86E |
| aga86E-CF | ctctcatcaaccgtggcgaggtcggcgcaaactgtca | 56 | Deletion of aga86E |
| aga86E-CR | acacattgcgatagtcacgc | 57 | Deletion of aga86E |
| aga86E-NE | ccgctgcgctgtgagtatc | 58 | Deletion of aga86E |
| aga50A-CF | ctctcatcaaccgtgggcttatttacgcagtgttagg | 59 | Deletion of aga50A |
| aga50A-CR | ctctttcgcgttagcatctaa | 60 | Deletion of aga50A |
| aga50A-NF | cagagccttcttacctgtg | 61 | Deletion of aga50A |
| aga50A-NR | cgatgatggttgagatgtgtttatgtctgatggctaaacga | 62 | Deletion of aga50A |

Bioinformatic Approaches

Protein modules and domains were identified in deduced products by using the Simple Modular Architecture Tool ((Letunic et al., 2006; Schultz et al., 1998), the Pfam database (Finn et al., 2006), and the Carbohydrate-Active enZYme database (Coutinho and Henrissat, 1999a). Similarity searches were performed using the BLAST algorithm at the National Center for Biotechnology Information (NCBI) server (Altschul et al., 1990) or surveys of the S. degradans 2-40 genome (GenBank accession: CP000282). Type II secretion signals were identified using the SignalP version 1.1 program (Bendtsen et al., 2004). Molecular masses of polypeptide products were estimated using the peptide mass tool at the ExPASy server of the Swiss Institute of Bioinformatics (Gasteiger et al., 2005; Wilkins et al., 1997). The annotated genomic sequence of S. degradans 2-40 is Genbank Accession no. CP000282. Sequences were aligned using Clustal W (Thompson et al., 1994) or ClustalX (Thompson et al., 1997). The percent G+C content (% G+C) of whole genes and the % G+C at the third position of synonymous codons (GC3s) were calculated using CodonW (Peden, J. P., 2005; available from Sourceforge (Mountain View, Calif.)). Because a significant number of S. degradans 2-40 genes exhibit high similarity to genes found in diverse taxonomic units, a core set of genes was established to minimize the potential impact of horizontally acquired genes on baseline values. As approximately 20% of S. degradans 2-40 gene models exhibit similarity at the nucleotide level to a gene in a fluorescent pseudomonad (974 genes), most of which are annotated as basic metabolism and housekeeping genes, S. degradans 2-40 genes exhibiting at least 50% identity at the nucleotide level with a Pseudomonas sp. gene were used to calculate baseline % G+C, GC3s, and codon usage patterns. This core gene set included a total of 1,153,863 nucleotides (nt) of sequence data. The core gene set had a % G+C of 46.3, which is slightly higher than the total genome % G+C of 45.8% (Gonzalez and Weiner, 2000).

Zymograms

The samples were fractionated by sodium dodecyl sulfate-polyacrylamide gel electrophoresis (SDS-PAGE) in an 8% polyacrylamide gel supplemented with 0.1% agarose. Gels were then washed twice in 20 ml PIPES-Triton buffer (20 mM PIPES [piperazine-N,N'-bis(2-ethanesulfonic acid)], pH 6.8, and 2.5% Triton X-100) for 20 min at room temperature and then incubated in PIPES-Triton buffer overnight at 4° C. Gels were washed twice with 20 ml PIPES buffer and incubated at 42° C. for 2 h. Agarase activity of S. degradans 2-40 lysates was maximal at 42° C. and was stable at this temperature (Whitehead et al., 2001). Zymograms were developed using Gram's iodine solution.

Protein Expression and Purification

Genes of interest were amplified by PCR using tailed primers (see Table S1 in the supplemental material). Each fragment was digested with the designed restriction enzyme, ligated into pETBlue-2, and transformed into E. coli Tuner or E. coli DH5α cells. A 50-ml culture of each transformant carrying a clone of interest was grown at 37° C. to an optical density at 600 nm of 0.5 and induced with 1 mM (final concentration) isopropyl-β-D-thiogalactopyranoside (TPTG). After growth for 4 h at 37° C., cells were harvested and frozen at −20° C. His fusions were purified from cell lysates by using Ni-nitrilotriacetic acid resin (QIAGEN, Valencia, Calif.) according to the manufacturer's recommendations.

Assay of Agarase Activity and Identification of Reaction Products.

Reactions with purified agarase and agarose were performed in 50-µl reaction mixtures containing an aliquot of the purified His-tagged agarase in phosphate-buffered saline and 5 µl of molten 1% agarose. The reaction mixtures were incubated at 42° C. and then applied to a Whatman silica gel 60 A plate with a 250-µm layer. Neoagarohexaose, neoagarotetraose, neoagarobiose, and D-galactose (5 µg) were used as standards. The plates were developed with 2:1:1 N-butanol: acetic acid:water solution and stained with 2:1 ethanolic sulfuric acid:naphthoresorcinol solution (Duckworth and Yaphe, 1970). Degradation products were visualized by being baked at 80° C. for 10 min.

Mass Spectrometry

Culture filtrates of agarose-grown cells were concentrated about 25-fold by ultrafiltration, and protein concentrations were determined using a bicinchoninic acid protein assay (Pierce). Proteins were denatured by incubation in 100 mM Tris buffer, pH 8.5, containing 8 M urea and 10 mM dithiothreitol, and the denatured proteins were alkylated in 50 mM iodoacetate. The denatured, reduced, alkylated samples were digested overnight at 37° C. by using proteomics-grade trypsin (Promega) at a 1:50 enzyme-to-substrate ratio. Digestions were stopped in 1% formic acid and analyzed by reverse-phase high-pressure liquid chromatography (HPLC)-tandem mass spectrometry (MS) at the UMCP College of Life Sciences Mass Spectrometry facility with a Waters 2960 HPLC system linked to a Finnigan LCQ tandem mass spectrometer. Alternatively, culture supernatants were fractionated on 8% SDS-PAGE gels containing 0.1% agarose and stained with SYPRO Ruby red (Molecular Probes). Regions of interest were excised and were equilibrated with 50% 200 mM ammonium bicarbonate and 50% acetonitrile. The treated samples were submitted to the Stanford University Mass Spectrometry Laboratory for analysis by electrospray ionization-quadrupole time-of-flight MS following trypsin digestion. Identification of peptide fragments employed SEQUEST (Eng et al., 1994) and MASCOT (Perkins et al., 1999) algorithms and the amino acid sequence translations of all gene models in the S. degradans 2-40 genome as well as the nonredundant mass spectrometry database (compiled by Dr. D. N. Perkins; Imperial College School of Medicine; London, UK).

Immunoblots

Proteins were fractionated by SDS-PAGE as described above and electroblotted onto supported nitrocellulose membranes (0.45-mm pore size; Osmotics, Trevose, Pa.). Membranes were blocked with 1% alkali-soluble casein (Novagen) and incubated with rabbit anti-AgaE antibodies (1:100). Membranes were washed twice and incubated with horseradish peroxidase-conjugated donkey anti-rabbit antibody (Amersham). Immunoreactive proteins were visualized using an ECL detection kit (Amersham Pharmacia Biotech).

Marked Chromosomal Gene Replacements

The procedures used to generate gene replacement mutants in an Acinetobacter sp. (Metzgar et al., 2004) were adapted for use with S. degradans 2-40. Briefly, the 1-kb regions upstream and downstream of the gene of interest were amplified from genomic DNA by PCR employing a standard design primer and a splicing primer containing 5' tails complementary to the primers used to amplify a Kan resistance cassette. Aliquots of the upstream- and downstream-region amplicons were mixed directly with an amplified Kan cassette in a splicing PCR mixture containing both standard design primers in excess. After amplification for 30 cycles, the complete splicing PCR mixture was added to a culture of S. degradans 2-40 outgrown from stationary phase in minimal medium plus glucose for 4 h and allowed to incubate with shaking at 28° C. for 2 h. Cells were harvested, washed once in outgrowth medium, and plated onto selective media containing glucose and 100 µg/ml Kan. After 3 to 4 days, cells from appearing colonies were screened in batches for gene replacements by PCR using one of the standard design primers and the correctly oriented primer specific for the kanamycin cassette. Positive colonies were screened with the opposite primer combination to confirm the insertion.

Nucleotide Sequence Accession Numbers

The nucleotide sequences for Aga50A, Aga16B, Aga86C, Aga50D, and Aga86E have been reported to the GenBank database under accession nos. ZP_00315251, AAT67062, ZP_00315652, ZP_00315360, and ZP_00315657, respectively.

Example 2

Predicted Agarases Encoded by S. degradans Genome

Relatively limited genetic tools are available for use in S. degradans 2-40, as stable transformants carrying commonly used narrow- or broad-host-range plasmids could not be isolated and traditional transposon mutagenesis strategies were ineffective. In order to identify agarase-encoding genes, E. coli EPI300 transfectants carrying a genomic library of S. degradans 2-40 created in the copy control fosmid pCC1Fos were screened on solid agar media for a pitting phenotype. Pitting colonies indicative of the hydrolysis of agar were detected at a frequency of $1.7 \times 10^{-3}$ only when cells were grown under single-copy conditions for the fosmid. This was comparable to the expected frequency for a single gene in this library. A total of nine transfectants that pitted agar were identified, and one, EPI300(pNE10), was chosen for sequence analysis. All Aga$^+$ fosmids were highly unstable in several E. coli strains, with less than 1% of transformants retaining an Aga$^+$ phenotype in repeated plasmid isolation/transformation into fresh hosts. The Aga$^+$ colonies were substantially smaller than those of the Aga$^-$ transformants.

Due to the phenotypic instability of the Aga$^+$ fosmids, sequence analysis was used to identify resident agarase genes. The sequence of subcloned fragments of pNE10 revealed two open reading frames that could be involved in the degradation of agar. The first, aga50A, encoded a deduced product of a 776-amino-acid (aa) polypeptide with a predicted molecular mass of 86 kDa that was 45% identical and 62% similar to a putative secreted hydrolase from *Streptomyces coelicolor* A3 (Allouch et al., 2003) (NP627690) and that also exhibits similarity to a β-agarase identified in *Vibrio* sp. strain JT0107 (S46651) (Table 8). The second open reading frame, aga16B, was predicted to encode a 593-aa product with a predicted mass of 64 kDa. The amino-terminal 278-aa region of Aga16B is 54% identical and 69% similar to a β-agarase of *Pseudomonas* sp. strain ND137 (BAD88713) and is 64% identical and 73% similar to a β-agarase from *Microbulbifer* sp. strain JAMB-A7 (BAC99022). aga50A appeared to be divergently expressed from aga16B by a shared 424-bp promoter region. Immediately downstream of aga16B is the gene for a tRNA$^{Ser}$. A PCR screen revealed that aga50A and aga16B were present in all Aga$^+$ *E. coli* EPI300 transfectants carrying the *S. degradans* 2-40 genomic library but were specifically absent from spontaneously arising Aga$^-$ derivatives of pNE10.

TABLE 8

Properties of candidate agarases identified in the *S. degradans* 2-40 genome

| Gene | GenBank accession no. | Size of predicted product (kDa)[a] | Representative homolog[b] | Homolog GenBank accession no. | % S[c] | % I[c] |
|---|---|---|---|---|---|---|
| agaSQA | ZP 0031251 | 87 | β-Agarase of *Vibrio* sp. strain JT0107 | S46651 | 62 | 44 |
| aga16B | AAT67062 | 64 | Agarase of *Pseudomonas* sp. strain ND137 | BAB88713 | 54 | 69 |
| aga86C | ZP 000315652 | 86 | β-Agarase of *Pseudoalteromonas atlantica* | AAA25696 | 38 | 55 |
| aga50D | ZP 000315360 | 89 | β-Agarase of *Vibrio* sp. strain JT0107 | S46651 | 43 | 60 |
| aga86E | ZP 000315657 | 146 | β-Agarase of *Microbulbifer* sp. strain JAMB-A94 | BAD86832 | 60 | 72 |

[a]As estimated by the ExPASy peptide mass tool.
[b]As determined by a BLASTP search of the nonredundant database.
[c]Percent similarity (% S) and percent identity (% I) as calculated by BLASTP alignment.

Upon the release of the *S. degradans* 2-40 genome sequence by the U.S. Department of Energy Joint Genome Institute (Walnut Creek, Calif.), genes for three additional candidate agarases were identified by sequence similarity to known agarases. The first, aga86C, encoded a 789-aa, 86-kDa protein with a domain that shares 38% identity to a β-agarase of *Pseudoalteromonas atlantica* (AAA25696) and 29% identity and 45% similarity to an agarase from *Microbulbifer* sp. strain JAMB-A94 (BAD86832) (Table 2). Aga86C did not share obvious similarity to either Aga50A or Aga16B. A gene for another candidate agarase, aga50D, produced a 795-aa product with a predicted mass of 88.6 kDa. A portion of Aga50D exhibited 45% identity and 61% similarity to a putative secreted hydrolase from *S. coelicolor* (NP627690) and 43% identity and 60% similarity to an agarase from *Vibrio* sp. strain JT0107 (S46651). Aga50D also shared sequence similarity with a domain of the *S. degradans* 2-40 Aga50A. A third putative agarase gene, aga86E, yielded a 1,335-aa, 146-kDa deduced polypeptide. The carboxy-terminal 679-aa region was 30% identical and 44% similar to the β-agarase of *P. atlantica* and also exhibited 29% identity and 44% similarity to a domain of the *S. degradans* 2-40 Aga86C. A homolog to a GH96 domain characteristic of α-agarases was not apparent in the genome.

TABLE 9

Sequence features for gene models predicted to encode agarases

| Gene(s) | Gene model[a] | Chromosomal address[b] | % G + C[c] | GC3s[d] | No. of amino acids with variant codon usage[e] |
|---|---|---|---|---|---|
| Aga50A | 1176 | 1513741-1516074 | 45.3 | 38.6 | 6[f] |
| Aga16B | 1175 | 1513481-1511685 | 52.4 | 52.6 | 6[g] |
| aga86C | 2650 | 3352440-3354803 | 46.8 | 44.8 | 8[h] |
| aga50D | 2644 | 3345735-3343354 | 46.3 | 42.9 | 1[i] |
| aga86E | 2655 | 3369919-3365912 | 46.1 | 37.3 | 7[j] |
| Core genes[k] | | | 46.3 | 42 | |

[a]Gene numbers assigned in the 15 Jun. 2005 annotation of the genome from Genome Analysis and System Modeling Group of the Life Sciences Division of Oak Ridge National Laboratory (Oak Ridge, TN).
[b]Nucleotide address of the apparent coding sequence within the assembled 15 Jun. 2005 version of the *S. degradans* 2-40 genome. The nucleotide address of the deduced start codon is listed first, followed by the address of the last nucleotide of the apparent stop codon.
[c]% G + C calculated for the indicated predicted coding sequence.
[d]% G + C in the third position of synonymous codons within the deduced coding sequence.
[e]A two-tailed Fisher exact analysis of the codon usage for each amino acid with synonymous codons was performed, comparing codon usage within the predicted coding sequence to that within the core gene set. A P value that indicates the probability that the codon usage is the same as that for the core set was generated. The number of amino acids for which the P value was less than 0.1 is shown.
[f]Variant codon usage was detected for Arg, Cys, Gly, His, Pro, and Ser.
[g]Variant codon usage was detected for Asn, Asp, Gly, Phe, Ser, and Tyr.
[h]Variant codon usage was detected for Ala, Asp, Glu, Gly, Leu, Ser, Tyr, and Val.
[i]Variant codon usage was detected for Asp.
[j]Variant codon usage was detected for Arg, Glu, Gly, Pro, Ser, Thr, and Val.
[k]The core gene set represents the 974 genes with at least 50% similarity to a gene in a *Pseudomonas aeruginosa* PAO1 genome.

The putative agarase genes were located in two regions of the *S. degradans* 2-40 genome. Aga50A and aga16B clustered as gene models 1176 and 1175, respectively, located between nucleotides 1511685 and 1516074, in the 15 Jun. 2005 annotation of the *S. degradans* 2-40 genome (Table 9). Flanking aga50A is a gene for a candidate β-galactosidase (galA), but the annotations of other nearby genes did not indicate obvious predicted roles in CP metabolism. The gene models for aga86C (gene model 2650), aga50D (gene model 2644), and aga86E (gene model 2655) loosely cluster in a 26,565-nt region beginning at nucleotide 3343354. Most intervening genes do not appear to be associated with degradation of agar or other CPs, but a candidate sugar transporter is present in this region.

Variation in % G+C and codon usage can indicate acquisition from another organism. Using simple % G+C analysis of the coding sequences, only the aga16B coding sequence differed substantially from that of the core gene set (Table 9). In contrast, the GC3s differed from that of the core set by at least 3% in aga50A, aga16B, aga86C, and aga86E, suggestive of acquisition from another organism. These genes also differed in their codon usage patterns relative to the core set of genes. Using a two-tailed Fisher exact test to statistically compare codon usage of the agarase genes to that of the chosen core gene set (Plotkin et al., 2004), codon usage for at least 6 of the 18 amino acids with synonymous codons had less than a 10% chance of being the same as that for the core set (Table 2). In contrast, aga50D was similar to the core set in all traits evaluated except codon usage for Asp. A survey of the nonredundant databases for nucleotide sequence similarities revealed only localized sequence similarities, located primarily within conserved domains of the agarases. Because four of five agarases present in the *Microscilla* sp. strain PRE1 agarolytic plasmid had extensive similarity to *S. degradans* 2-40 agarases, the *S. degradans* 2-40 genome was surveyed for other similarities with the *Microscilla agarolytic* plasmid. No similarities were detected at the nucleotide level between the agarolytic plasmid of *Microscilla* sp. strain PRE1 and the *S. degradans* 2-40 genome, but extensive similarities (nt 58656 to 62741) to a 3-kb region internal to the aga50D-aga86C-aga86E cluster that exhibited extensive synteny were detected.

Example 3

Modular Structure of the Agarases Encoded by *S. degradans*

Hydrolases typically carry conserved glycoside hydrolase (GH) domains that function in catalysis and sometimes also carry CBMs (Coutinho and Henrissat, 1999b). Although commonly used domain recognition algorithms, such as SMART, did not identify conserved GH domains within the predicted *S. degradans* 2-40 agarases, three distinct GH domains were detected when the localized regions of sequence conservation in Aga16B, Aga50A/Aga50D, and Aga86C/Aga86E were analyzed (FIG. 1). The 120-aa region of Aga16B that shares sequence similarity with seven known β-agarases (aa 31 to 289) contains a GH16 domain (FIG. 2). The signature sequence for GH16 (E-[LIV]-D-[LIVF]-X-E-XX-[GQ]-[KRNF]-X-[PSTA]; SEQ ID NO:26) is partially conserved in Aga16B, and both critical Glu residues are retained (Juncosa et al., 1994). In the agarases, the GH16 domain is located in the amino-terminal region of the polypeptide, immediately adjacent to a signal peptide. It is unclear whether this represents an orthologous relationship or a functional requirement for the domain location. The region in common between Aga50A and Aga50D (aa 350 to 769 and aa 325 to 747, respectively) is similar to the GH50 domains of the *Vibrio* sp. strain JT0107 agarases (FIG. 3). A partially conserved region extends for at least 375 aa and is located in the carboxy-terminal end of the polypeptides. As mentioned before, it has not been established whether this is a functional requirement for the domain. The region conserved between Aga86C and Aga86E (aa 147 to 787 and aa 633 to 1316, respectively) shows sequence similarity to the GH86 domain of *P. atlantica* AgrA (FIG. 4). This region, however, is highly divergent, with only localized regions of sequence similarity apparent.

Figure 6:
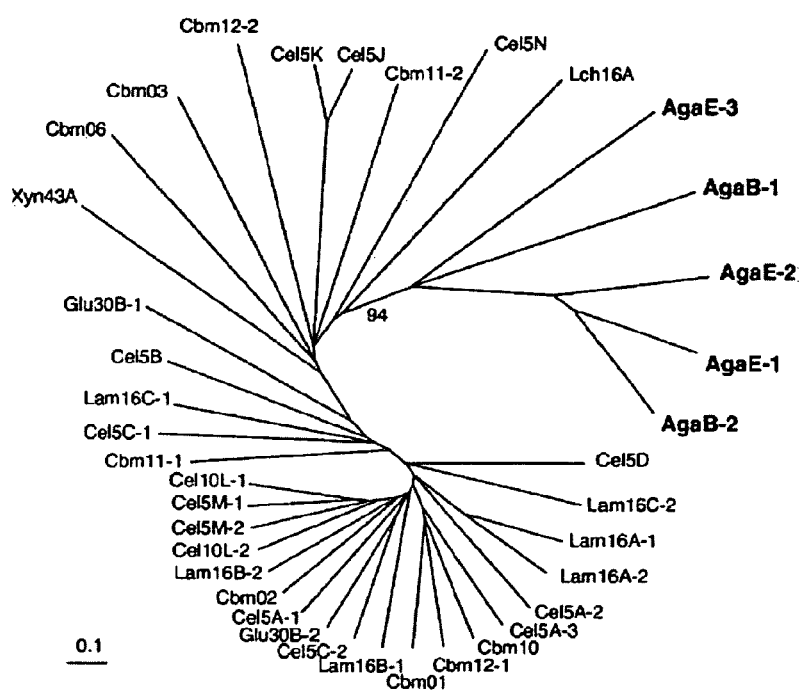
FIG. 6 shows unrooted phylogenetic tree for CBM6 domains identified in the *S. degradans* 2-40 genome. The scale bar indicates the number of substitutions per position following alignment with MUSCLE (Edgar, 2004) and bootstrap analysis by ClustalW. The tree was generated using neighbor joining and displayed with TreeView (Page, 1996). The bootstrap value (out of a sampling of 100) is shown for the node linking the agarase CBM (bold). Abbreviations: Aga, known agarase; Cbm, protein containing a carbohydrate binding module; Cel, predicted endoglucanase; Glu, predicted β-glucosidase; Lam, candidate laminarinase; Lch, lichenase; Xyn, candidate xylanase.

Unusual for agarases, two apparent CBM6 were identified in the carboxy-terminal region of Aga16B (CBM6-B1, aa 322 to 445, and CBM6-B2, aa 455 to 593) and three predicted CBM6 were located in the amino-terminal 650-aa region of Aga86E (CBM6-E1, aa 9 to 148, CBM6-E2, aa 162 to 302, and CBM6-E3, aa 349 to 483) (FIG. 1 and FIG. 5). Phylogenetic analyses indicated that predicted CBM6 of the agarases are distinct from other CBM6 found in the *S. degradans* 2-40 genome (FIG. 6). CBM6-E1, -E2, and -B2 were most closely related to each other, whereas CBM6-E3 and -B1 formed a second group strongly supported by bootstrap analysis (see FIG. S4). A repetitive linker sequence of (P-X)i7(SEQ ID NO: 63) separated the first and second CBM6 of Aga86E; the second and third CBM6, were separated by an (E-P)17 (SEQ ID NO: 64) repeat. Four thrombospondin type 3 repeats were also identified between aa 511 and 643. The function of these repeats is unknown. As expected for secreted proteins, cleavable type II secretion signals were detected in the amino termini of Aga50A, Aga16B, Aga86C, Aga50D, and Aga86E. A predicted lipoprotein acylation site (d'Enfert et al., 1989) was identified in the amino terminus of Aga86C.

Example 4

Activities of the *Candidate agarases*

To determine whether the candidate agarases have the predicted activities, each was cloned into pETBIue-2 to create carboxy-terminal His6-tagged (SEQ ID NO: 65) derivatives. *E. coli* Tuner (pLac1)(pNEaga16B1) expressing Aga16B-His rapidly pitted agar plates, which was usually apparent after overnight growth, even in the absence of induction. Upon purification of Aga16B-His, the expected 65-kDa product and an 85-kDa derivative were detected in immunoblots probed with anti-His antibodies, as well as by mass spectrometry. Anomalous migration of *S. degradans* 2-40 proteins appears to be common, as several *S. degradans* 2-40 carbohydrases expressed in E. co/i migrate at higher-than-predicted molecular masses for unknown reasons.

In order to determine the biochemical activity of Aga16B, the products of Aga16B-mediated degradation of agarose were characterized by thin-layer chromatography. Digestion of agarose by Aga16B-His released neoagarotetraose and neoagarohexaose, but neoagarobiose could not be detected, even after long-term incubation. These results are consistent with endolytic β-agarase I-like activity. In contrast, only D-galactose was detected when agarose was digested with cell-free lysates of *S. degradans* 2-40, indicating the expression of additional enzymes to degrade neoagarooligosaccharides.

*E. coli* transformants expressing Aga86E-His also exhibited agarase activity. *E. coli* Tuner(pLacI)(pNEaga86E1) slowly pitted agar plates, requiring several weeks before the phenotype was evident. Spontaneously forming Aga86E-His amino-terminal truncations with masses of 100 and 86 kDa exhibited agarase activity in zymograms, but the full-length 146-kDa Aga86E-His lacked activity. It was unclear whether the absence of activity at the expected molecular mass for full-length Aga86E represented a precursor state for the enzyme or the failure to renature the full-length polypeptide under the conditions of the zymogram.

When the products resulting from the activity of purified Aga86E-His were analyzed by thin-layer chromatography, only neoagarobiose was released from agarose by Aga86E-

His digestion after extended incubation (1 to 2 days). This is consistent with the slow-pitting phenotype of the Tuner transfectants expressing Aga86E-His. Because only neoagarobiose appears to be released by Aga86E activity, this enzyme appears to exolytically degrade agarose similarly to a β-agarase II.

It is unusual for agarases to carry CBM6. Like other carbohydrases, the CBM6 of Aga16B and Aga86E do not appear to be required for agarase activity. Truncated His-tagged derivatives of aga16B lacking one or both CBM6 exhibited agarase activity indistinguishable from that of the full-length form. Similarly, the spontaneously occurring amino-terminal truncations of Aga86E that are missing one or more of the resident CBM6 also retained agarase activity under laboratory conditions.

For unknown reasons, it was not possible to express Aga50A, Aga86C, and Aga50D in *E. coli*. The genes could be cloned into the nonexpressing *E. coli* strain DH5α-E, but attempts to transfer these clones into expressing strains, such as *E. coli* Tuner(DE3)(pLysS), were unsuccessful. Although some codons rarely used in *E. coli* were present in these genes, the expressible agarases also contained these codons at similar frequencies.

Aga16B, Aga86C, and Aga86E are Expressed and Secreted by *S. degradans* During Growth on Agar To determine if any of the demonstrated or predicted agarases are expressed during growth on agarose, clarified and concentrated culture filtrates from agarose-grown cells were surveyed by HPLC-coupled tandem MS. Fragments indicative of Aga16B, Aga86C, and Aga86E were detected in total culture filtrates of agarose-grown *S. degradans* 2-40, but several predicted cytoplasmic proteins were also detected in these samples, which limited interpretation of the data. Only Aga86E was detected during similar analyses of culture filtrates from glucose-grown cells. When specific size-classed proteins from culture filtrates were analyzed by mass spectrometry, fragments consistent with the presence of Aga86C were detected in the agarase-active 85-kDa sample and Aga86E was the dominant component of the 150-kDa fraction. The data confirm that Aga16B, Aga86C, and Aga86E are expressed and secreted during the degradation of agarose.

Example 5

Aga50A and Aga86E are Required for Agar Metabolism

The mosaicism of the *S. degradans* 2-40 genome and the identification of the components of an apparent competence system within the genome sequence suggested that *S. degradans* 2-40 can be naturally competent. If so, the mutagenesis procedures developed for an *Acinetobacter* sp. (Metzgar et al., 2004) should be applicable to *S. degradans* 2-40. This strategy employs linear mutagenic fragments that recombine into the genome by homologous recombination.

Mutagenic constructs for *S. degradans* 2-40 were assembled by fusing the 1-kb segments flanking each side of a gene of interest to an antibiotic resistance cassette by using splicing PCR (Metzgar et al., 2004; Murphy, 1998). Each of the resulting linear mutagenic constructs (5' flank:nptI:3' flank) was added to a newly inoculated, exponentially growing culture of *S. degradans* 2-40, and after 2 h of incubation, potential transformants carrying gene replacements were selected. Kan$^r$ colonies appeared at a frequency of $6 \times 10^{-6}$. Approximately 20% of these apparent transformants appeared to be gene replacements, as indicated by the presence of diagnostic PCR fragments. By this procedure, Δaga50A::nptI (*S. degradans* NE-A1) and Δaga86E::nptI (*S. degradans* NE-E1) mutants were created.

In order to evaluate the role of the demonstrated or predicted agarases in the degradation of agar, the constructed agarase mutants were screened for agarase complement in zymograms of cell lysates and their ability to utilize agar as a sole carbon source. Neither mutant was able to grow on agar as the sole carbon source, whereas a similarly constructed ΔchiA:nptI mutant retained this ability. When grown on media supplemented with glucose, the mutants pitted the medium slowly, but less so than wild-type *S. degradans* 2-40. The zymograms of the *S. degradans* NE-A1 and *S. degradans* NE-E1 lysates revealed no change in agarase activity relative to that of the wild type, although immunoblots showed *S. degradans* NE-E1 to lack Aga86E. These results indicate that the phenotype of the mutants is unlikely to be due to altered expression of other agarases but can be attributed to an essential role for the deleted gene product.

Example 6

The Agarolytic System of *S. degradans* 2-40 Requires Additional Components

To clarify the essential components of the agarolytic system, the cloned agarases were transformed into *E. coli* in an attempt to assemble a functional agarolytic system. The Aga$^+$ pNE10 identified during the screen of the *S. degradans* 2-40 genomic library carries both aga50A and aga16B as well as the β-galactosidase-like galA gene. This plasmid was transformed into Gal$^+$ *E. coli* DH5α or HB101 and Gal$^-$*E. coli* DH5α-E or TOP10 (Invitrogen) with or without pSHAga86E2 expressing aga86E. None of the resulting strains, however, were able to metabolize agarose as a sole carbon and energy source. Since the Gal$^+$ transformants carrying both plasmids were highly unstable, an alternative test was performed. Gal$^-$ Aga$^+$ strains of *E. coli* carrying either pNE10 or pSHAga86E2 were cross-streaked on several indicator media lacking an added carbon source and then overlaid with a Gal$^+$ indicator strain. Galactose production was not detected in any medium, suggesting that the agarolytic system employs additional components not closely associated with aga50A, aga16B, or aga86E to convert agarose to galactose.

REFERENCES

Allouch, J., W. Helbert, B. Henrissat, and M. Czjzek. 2004. Parallel substrate binding sites in a beta-agarase suggest a novel mode of action on double-helical agarose. Structure. 12:623-32.

Allouch, J., M. Jam, W. Helbert, T. Barbeyron, B. Kloareg, B. Henrissat, and M. Czjzek. 2003. The three-dimensional structures of two beta-agarases. J Biol Chem. 278:47171-80.

Altschul, S. F., W. Gish, W. Miller, E. W. Myers, and D. J. Lipman. 1990. Basic local alignment search tool. J Mol Biol. 215:403-10.

Andrykovitch, G., and I. Marx. 1988. Isolation of a New Polysaccharide-Digesting Bacterium from a Salt Marsh. Appl Environ Microbiol. 54:1061-1062.

Aoki, T., T. Araki, and M. Kitamikado. 1990. Purification and characterization of a novel beta-agarase from *Vibrio* sp. AP-2. Eur J Biochem. 187:461-5.

Araki, T., M. Hayakawa, Z. Lu, S. Karita, and T. Morishita. 1998. Purification and characterization of agarases from a marine bacterium, *Vibrio* sp. PO-303. J Mar Biotechnol. 6:260-265.

Ausubel, F. M., R. Brent, R. E. Kingston, D. D. Moore, J. G. Seidman, J. A. Smith, and K. Struhl. 1987. Current protocols in molecular biology. John Wiley & Sons, New York.

Barbeyron, T., S. L'Haridon, E. Corre, B. Kloareg, and P. Potin. 2001. *Zobellia galactanovorans* gen. nov., sp. nov., a marine species of Flavobacteriaceae isolated from a red alga, and classification of. Int J Syst Evol Microbiol. 51:985-97.

Belas, R. 1989. Sequence analysis of the agrA gene encoding beta-agarase from *Pseudomonas atlantica*. J Bacteriol. 171:602-5.

Bendtsen, J. D., H. Nielsen, G. von Heijne, and S. Brunak. 2004. Improved prediction of signal peptides: SignalP 3.0. J Mol Biol. 340:783-95.

Bibb, M. J., G. H. Jones, R. Joseph, M. J. Buttner, and J. M. Ward. 1987. The agarase gene (dag A) of *Streptomyces coelicolor* A3(2): affinity purification and characterization of the cloned gene product. J Gen Microbiol. 133:2089-96.

Coutinho, P., and B. Henrissat. 1999a. Carbohydrate-active enzymes: an integrated database approach. In Recent advances in carbohydrate engineering. Vol. H. Gilbert, G. Davies, B. Henrissat, and b. Swensson, editors. The Royal Society of Chemistry, Cambridges. 3-12.

Coutinho, P., and B. Henrissat. 1999b. The modular structure of cellulases and other carbohydrate-active enzymes: an integrated database approach. In Genetics, biochemistry and ecology of cellulose degradation. Vol. K. Ohymiya, K. Hayashi, K. Sakka, C. Kobayashi, S. Karita, and K. T, editors. Uni Publishers Co., Tokyo. 15-23.

Craigie, J. 1990. Cell walls. In Biology of the red algae. Vol. K. M. Cole and R. G. Sheath, editors. Cambridge University Press, Cambridge [England]; New York. 221-258.

d'Enfert, G, I. Reyss, C. Wandersman, and A. P. Pugsley. 1989. Protein secretion by gram-negative bacteria. Characterization of two membrane proteins required for pullulanase secretion by *Escherichia coli* K-12. J Biol Chem. 264:17462-8.

Duckworth, M., and W. Yaphe. 1970. Thin-layer chromatographic analysis of enzymic hydrolysates of agar. J Chromatogr. 49:482-7.

Edgar, R. C. 2004. MUSCLE: multiple sequence alignment with high accuracy and high throughput. Nucleic Acids Res. 32:1792-7.

Ekborg, N. A., J. M. Gonzalez, M. B. Howard, L. E. Taylor, S. W. Hutcheson, and R. M. Weiner. 2005. *Saccharophagus degradans* gen. nov., sp. nov., a versatile marine degrader of complex polysaccharides. Int J Syst Evol Microbiol. 55:1545-9.

Eng, J., A. Mccormack, and I. Yates, J. R. 1994. J. Am. Soc. Mass Spectrom. 5:976-989.

Ensor, L., S. Stosz, and R. Weiner. 1999. Expression of multiple complex polysaccharide-degrading enzyme systems by marine bacterium strain 2-40. J Ind Microbiol Biotechnol. 23:123-126.

Finn, R. D., J. Mistry, B. Schuster-Bockler, S. Griffiths-Jones, V. Hollich, T. Lassmann, S. Moxon, M. Marshall, A. Khanna, R. Durbin, S. R. Eddy, E. L. Sonnhammer, and A. Bateman. 2006. Pfam: clans, web tools and services. Nucleic Acids Res. 34:D247-51.

Gasteiger, E., C. Hoogland, A. Gattiker, S. Duvaud, M. R. Wilkins, R. D. Appel, and A. Bairoch. 2005. Protein Identification and Analysis Tools on the ExPASy Server. In The Proteomics Protocols Handbook. Vol. J. Walker, editor Humana Press, 571-607.

Gonzalez, J. M., and R. M. Weiner. 2000. Phylogenetic characterization of marine bacterium strain 2-40, a degrader of complex polysaccharides. Int J Syst Evol Microbiol. 50 Pt 2:831-4.

Ha J. C., G. T. Kim, S. K. Kim, T. K. Oh, J. H. Yu, and I. S. Kong. 1997. beta-Agarase from *Pseudomonas* sp. W7: purification of the recombinant enzyme from *Escherichia coli* and the effects of salt on its activity. Biotechnol Appl Biochem. 26 (Pt 1):1-6.

Hosoda, A., M. Sakai, and S. Kanazawa. 2003. Isolation and characterization of agar-degrading *Paenibacillus* spp. associated with the rhizosphere of spinach. Biosci Biotechnol Biochem. 67:1048-55.

Howard, M. B., N. A. Ekborg, L. E. Taylor, R. M. Weiner, and S. W. Hutcheson. 2003. Genomic analysis and initial characterization of the chitinolytic system of *Microbulbifer degradans* strain 2-40. J Bacteriol. 185:3352-60.

Juncosa, M., J. Pons, T. Dot, E. Querol, and A. Planas. 1994. Identification of active site carboxylic residues in *Bacillus licheniformis* 1,3-1,4-beta-D-glucan 4-glucanohydrolase by site-directed mutagenesis. J Biol Chem. 269:14530-5.

Kang, N. Y., Y. L. Choi, Y. S. Cho, B. K Kim, B. S. Jeon, J. Y. Cha, C. H. Kim, and Y. C. Lee. 2003. Cloning, expression and characterization of a beta-agarase gene from a marine bacterium, *Pseudomonas* sp. SK38. Biotechnol Lett. 25:1165-70.

Kelly, S., V. Coyne, D. Sledjeski, C. Fuqua, and R. Weiner. 1990. Identification of a tyrosinase from a periphytic marine bacterium. FEMS Microbiol. Lett. 67:275-280.

Kobayashi, R., M. Takisada, T. Suzuki, K. Krimura, and S. Usami. 1997. Neoagarobiose as a novel moisturizer with whitening effect. Biosci Biotechnol Biochem. 61:162-3.

Letunic, I., R. R. Copley, B. Pils, S. Pinkert, J. Schultz, and P. Bork. 2006. SMART 5: domains in the context of genomes and networks. Nucleic Acids Res. 34:D257-60.

Metzgar, D., J. M. Bacher, V. Pezo, J. Reader, V. Doring, P. Schimmel, P. Marliere, and V. de Crecy-Lagard. 2004. *Acinetobacter* sp. ADP1: an ideal model organism for genetic analysis and genome engineering. Nucleic Acids Res. 32:5780-90.

Morrice, L. M., M. W. McLean, W. F. Long, and F. B. Williamson. 1983a. Beta-agarases I and II from *Pseudomonas atlantica*. Substrate specificities. Eur J Biochem. 137:149-54.

Morrice, L. M., M. W. McLean, F. B. Williamson, and W. F. Long. 1983b. beta-agarases I and II from *Pseudomonas atlantica*. Purifications and some properties. Eur J Biochem. 135:553-8.

Murphy, K. C. 1998. Use of bacteriophage lambda recombination functions to promote gene replacement in *Escherichia coli*. J Bacteriol. 180:2063-71.

Ohta, Y., Y. Hatada, S. Ito, and K. Horikoshi. 2005. High-level expression of a neoagarobiose-producing beta-agarase gene from *Agarivorans* sp. JAMB-A11 in *Bacillus subtilis* and enzymic properties of the recombinant enzyme. Biotechnol Appl Biochem. 41:183-91.

Ohta, Y., Y. Hatada, Y. Nogi, Z. Li, S. Ito, and K. Horikoshi. 2004a. Cloning, expression, and characterization of a glycoside hydrolase family 86 beta-agarase from a deep-sea *Microbulbifer*-like isolate. Appl Microbiol Biotechnol. 66:266-75.

Ohta, Y., Y. Nogi, M. Miyazaki, Z. Li, Y. Hatada, S. Ito, and K. Horikoshi. 2004b. Enzymatic properties and nucleotide and amino acid sequences of a thermostable beta-agarase from the novel marine isolate, JAMB-A94. Biosci Biotechnol Biochem. 68:1073-81.

Page, R. D. 1996. Tree View: an application to display phylogenetic trees on personal computers. Comput Appl Biosci. 12:357-8.

Perkins, D. N., D. J. Pappin, D. M. Creasy, and J. S. Cottrell. 1999. Probability-based protein identification by searching sequence databases using mass spectrometry data. Electrophoresis. 20:3551-67.

Plotkin, J. B., H. Robins, and A. J. Levine. 2004. Tissue-specific codon usage and the expression of human genes. Proc Natl Acad Sci USA. 101:12588-91.

Potin, P., C. Richard, C. Rochas, and B. Kloareg. 1993. Purification and characterization of the alpha-agarase from *Alteromonas agarlyticus* (Cataldi) comb, nov., strain GJ1B. Eur J Biochem. 214:599-607.

Sambrook, J., and D. W. Russell. 2001. Molecular cloning: a laboratory manual. Cold Spring Harbor Laboratory Press, Cold Spring Harbor, N.Y.

Schroeder, D. C., M. A. Jaffer, and V. E. Coyne. 2003. Investigation of the role of a beta(1-4) agarase produced by *Pseudoalteromonas gracilis* B9 in eliciting disease symptoms in the red alga *Gracilaria gracilis*. Microbiology. 149:2919-29.

Schultz, J., F. Milpetz, P. Bork, and C. P. Ponting. 1998. SMART, a simple modular architecture research tool: identification of signaling domains. Proc Natl Acad Sci USA. 95:5857-64.

Shieh, W. Y., and W. D. Jean. 1998. *Alterococcus agarolyticus*, gen.nov., sp.nov., a halophilic thermophilic bacterium capable of agar degradation. Can J Microbiol. 44:637-45.

Sugano, Y., H. Kodama, I. Terada, Y. Yamazaki, and M. Noma. 1994a. Purification and characterization of a novel enzyme, alpha-neoagarooligosaccharide hydrolase (alpha-NAOS hydrolase), from a marine bacterium, *Vibrio* sp. strain JT0107. J Bacteriol. 176:6812-8.

Sugano, Y., T. Matsumoto, H. Kodama, and M. Noma. 1993. Cloning and sequencing of agaA, a unique agarase 0107 gene from a marine bacterium, *Vibrio* sp. strain JT0107. Appl Environ Microbiol. 59:3750-6.

Sugano, Y., T. Matsumoto, and M. Noma. 1994b. Sequence analysis of the agaB gene encoding a new beta-agarase from *Vibrio* sp. strain JT0107. Biochim Biophys Acta. 1218:105-8.

Swartz, M. N., and N. Gordon. 1959. Agarase from an agar-digesting bacterium. J Bacteriol. 77:403-9.

Thompson, J. D., T. J. Gibson, F. Plewniak, F. Jeanmougin, and D. G. Higgins. 1997. The CLUSTAL_X windows interface: flexible strategies for multiple sequence alignment aided by quality analysis tools. Nucleic Acids Res. 25:4876-82.

Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-80.

Turvey, J. R., and J. Christison. 1967. The hydrolysis of algal galactans by enzymes from a *Cytophaga* species. Biochem J. 105:311-6.

Uetanabaro, A. P., C. Wahrenburg, W. Hunger, R. Pukall, C. Sproer, E. Stackebrandt, V. P. de Canhos, D. Claus, and D. Fritze. 2003. *Paenibacillus agarexedens* sp. nov., nom. rev., and *Paenibacillus agaridevorans* sp. nov. Int J Syst Evol Microbiol. 53:1051-7.

Van der Meulen, H. J., and W. Harder. 1975. Production and characterization of the agarase of *Cytoplaga flevensis*. Antonie Van Leeuwenhoek. 41:431-47.

Whitehead, L. A., S. K. Stosz, and R. M. Weiner. 2001. Characterization of the agarase system of a multiple carbohydrate degrading marine bacterium. Cytobios. 106 Suppl 1:99-117.

Wilkins, M. R., I. Lindskog, E. Gasteiger, A. Bairoch, J. C. Sanchez, D. F. Hochstrasser, and R. D. Appel. 1997. Detailed peptide characterization using PEPTIDEMASS-a World-Wide-Web-accessible tool. Electrophoresis. 18:403-8.

Xu, Q., M. Morrison, K. E. Nelson, E. A. Bayer, N. Atamna, and R. Lamed. 2004. A novel family of carbohydrate-binding modules identified with *Ruminococcus albus* proteins. FEBS Lett. 566:11-6.

Zhong, Z., A. Toukdarian, D. Helinski, V. Knauf, S. Sykes, J. E. Wilkinson, C. O'Bryne, T. Shea, C. DeLoughery, and R. Caspi. 2001. Sequence analysis of a 101-kilobase plasmid required for agar degradation by a *Microscilla* isolate. Appl Environ Microbiol. 67:5771-9.

---

We claim:

1. A method of producing neoagarobiose, comprising:
   (a) providing a substrate selected from the group consisting of agar, agarose, neoagarotetraose, agarooligosaccharides, and derivatives thereof;
   (b) contacting the substrate with a *Saccharophagus degradans* glycoside hydrolase (GH) polypeptide having at least 80% sequence identity with the amino acid sequence of SEQ ID NO:9, wherein the *Saccharophagus degradans* glycoside hydrolase (GH) polypeptide has exo-acting β-agarase activity, thereby creating a reaction mix; and
   (c) incubating the reaction mix under suitable conditions and sufficient time to produce neoagarobiose from the substrate.

2. The method of claim 1, wherein the polypeptide comprises the amino acid sequence of SEQ ID NO:9.

3. The method of claim 1, wherein the polypeptide consists of the amino acid sequence of SEQ ID NO:9.

4. The method of claim 1, further comprising contacting the substrate with at least one carbohydrate binding module polypeptide having at least 80% sequence identity with an amino acid sequence selected from the group consisting of SEQ ID NOs:5, 6 and 7.

5. The method of claim 4, wherein the at least one carbohydrate binding module polypeptide has at least 90% sequence identity with the amino acid sequence selected from the group consisting of SEQ ID NOs:5, 6 and 7.

6. The method of claim 4, wherein the at least one carbohydrate binding module polypeptide is selected from the group consisting of SEQ ID NOs:5, 6 and 7.

7. The method of claim 4, wherein the substrate is contacted with a carbohydrate binding module of SEQ ID NO:5, a carbohydrate binding module of SEQ ID NO:6, and a carbohydrate binding module of SEQ ID NO:7.

8. The method of claim 1, further comprising contacting the substrate with a second polypeptide comprising an amino acid sequence having at least 80% sequence identity with an amino acid sequence of SEQ ID NO:12.

9. The method of claim 8, wherein the second polypeptide comprises an amino acid sequence having at least 90% sequence identity with the amino acid sequence of SEQ ID NO:12.

10. The method of claim 8, wherein the second polypeptide comprises an amino acid sequence of SEQ ID NO:12.

11. The method of claim 8, wherein the substrate is first contacted with the second polypeptide.

12. The method of claim 8, further comprising contacting the substrate with at least one carbohydrate binding module polypeptide having at least 80% sequence identity with an amino acid sequence of SEQ ID NO:10 or 11.

13. The method of claim 8, further comprising contacting the substrate with at least one carbohydrate binding module polypeptide having at least 90% sequence identity with an amino acid sequence of SEQ ID NO:10 or 11.

14. The method of claim 8, further comprising contacting the substrate with at least one carbohydrate binding module polypeptide comprising an amino acid sequence of SEQ ID NO:10 or 11.

15. A method of producing neoagarobiose, comprising:
   (a) providing a substrate selected from the group consisting of agar, agarose, neoagarotetraose, agarooligosaccharides, and derivatives thereof;
   (b) contacting the substrate with a *Saccharophagus degradans* polypeptide having at least 90% sequence identity with the amino acid sequence of SEQ ID NO:9, wherein the *Saccharophagus degradans* polypeptide has exo-acting β-agarose activity, thereby creating a reaction mix; and (c) incubating the reaction mix under suitable conditions and sufficient time to produce neoagarobiose from the substrate.

* * * * *

SEQUENCE LISTING

```
<160> NUMBER OF SEQ ID NOS: 65

<210> SEQ ID NO 1
<211> LENGTH: 593
<212> TYPE: PRT
<213> ORGANISM: Saccharophagus degradans

<400> SEQUENCE: 1

Met Arg Pro Ser Cys Ala Phe Phe Ser Thr Pro Leu Met Ala Ala Asp
 1               5                  10                  15

Trp Asp Gly Ile Pro Val Pro Ala Asp Pro Gly Asn Gly Asn Thr Trp
            20                  25                  30

Glu Leu Gln Ser Leu Ser Asp Asp Phe Asn Tyr Ala Ala Pro Ala Asn
        35                  40                  45

Gly Lys Arg Thr Thr Phe Tyr Ser Arg Trp Ser Glu Gly Phe Ile Asn
    50                  55                  60

Ala Trp Leu Gly Pro Gly Gln Thr Glu Phe Tyr Gly Pro Asn Ala Ser
65                  70                  75                  80

Val Glu Gly Gly His Leu Ile Ile Lys Ala Thr Arg Lys Pro Gly Thr
```

```
                        85                  90                  95
Thr Gln Ile Tyr Thr Gly Ala Ile His Ser Asn Glu Ser Phe Thr Tyr
            100                 105                 110

Pro Leu Tyr Leu Glu Ala Arg Thr Lys Ile Thr Asn Leu Thr Leu Ala
            115                 120                 125

Asn Ala Phe Trp Leu Leu Ser Asp Ser Thr Glu Glu Ile Asp Val
            130                 135                 140

Leu Glu Ser Tyr Gly Ser Asp Arg Ala Thr Glu Thr Trp Phe Asp Glu
145                 150                 155                 160

Arg Leu His Leu Ser His His Val Phe Ile Arg Gln Pro Phe Gln Asp
                    165                 170                 175

Tyr Gln Pro Lys Asp Ala Gly Ser Trp Tyr Pro Asn Pro Asp Gly Gly
                180                 185                 190

Thr Trp Arg Asp Gln Phe Phe Arg Ile Gly Val Tyr Trp Ile Asp Pro
            195                 200                 205

Trp Thr Leu Glu Tyr Tyr Val Asn Gly Glu Leu Val Arg Thr Val Ser
210                 215                 220

Gly Pro Glu Met Ile Asp Pro Tyr Gly Tyr Thr Asn Gly Thr Gly Leu
225                 230                 235                 240

Ser Lys Pro Met Gln Val Ile Phe Asp Ala Glu His Gln Pro Trp Arg
                    245                 250                 255

Asp Glu Gln Gly Thr Ala Pro Pro Thr Asp Ala Glu Leu Ala Asp Ser
                260                 265                 270

Ser Arg Asn Gln Phe Leu Ile Asp Trp Val Arg Phe Tyr Lys Pro Val
                    275                 280                 285

Ala Ser Asn Asn Gly Gly Asp Pro Gly Asn Gly Gly Thr Pro Gly
            290                 295                 300

Asn Gly Gly Ser Gly Asp Thr Val Val Val Glu Met Ala Asn Phe Ser
305                 310                 315                 320

Ala Thr Gly Lys Glu Gly Ser Ala Val Ala Gly Asp Thr Phe Thr Gly
                    325                 330                 335

Phe Asn Pro Ser Gly Ala Asn Asn Ile Asn Tyr Asn Thr Leu Gly Asp
                340                 345                 350

Trp Ala Asp Tyr Thr Val Asn Phe Pro Ala Ala Gly Asn Tyr Thr Val
            355                 360                 365

Asn Leu Ile Ala Ala Ser Pro Val Thr Ser Gly Leu Gly Ala Asp Ile
            370                 375                 380

Leu Val Asp Ser Ser Tyr Ala Gly Thr Ile Pro Val Ser Ser Thr Gly
385                 390                 395                 400

Ala Trp Glu Ile Tyr Asn Thr Phe Ser Leu Pro Ser Ser Ile Tyr Ile
                405                 410                 415

Ala Ser Ala Gly Asn His Thr Ile Arg Val Gln Ser Ser Gly Gly Ser
                    420                 425                 430

Ala Trp Gln Trp Asn Gly Asp Glu Leu Arg Phe Thr Gln Thr Asp Ala
                435                 440                 445

Asp Thr Gly Thr Asn Pro Pro Ser Thr Ala Ser Ile Ala Val Glu Ala
            450                 455                 460

Glu Asn Phe Asn Ala Val Gly Gly Thr Phe Ser Asp Gly Gln Ala Gln
465                 470                 475                 480

Pro Val Ser Val Tyr Thr Val Asn Gly Asn Thr Ala Ile Asn Tyr Val
                    485                 490                 495

Asn Gln Gly Asp Tyr Ala Asp Tyr Thr Ile Ala Val Ala Gln Ala Gly
                500                 505                 510
```

```
Asn Tyr Thr Ile Ser Tyr Gln Ala Gly Ser Gly Val Thr Gly Gly Ser
        515                 520                 525

Ile Glu Phe Leu Val Asn Glu Asn Gly Ser Trp Ala Ser Lys Thr Val
        530                 535                 540

Thr Ala Val Pro Asn Gln Gly Trp Asp Asn Phe Gln Pro Leu Asn Gly
545                 550                 555                 560

Gly Ser Val Tyr Leu Ser Ala Gly Thr His Gln Val Arg Leu His Gly
                565                 570                 575

Ala Gly Ser Asn Asn Trp Gln Trp Asn Leu Asp Lys Phe Thr Leu Ser
            580                 585                 590

Asn
```

<210> SEQ ID NO 2
<211> LENGTH: 1782
<212> TYPE: DNA
<213> ORGANISM: Saccharophagus degradans

<400> SEQUENCE: 2

```
atgcgcccta gctgcgcctt cttcagtacc cctcttatgg ctgcagattg ggacggaatt     60
cctgtcccag cggacccagg gaatggcaac acctgggagc tacagtccct ttctgacgat    120
ttcaactatg cggccccagc taacggcaaa cgcaccacct tctatagccg ctggagcgaa    180
ggctttatca atgcttggct cggcccgggg caaaccgagt tttacggccc caatgcttcg    240
gtagaaggcg gccaccttat tattaaggcc actcgcaagc caggtactac tcaaatttac    300
actggagcaa ttcactccaa tgaaagtttt acctacccat tgtatttgga agcgcgcacc    360
aaaattacaa acctcaccct cgccaacgca ttttggctac taagctcaga ttccaccgaa    420
gagattgatg tgctggagtc ttacggcagc gaccgtgcaa cagaaacgtg gtttgacgaa    480
cgcctacact aagccatca cgtttttatc cgccagccat tcaagacta ccaaccgaaa    540
gatgcaggca gctggtaccc caaccccgat ggcggcactt ggcgcgacca ttttttccgt    600
ataggtgttt attggataga cccatggaca ctggagtatt acgtgaatgg cgaattagtg    660
cgcactgtaa gcgcccagaa atgattgac ccgtacggtt acaccaacgg cacaggccta    720
agtaaacccca tgcaagttat tttcgatgca gagcatcagc cttggcgcga cgaacaaggt    780
actgccccac ccaccgacgc agagctagcc gactcgagtc gcaatcaatt cttaattgac    840
tgggtgcgat tctacaaacc cgtggcaagc aacaatggtg gcggcgaccc aggcaatggc    900
ggcacccccag gtaatggtgg cagtggcgat actgtagtgg tagaaatggc caacttctct    960
gccacaggta agaaggctc tgcagttgca ggcgacactt tcacaggctt caaccccagc   1020
ggcgcgaaca acatcaacta caacaccta ggggattggg cagactacac ggtgaacttc   1080
cccgctgccg gtaattacac cgtaaaccta attgcagcct cgccggttac atctgggctg   1140
ggtgcagata ttttggtaga cagcagttac gcaggcacca tacctgttag cagcaccgga   1200
gcttgggaga tatacaacac cttagcttg cccagctcga tttatatcgc aagcgcaggc   1260
aatcatacta ttcgcgtaca aagctccggc ggtagcgctt ggcagtggaa cggcgacgaa   1320
cttcgctta cccaaacgga tgcggataca ggcaccaatc cacccagtac agccagcata   1380
gcggttgaag ccgaaaactt taacgcggtg gcggcacct tagcgatgg tcaagctcaa   1440
cctgttagcg tttacaccgt taacggcaac actgccatta actacgtaaa ccaaggcgat   1500
tatgccgact acaccattgc tgttcccaa gcgggtaact acaccattag ctatcaagct   1560
ggcagtggcg taacaggtgg tagcatagag ttttttggtta acgaaaacgg aagctgggcc   1620
```

-continued

```
agtaaaaccg ttaccgccgt accaaaccaa ggttgggata acttccaacc cttaaacgga    1680
ggcagcgttt acctaagcgc aggcacccac caagttcgtt tacacggcgc tggcagcaac    1740
aactggcagt ggaacctaga taagttcacg cttagcaact aa                      1782
```

<210> SEQ ID NO 3
<211> LENGTH: 1316
<212> TYPE: PRT
<213> ORGANISM: Saccharophagus degradans

<400> SEQUENCE: 3

```
Met Ser Val Leu Pro Leu Ala Gly Ala Ala Asp Tyr Val Ile Glu
 1               5                  10                  15

Ala Glu Asn Phe Val Ala Gln Gly Gly Thr Tyr Val Asp Gly Gln Pro
                20                  25                  30

Asn Lys Val Ser Val Tyr Ser Val Asn Gly Ala Thr Ala Ile Asn Tyr
            35                  40                  45

Val Asn Arg Ala Asp Tyr Thr Asp Tyr Gln Ile Asn Val Ala Thr His
        50                  55                  60

Gly Tyr Tyr Asn Val Gln Tyr Ala Ile Gly Thr Ser Val Ala Ser Gly
 65                  70                  75                  80

Ala Ala Ile Glu Leu Leu Val Gln Asn Gly Ser Ser Trp Glu Ser Gln
                85                  90                  95

Gly Gln Thr Asn Val Pro Val Gly His Trp Asp Ser Phe Gln Pro Leu
            100                 105                 110

Asn Ala Ser His Glu Val Ile Leu Pro Ala Gly Thr Val Asn Leu Arg
        115                 120                 125

Val Tyr Gly Ala Gly Ser Asn Asp Trp Gln Trp Asn Leu Asp Ser Ile
    130                 135                 140

Ser Leu Thr Leu Glu Ser Ala Ile Asn Pro Gln Pro Asp Pro Asp Pro
145                 150                 155                 160

Asp Pro Ser Pro Gln Leu Val Lys Thr Glu Ala Glu Ala Phe Asn Ala
                165                 170                 175

Gln Ser Gly Thr Phe Ala Asp Gly Gln Pro Thr Pro Val Ser Ile Tyr
            180                 185                 190

Thr Val Asn Gly Lys Thr Ala Ile Asn Phe Val Asn Lys Gly Asp Ala
        195                 200                 205

Val Glu Tyr Asn Leu Val Ala Pro Ala Gly Ser Tyr Ala Leu Lys
    210                 215                 220

Tyr Ser Ile Gly Thr Ser Val Ala Ser Gly Ser Glu Val Glu Phe Phe
225                 230                 235                 240

Val Leu Lys Asn Asn Val Trp Val Ser Gln Gly Lys Thr Pro Val Pro
                245                 250                 255

Ala Val Gly Trp Asp Asn Phe Thr Ser Val Ala Ser Ala Gln Thr Val
            260                 265                 270

Glu Leu Ala Ala Gly Ser Asn Lys Val Lys Leu Val Gly Ala Gly Thr
        275                 280                 285

Asn Asp Trp Gln Trp Asn Leu Asp Phe Phe Glu Leu Thr Leu Gly Asn
    290                 295                 300

Val Glu Pro Glu Pro Glu Pro Glu Pro Glu Pro Glu Pro Glu Pro Glu
305                 310                 315                 320

Pro Glu Pro Glu Pro Glu Pro Glu Pro Glu Pro Glu Pro Glu Pro Glu
                325                 330                 335

Pro Glu Pro Gln Pro Glu Pro Asp Gly Asp Pro Val Pro Val Ser Gly
```

```
                340               345               350
Ser Phe Lys Leu Glu Ala Glu His Phe Gln Lys Val Gly Gly Glu Val
            355               360               365
Gln Ile Tyr Ser Leu Ser Pro Gly Asn Ala Val Asn Tyr Phe Asn Ser
            370               375           380
Gly Asp Tyr Leu Glu Phe Tyr Val Asp Leu Asp Ala Gly Gly Leu Tyr
385               390               395               400
Glu Ala Ser Phe Arg Val Gly Thr Gly Val Ala Ser Asp Val Ala Val
                405               410               415
Gly Leu Met Val Thr Asp His Lys Gly Asp Leu Thr Leu Lys Ser Val
                420               425               430
Thr Pro Val Thr Asp Gln Gly Gly Trp Asp Ala Phe Tyr Asn Leu Thr
            435               440               445
Ala Gln Ser Gln Leu Asn Ile Tyr Ser Gly Ile Asn Thr Ile Arg Ile
            450               455               460
Thr Gly Ala Gly Ser Ala Asp Phe Gln Phe Asn Ile Asp Ser Ile Thr
465               470               475               480
Leu Thr Arg Val Gly Pro Ile Asn Pro Ala Leu Asp Gly Asp Asn Asp
                485               490               495
Gly Val Pro Asp Thr Ser Asp Asn Cys Pro Ser Ser Pro Ala Asn Glu
                500               505               510
Thr Ala Asn Ala Glu Gly Cys Val Pro Ser Gln Leu Asp Thr Asp Glu
            515               520               525
Asp Gly Ile Asn Asp Lys Ile Asp Gln Cys Asp Ala Thr Pro Ala Gly
            530               535               540
Asp Phe Val Asp Ala Leu Gly Cys Thr Ser Thr Gly Gly Asp Asp Asp
545               550               555               560
Asp Phe Asp Gly Val Leu Asn Gly Ala Asp Gln Cys Gly Asn Thr Pro
                565               570               575
Tyr Gly Met Asn Val Asn Ala Gln Gly Cys Ser Val Phe Ser Gly Ser
            580               585               590
Asp Ala Asp Asn Asp Gly Val Ala Asn Ser Glu Asp Thr Cys Ala Asn
            595               600               605
Thr Pro Ala Leu Glu Phe Ala Asn Glu Gln Gly Cys Ser Ser Ser Gln
            610               615               620
Val Ala Asn Thr His Val Val Asn Val Ser Val Asn Ala Asn Phe Lys
625               630               635               640
Arg Ser Val Asn Gly Val Phe Asp Phe Gly Arg Arg His Met Thr
                645               650               655
Ala His Thr Ala Ile His Glu Pro Asp Trp Val Gly His Thr Asp Lys
            660               665               670
Leu Asn Tyr Leu Phe Asn Thr Leu Asp Val Tyr Met Gly Arg Asp Asn
            675               680               685
Gly Ser Ala Thr Trp Lys Phe Asn Asp Thr Thr Glu Asp Pro Asn Lys
            690               695               700
Pro Asn Trp Pro Asn Met Asp Tyr Met Val Glu Arg Gly Lys Gly Leu
705               710               715               720
Arg Glu Ala His Asp Gln Asn Pro Leu Phe Lys Arg Phe Ser Ala Glu
                725               730               735
Lys Gln Leu Leu Ile Ala Gly Thr Asn Pro His Ala Leu Tyr Pro Thr
            740               745               750
Leu Ser Trp Phe Pro Asn Ala Phe Thr Trp Ser Gly Trp Gln Pro Lys
            755               760               765
```

```
Asn Ile Glu Thr Ser Ala Ala Trp Val Gly Gln Tyr Met Glu His Tyr
        770                 775                 780
Phe Ala Asn Ala Ser Asn Gly Tyr Val Gly Glu Gln Leu Pro Glu Tyr
785                 790                 795                 800
Trp Glu Val Val Asn Glu Pro Asp Met Lys Met Lys Thr Gly Gln Phe
                805                 810                 815
Met Val Thr Asn Gln Glu Ala Ile Trp Glu Tyr His Asn Leu Val Ala
                    820                 825                 830
Gln Glu Ile Arg Asp His Leu Gly Ala Glu Ala Pro Pro Ile Gly Gly
            835                 840                 845
Met Thr Trp Gly Gln His Asp Phe Tyr Arg Arg Asp Gly Ile Ser Arg
    850                 855                 860
Phe Ala Asp Asp Ser Tyr Asp Gln Trp Ile Thr Asn Asp Asp Gln Val
865                 870                 875                 880
Leu Gln Ala Glu Ala Arg Ala Phe Tyr Arg Asn Ala Met Ala Thr Thr
                885                 890                 895
Val Asp Asp Thr Arg Asp Gln Asp Trp Tyr Gln Trp Asp Val Met Trp
                    900                 905                 910
Lys Gly Phe Met Asp Ala Ala Gly Asp Asn Met Asp Phe Tyr Ser Val
            915                 920                 925
His Ile Tyr Asp Trp Pro Gly Glu Asn Val Gly Asp Thr Thr Val Val
    930                 935                 940
Arg Arg Gly Gly His Thr Ser Ala Met Leu Glu Met Met Glu Trp Tyr
945                 950                 955                 960
Asp Val Lys Arg Asn Gly Phe Asn Asn Arg Lys Pro Ile Val Leu Ser
                965                 970                 975
Glu Tyr Gly Ser Val Asn Gly Ala Trp Asp Asn Arg Ala His Glu Glu
                    980                 985                 990
Arg Tyr Asp Ile Ala Ser Ile Lys Ala Phe Asn Gly Met Leu Met Gln
            995                 1000                1005
Phe Leu Glu Arg Pro Asp Tyr Val Ile Lys Ser Leu Pro Phe Thr Pro
    1010                1015                1020
Ala Lys Pro Leu Trp Gly Tyr Leu Pro Gly Gly Cys Gly Tyr Asp Asp
1025                1030                1035                1040
Ala Val Ala Cys Thr Thr Arg Tyr His Tyr Ala Met Leu Ile Glu Asp
                1045                1050                1055
Glu Leu Asn Ser Gly Asn Trp Glu Trp Ser Ser Tyr Ile Lys Phe Tyr
                    1060                1065                1070
Glu Leu Trp Ala Asp Ile Asp Gly Thr Arg Val Asp Ser Lys Ser Ser
            1075                1080                1085
Asp Val Asp Val Gln Val Asp Ser Tyr Val Lys Gly Asn Glu Leu Phe
    1090                1095                1100
Val Ile Leu Asn Asn Leu Glu Ala Ala Asp Thr Thr Val Asn Leu Asp
1105                1110                1115                1120
Val Ser Gly Ile Ala Ser Val Gln Asn Val Glu Leu Arg Asn Met His
                1125                1130                1135
Phe Asp Ile Gln Glu Thr His Leu Asp Arg His His Met Ser Ala Ala
                    1140                1145                1150
Pro Lys Thr Val Thr Leu Ala Ala Asp Ala Thr Val Val Leu Arg Tyr
            1155                1160                1165
Thr Leu Ala Ser Ser Val Ala Val Asn Asn Thr Val Val Glu Lys Lys
    1170                1175                1180
```

```
Tyr Phe Gly Glu Ser Val Ser Gly Gly Ile Glu Pro His Arg Ile Ser
            1185                1190                1195                1200

Val Ala Gly Gly Ala Lys Thr Leu Tyr Ile Asn Asn Val Ser Val Pro
        1205                1210                1215

Ser Gly Tyr Ser Glu Ala Ile Leu Arg Leu Thr Val Ser Leu Tyr Pro
        1220                1225                1230

Asp Glu Asp Asp Lys Val Gly Gly His Leu Ser Leu Asp Ser Ile Thr
        1235                1240                1245

Val Asn Gly Thr Ala Ile Glu Ala Pro Ile Asp Trp Lys Gly Pro Lys
    1250                1255                1260

Ala Asn Arg Ala Glu Arg Phe Phe Gly Val Leu Asp Ile Pro Val Pro
1265                1270                1275                1280

Val Glu Leu Leu Gln Ser Thr Asn Thr Ile Ala Val Asp Phe Arg His
            1285                1290                1295

Asn Gly Glu Leu Thr Val Ala Asn Leu Ile Val Ser Glu Phe Thr Ser
        1300                1305                1310

Glu Pro Asn Arg
    1315

<210> SEQ ID NO 4
<211> LENGTH: 4008
<212> TYPE: DNA
<213> ORGANISM: Saccharophagus degradans

<400> SEQUENCE: 4
atgcgaaatt taaataaaaa taaagtacat atattgcgag cagcaattgc tgcaagcatg        60
agtgtactgc cacttgctgc tggtgccgcc gattatgtaa tcgaagcgga aaactttgtg       120
gcgcagggtg gcacctacgt ggacggacaa cccaataaag ttagcgttta tagtgttaat       180
ggcgcaaccg ctattaacta tgtaaaccga gcagactata ccgattacca aattaatgta       240
gctacccacg ttattacaa tgtgcaatat gctattggta catctgtagc cagtggtgcg        300
gctattgagt tactcgtaca aaatggcagt agctgggaat cgcagggggca acaaatgtg       360 cctgttggtc attgggatag ttttcagcct ttaaatgcaa gtcatgaggt aatcttacct       420
gcgggcactg taaatttacg tgtatatggt gcggggtcta atgattggca atggaattta       480
gattctattt ctctcaccct agagagcgct attaaccctc agcctgatcc agatcccgat       540
cctagccctc aattagtaaa aactgaagcc gaagccttta tgcgcagag cggaactttc        600 gccgatggtc agcctacacc ggtgagtatt tatactgtta tggaaaaac ggcgataaac         660 tttgtaaaca aggcgatgc cgttgaatac aacttagttg ctccggctgc cggttcatac        720
gcattaaaat actctattgg taccagtgtt gcttccggta gtgaagtaga gttttttgtt       780
ttaaaaaata atgtttgggt ttcacagggt aaaacacctg tgccggctgt tggttgggat       840
aactttacct ctgttgccag tgcgcaaacc gttgagttag ctgctggctc aaataaagtt       900
aaacttgttg gtgctggcac taatgactgg cagtggaatt tagatttctt cgagctcacc       960
ctgggaaatg ttgaaccaga accagaacca gaaccagagc cagaaccaga gccagagcca      1020
gagccagagc cagagccaga gccagagcca gaaccagagc cagaaccaga acctcagcca      1080
gagcccgatg gcgaccccgt tcctgtaagt ggctcgtttta agttagaagc cgagcacttt      1140
caaaaggtag tggcgaagt acaaatttat tctctatcgc caggcaacgc ggttaattat       1200
tttaacagcg gtgattacct agagttctat gtcgacttag atgcaggcgg tttgtatgaa      1260
gccagcttca gagtgggtac tggtgtggcc tctgatgtag ccgttggcct aatggttaca      1320
```

```
gatcacaaag gtgacttaac attgaagagt gttacacccg taacggatca aggtggttgg    1380
gatgcatttt ataatctcac cgcgcaaagc cagctgaata tttatagtgg tataaacact    1440
attcgtatta caggtgcagg gtctgctgat tttcaattta atattgatag catcactttg    1500
actcgtgttg ggccaattaa cccagcgcta gatggggata acgatggtgt accagataca    1560
tcagataact gcccaagtag ccccgccaat gaaacggcaa acgctgaagg ttgtgtaccg    1620
tcgcaattag acactgatga agatggtatt aacgataaaa ttgatcaatg cgatgcaaca    1680
ccagcaggag attttgttga cgccttaggt tgtacaagta ctggtggtga cgacgatgac    1740
tttgatggcg ttttaaacgg tgccgatcaa tgtggtaata cgccttacgg tatgaacgtt    1800
aatgcccaag ggtgtagtgt gttttctgga agcgatgccg ataacgacgg tgttgcaaac    1860
agcgaagaca cctgcgcaaa tacgcctgcg ttagaattcg ctaacgaaca gggttgttct    1920
tcgtcgcaag tggcaaatac acatgttgtt aacgtaagtg ttaatgctaa ctttaagcgc    1980
tctgtaaatg gtgtatttga tttcggccgc cgtcgtcaca tgactgctca cacggctatt    2040
cacgagccag attgggtagg gcataccgat aagttaaatt acctattcaa cacccctagat   2100 gtttacatgg ggcgtgataa cggttcggca acgtggaagt ttaacgacac taccgaagat    2160
cctaataagc ccaactggcc aaatatggac tacatggttg agcgcggtaa agggttgcga    2220
gaagcgcatg accaaaaccc attgttcaaa cgttttagtg ccgaaaaaca attattaatt    2280
gccggtacta cccgcacgc gttgtaccct accttaagtt ggttccctaa cgcgtttacc    2340
tggagcggtt ggcagcctaa aaatattgaa acatctgcag catgggtggg acagtatatg    2400
gagcattatt ttgcgaacgc ttcaaacggc tatgtaggtg agcagctgcc cgagtattgg    2460
gaagtagtaa acgaaccgga tatgaaaatg aaaaccggtc agtttatggt aaccaatcaa    2520
gaggccatct gggagtacca caacttggtt gcgcaagaaa ttcgcgatca ccttggcgca    2580
gaagcacctc ccattggtgg tatgacttgg ggacagcacg acttctatcg tcgcgatggc    2640 attttcgcgtt ttgccgatga ctcttacgat cagtggatta caaacgatga ccaagtattg    2700
caggcagaag ctcgcgcttt ttatcgcaat gctatggcta ccactgtaga tgatactcgc    2760
gaccaagatt ggtatcagtg ggatgtaatg tggaaaggct ttatggatgc ggccggcgac    2820
aacatggact tttactctgt gcacatttat gactggccag gagagaatgt tggtgatact    2880
actgttgttc gtcgtggtgg gcacacctct gccatgctag aaatgatgga gtggtacgat    2940
gtaaaacgta acggctttaa caaccgtaaa ccaatcgtac tttcggagta cggctcagtt    3000
aatgggcttt gggataatcg cgcccacgaa gagcgttacg atattgcaag tatcaaagcg    3060
tttaatggca tgttaatgca gttcctagag cgcccagact acgtaataaa atctctacca    3120
tttactcctg ccaaacctttt gtggggctac ctgcctggtg gttgtggcta cgatgatgca    3180
gtggcctgta ctactcgtta ccattacgcc atgttaattg aggatgagct caacagtggt    3240
aattgggaat ggtcttctta cataaagttc tacgagttgt gggcagatat agacggcact    3300
cgtgtcgatt ctaaatcgtc tgatgtggat gtacaggttg actcttatgt gaaaggtaac    3360
gagctgttcg ttattcttaa caacttagaa gcggccgaca caacggtcaa ccttgatgta    3420
agcggtatag ccagcgtgca aaatgttgaa ttgcgcaaca tgcatttcga tattcaagag    3480
acgcatcttg atcgccatca tatgagcgct gcacctaaaa cggttactct agccgccgat    3540
gcgactgtgg tattacgtta tacgcttgca agcagtgttg cggtaaataa caccgtagta    3600
gagaaaaagt actttggtga gagtgtaagt ggcggtatag aaccacatcg catttcggtt    3660
gcaggcggtg ctaaaacgct ttatatcaat aacgtttcgg ttccaagtgg ctacagcgaa    3720
```

```
gcaatattgc gcttaactgt atcgctttac ccagacgaag acgataaagt gggcggccat    3780
ttaagcctag atagcattac tgttaacggc actgccatag aggcgccaat agattggaaa    3840
ggcccgaaag caaaccgtgc agaacgattc ttcggcgtac ttgatattcc agtacctgta    3900
gaattattgc aatctactaa taccatcgca gtggacttcc gccacaatgg tgagttaacg    3960
gtagcaaact taattgtgtc ggaatttact tctgagccaa atagataa              4008
```

<210> SEQ ID NO 5
<211> LENGTH: 140
<212> TYPE: PRT
<213> ORGANISM: Saccharophagus degradans

<400> SEQUENCE: 5

```
Gly Ala Ala Asp Tyr Val Ile Glu Ala Glu Asn Phe Val Ala Gln Gly
  1               5                  10                  15

Gly Thr Tyr Val Asp Gly Gln Pro Asn Lys Val Ser Val Tyr Ser Val
                 20                  25                  30

Asn Gly Ala Thr Ala Ile Asn Tyr Val Asn Arg Ala Asp Tyr Thr Asp
             35                  40                  45

Tyr Gln Ile Asn Val Ala Thr His Gly Tyr Tyr Asn Val Gln Tyr Ala
         50                  55                  60

Ile Gly Thr Ser Val Ala Ser Gly Ala Ala Ile Glu Leu Leu Val Gln
 65                  70                  75                  80

Asn Gly Ser Ser Trp Glu Ser Gln Gly Gln Thr Asn Val Pro Val Gly
                 85                  90                  95

His Trp Asp Ser Phe Gln Pro Leu Asn Ala Ser His Glu Val Ile Leu
                100                 105                 110

Pro Ala Gly Thr Val Asn Leu Arg Val Tyr Gly Ala Gly Ser Asn Asp
            115                 120                 125

Trp Gln Trp Asn Leu Asp Ser Ile Ser Leu Thr Leu
        130                 135                 140
```

<210> SEQ ID NO 6
<211> LENGTH: 141
<212> TYPE: PRT
<213> ORGANISM: Saccharophagus degradans

<400> SEQUENCE: 6

```
Pro Ser Pro Gln Leu Val Lys Thr Glu Ala Glu Ala Phe Asn Ala Gln
  1               5                  10                  15

Ser Gly Thr Phe Ala Asp Gly Gln Pro Thr Pro Val Ser Ile Tyr Thr
                 20                  25                  30

Val Asn Gly Lys Thr Ala Ile Asn Phe Val Asn Lys Gly Asp Ala Val
             35                  40                  45

Glu Tyr Asn Leu Val Ala Pro Ala Ala Gly Ser Tyr Ala Leu Lys Tyr
         50                  55                  60

Ser Ile Gly Thr Ser Val Ala Ser Gly Ser Val Glu Phe Phe Val
 65                  70                  75                  80

Leu Lys Asn Asn Val Trp Val Ser Gln Gly Lys Thr Pro Val Pro Ala
                 85                  90                  95

Val Gly Trp Asp Asn Phe Thr Ser Ala Ser Ala Gln Thr Val Glu
                100                 105                 110

Leu Ala Ala Gly Ser Asn Lys Val Lys Leu Val Gly Ala Gly Thr Asn
            115                 120                 125

Asp Trp Gln Trp Asn Leu Asp Phe Phe Glu Leu Thr Leu
```

```
                  130               135               140

<210> SEQ ID NO 7
<211> LENGTH: 135
<212> TYPE: PRT
<213> ORGANISM: Saccharophagus degradans

<400> SEQUENCE: 7

Pro Val Ser Gly Ser Phe Lys Leu Glu Ala Glu His Phe Gln Lys Val
  1               5                  10                  15

Gly Gly Glu Val Gln Ile Tyr Ser Leu Ser Pro Gly Asn Ala Val Asn
             20                  25                  30

Tyr Phe Asn Ser Gly Asp Tyr Leu Glu Phe Tyr Val Asp Leu Asp Ala
         35                  40                  45

Gly Gly Leu Tyr Glu Ala Ser Phe Arg Val Gly Thr Gly Val Ala Ser
     50                  55                  60

Asp Val Ala Val Gly Leu Met Val Thr Asp His Lys Gly Asp Leu Thr
 65                  70                  75                  80

Leu Lys Ser Val Thr Pro Val Thr Asp Gln Gly Gly Trp Asp Ala Phe
                 85                  90                  95

Tyr Asn Leu Thr Ala Gln Ser Gln Leu Asn Ile Tyr Ser Gly Ile Asn
            100                 105                 110

Thr Ile Arg Ile Thr Gly Ala Gly Ser Ala Asp Phe Gln Phe Asn Ile
        115                 120                 125

Asp Ser Ile Thr Leu Thr Arg
    130                 135

<210> SEQ ID NO 8
<211> LENGTH: 8
<212> TYPE: PRT
<213> ORGANISM: Saccharophagus degradans

<400> SEQUENCE: 8

Pro Gln Pro Asp Pro Asp Pro Asp
  1               5

<210> SEQ ID NO 9
<211> LENGTH: 684
<212> TYPE: PRT
<213> ORGANISM: Saccharophagus degradans

<400> SEQUENCE: 9

Val Ser Val Asn Ala Asn Phe Lys Arg Ser Val Asn Gly Val Phe Asp
  1               5                  10                  15

Phe Gly Arg Arg Arg His Met Thr Ala His Thr Ala Ile His Glu Pro
             20                  25                  30

Asp Trp Val Gly His Thr Asp Lys Leu Asn Tyr Leu Phe Asn Thr Leu
         35                  40                  45

Asp Val Tyr Met Gly Arg Asp Asn Gly Ser Ala Thr Trp Lys Phe Asn
     50                  55                  60

Asp Thr Thr Glu Asp Pro Asn Lys Pro Asn Trp Pro Asn Met Asp Tyr
 65                  70                  75                  80

Met Val Glu Arg Gly Lys Gly Leu Arg Glu Ala His Asp Gln Asn Pro
                 85                  90                  95

Leu Phe Lys Arg Phe Ser Ala Glu Lys Gln Leu Leu Ile Ala Gly Thr
            100                 105                 110

Asn Pro His Ala Leu Tyr Pro Thr Leu Ser Trp Phe Pro Asn Ala Phe
        115                 120                 125
```

```
Thr Trp Ser Gly Trp Gln Pro Lys Asn Ile Glu Thr Ser Ala Ala Trp
    130                 135                 140

Val Gly Gln Tyr Met Glu His Tyr Phe Ala Asn Ala Ser Asn Gly Tyr
145                 150                 155                 160

Val Gly Glu Gln Leu Pro Glu Tyr Trp Glu Val Val Asn Glu Pro Asp
                165                 170                 175

Met Lys Met Lys Thr Gly Gln Phe Met Val Thr Asn Gln Glu Ala Ile
                180                 185                 190

Trp Glu Tyr His Asn Leu Val Ala Gln Glu Ile Arg Asp His Leu Gly
                195                 200                 205

Ala Glu Ala Pro Pro Ile Gly Gly Met Thr Trp Gly Gln His Asp Phe
210                 215                 220

Tyr Arg Arg Asp Gly Ile Ser Arg Phe Ala Asp Asp Ser Tyr Asp Gln
225                 230                 235                 240

Trp Ile Thr Asn Asp Asp Gln Val Leu Gln Ala Glu Ala Arg Ala Phe
                245                 250                 255

Tyr Arg Asn Ala Met Ala Thr Thr Val Asp Asp Thr Arg Asp Gln Asp
                260                 265                 270

Trp Tyr Gln Trp Asp Val Met Trp Lys Gly Phe Met Asp Ala Ala Gly
                275                 280                 285

Asp Asn Met Asp Phe Tyr Ser Val His Ile Tyr Asp Trp Pro Gly Glu
290                 295                 300

Asn Val Gly Asp Thr Thr Val Val Arg Arg Gly Gly His Thr Ser Ala
305                 310                 315                 320

Met Leu Glu Met Met Glu Trp Tyr Asp Val Lys Arg Asn Gly Phe Asn
                325                 330                 335

Asn Arg Lys Pro Ile Val Leu Ser Glu Tyr Gly Ser Val Asn Gly Ala
                340                 345                 350

Trp Asp Asn Arg Ala His Glu Glu Arg Tyr Asp Ile Ala Ser Ile Lys
                355                 360                 365

Ala Phe Asn Gly Met Leu Met Gln Phe Leu Glu Arg Pro Asp Tyr Val
370                 375                 380

Ile Lys Ser Leu Pro Phe Thr Pro Ala Lys Pro Leu Trp Gly Tyr Leu
385                 390                 395                 400

Pro Gly Gly Cys Gly Tyr Asp Asp Ala Val Ala Cys Thr Thr Arg Tyr
                405                 410                 415

His Tyr Ala Met Leu Ile Glu Asp Glu Leu Asn Ser Gly Asn Trp Glu
                420                 425                 430

Trp Ser Ser Tyr Ile Lys Phe Tyr Glu Leu Trp Ala Asp Ile Asp Gly
                435                 440                 445

Thr Arg Val Asp Ser Lys Ser Ser Asp Val Asp Val Gln Val Asp Ser
                450                 455                 460

Tyr Val Lys Gly Asn Glu Leu Phe Val Ile Leu Asn Asn Leu Glu Ala
465                 470                 475                 480

Ala Asp Thr Thr Val Asn Leu Asp Val Ser Gly Ile Ala Ser Val Gln
                485                 490                 495

Asn Val Glu Leu Arg Asn Met His Phe Asp Ile Gln Glu Thr His Leu
                500                 505                 510

Asp Arg His His Met Ser Ala Ala Pro Lys Thr Val Thr Leu Ala Ala
                515                 520                 525

Asp Ala Thr Val Val Leu Arg Tyr Thr Leu Ala Ser Ser Val Ala Val
530                 535                 540
```

```
Asn Asn Thr Val Val Glu Lys Lys Tyr Phe Gly Glu Ser Val Ser Gly
545                 550                 555                 560

Gly Ile Glu Pro His Arg Ile Ser Val Ala Gly Ala Lys Thr Leu
                565                 570                 575

Tyr Ile Asn Asn Val Ser Val Pro Ser Gly Tyr Ser Glu Ala Ile Leu
                580                 585                 590

Arg Leu Thr Val Ser Leu Tyr Pro Asp Glu Asp Lys Val Gly Gly
                595                 600                 605

His Leu Ser Leu Asp Ser Ile Thr Val Asn Gly Thr Ala Ile Glu Ala
                610                 615                 620

Pro Ile Asp Trp Lys Gly Pro Lys Ala Asn Arg Ala Glu Arg Phe Phe
625                 630                 635                 640

Gly Val Leu Asp Ile Pro Val Pro Val Glu Leu Leu Gln Ser Thr Asn
                645                 650                 655

Thr Ile Ala Val Asp Phe Arg His Asn Gly Glu Leu Thr Val Ala Asn
                660                 665                 670

Leu Ile Val Ser Glu Phe Thr Ser Glu Pro Asn Arg
                675                 680

<210> SEQ ID NO 10
<211> LENGTH: 124
<212> TYPE: PRT
<213> ORGANISM: Saccharophagus degradans

<400> SEQUENCE: 10

Thr Gly Lys Glu Gly Ser Ala Val Ala Gly Asp Thr Phe Thr Gly Phe
1               5                   10                  15

Asn Pro Ser Gly Ala Asn Asn Ile Asn Tyr Asn Thr Leu Gly Asp Trp
                20                  25                  30

Ala Asp Tyr Thr Val Asn Phe Pro Ala Ala Gly Asn Tyr Thr Val Asn
                35                  40                  45

Leu Ile Ala Ala Ser Pro Val Thr Ser Gly Leu Gly Ala Asp Ile Leu
        50                  55                  60

Val Asp Ser Ser Tyr Ala Gly Thr Ile Pro Val Ser Ser Thr Gly Ala
65                  70                  75                  80

Trp Glu Ile Tyr Asn Thr Phe Ser Leu Pro Ser Ser Ile Tyr Ile Ala
                85                  90                  95

Ser Ala Gly Asn His Thr Ile Arg Val Gln Ser Ser Gly Ser Ala
                100                 105                 110

Trp Gln Trp Asn Gly Asp Glu Leu Arg Phe Thr Gln
        115                 120

<210> SEQ ID NO 11
<211> LENGTH: 139
<212> TYPE: PRT
<213> ORGANISM: Saccharophagus degradans

<400> SEQUENCE: 11

Pro Ser Thr Ala Ser Ile Ala Val Glu Ala Glu Asn Phe Asn Ala Val
1               5                   10                  15

Gly Gly Thr Phe Ser Asp Gly Gln Ala Gln Pro Val Ser Val Tyr Thr
                20                  25                  30

Val Asn Gly Asn Thr Ala Ile Asn Tyr Val Asn Gln Gly Asp Tyr Ala
                35                  40                  45

Asp Tyr Thr Ile Ala Val Ala Gln Ala Gly Asn Tyr Thr Ile Ser Tyr
        50                  55                  60
```

```
Gln Ala Gly Ser Gly Val Thr Gly Gly Ser Ile Glu Phe Leu Val Asn
 65                  70                  75                  80

Glu Asn Gly Ser Trp Ala Ser Lys Thr Val Thr Ala Val Pro Asn Gln
                 85                  90                  95

Gly Trp Asp Asn Phe Gln Pro Leu Asn Gly Gly Ser Val Tyr Leu Ser
            100                 105                 110

Ala Gly Thr His Gln Val Arg Leu His Gly Ala Gly Ser Asn Asn Trp
        115                 120                 125

Gln Trp Asn Leu Asp Lys Phe Thr Leu Ser Asn
130                 135
```

<210> SEQ ID NO 12
<211> LENGTH: 259
<212> TYPE: PRT
<213> ORGANISM: Saccharophagus degradans

<400> SEQUENCE: 12

```
Thr Trp Glu Leu Gln Ser Leu Ser Asp Asp Phe Asn Tyr Ala Ala Pro
  1               5                  10                  15

Ala Asn Gly Lys Arg Thr Thr Phe Tyr Ser Arg Trp Ser Glu Gly Phe
                 20                  25                  30

Ile Asn Ala Trp Leu Gly Pro Gly Gln Thr Glu Phe Tyr Gly Pro Asn
            35                  40                  45

Ala Ser Val Glu Gly Gly His Leu Ile Ile Lys Ala Thr Arg Lys Pro
    50                  55                  60

Gly Thr Thr Gln Ile Tyr Thr Gly Ala Ile His Ser Asn Glu Ser Phe
 65                  70                  75                  80

Thr Tyr Pro Leu Tyr Leu Glu Ala Arg Thr Lys Ile Thr Asn Leu Thr
                 85                  90                  95

Leu Ala Asn Ala Phe Trp Leu Ser Ser Asp Ser Thr Glu Glu Ile
            100                 105                 110

Asp Val Leu Glu Ser Tyr Gly Ser Asp Arg Ala Thr Glu Thr Trp Phe
        115                 120                 125

Asp Glu Arg Leu His Leu Ser His His Val Phe Ile Arg Gln Pro Phe
    130                 135                 140

Gln Asp Tyr Gln Pro Lys Asp Ala Gly Ser Trp Tyr Pro Asn Pro Asp
145                 150                 155                 160

Gly Gly Thr Trp Arg Asp Gln Phe Phe Arg Ile Gly Val Tyr Trp Ile
                165                 170                 175

Asp Pro Trp Thr Leu Glu Tyr Tyr Val Asn Gly Glu Leu Val Arg Thr
            180                 185                 190

Val Ser Gly Pro Glu Met Ile Asp Pro Tyr Gly Tyr Thr Asn Gly Thr
        195                 200                 205

Gly Leu Ser Lys Pro Met Gln Val Ile Phe Asp Ala Glu His Gln Pro
    210                 215                 220

Trp Arg Asp Glu Gln Gly Thr Ala Pro Thr Asp Ala Glu Leu Ala
225                 230                 235                 240

Asp Ser Ser Arg Asn Gln Phe Leu Ile Asp Trp Val Arg Phe Tyr Lys
                245                 250                 255

Pro Val Ala
```

<210> SEQ ID NO 13
<211> LENGTH: 32
<212> TYPE: PRT
<213> ORGANISM: Saccharophagus degradans

<400> SEQUENCE: 13

```
Pro Glu Pro Glu Pro Glu Pro Glu Pro Glu Pro Glu Pro Glu Pro Glu
 1               5                  10                  15
Pro Glu Pro Glu Pro Glu Pro Glu Pro Glu Pro Glu Pro Glu Pro Glu
                20                  25                  30
```

<210> SEQ ID NO 14
<211> LENGTH: 201
<212> TYPE: PRT
<213> ORGANISM: Aeromonas sp.

<400> SEQUENCE: 14

```
Ser Ala Gly Ser Gly Lys Thr Trp Gln Leu Gln Thr Val Ser Asp Gln
 1               5                  10                  15

Phe Asn Tyr Gln Ala Gly Thr Ser Asn Lys Pro Ala Ala Phe Thr Asn
                20                  25                  30

Arg Trp Asn Ala Ser Tyr Ile Asn Ala Trp Leu Gly Pro Gly Asp Thr
             35                  40                  45

Glu Phe Ser Ser Gly His Ser Tyr Thr Thr Gly Gly Ala Leu Gly Leu
 50                  55                  60

Gln Ala Thr Glu Lys Ala Gly Thr Asn Lys Val Leu Ser Gly Ile Val
 65                  70                  75                  80

Ser Ser Lys Ala Thr Phe Thr Tyr Pro Leu Tyr Leu Glu Ala Met Val
                 85                  90                  95

Lys Pro Ser Asn Asn Thr Met Ala Asn Ala Val Trp Met Leu Ser Ser
            100                 105                 110

Asp Ser Thr Gln Glu Ile Asp Ala Met Glu Ser Tyr Gly Ser Asp Arg
        115                 120                 125

Val Gly Gln Glu Trp Phe Asp Gln Arg Met His Val Ser His His Val
    130                 135                 140

Phe Ile Arg Glu Pro Phe Gln Asp Tyr Gln Pro Lys Asp Ala Gly Ala
145                 150                 155                 160

Trp Val Tyr Asn Ser Gly Glu Thr Tyr Arg Asn Lys Phe Arg Arg Tyr
                165                 170                 175

Gly Val His Trp Lys Asp Ala Trp Asn Leu Asp Tyr Tyr Ile Asp Gly
            180                 185                 190

Val Leu Val Arg Ser Val Ser Gly Pro
        195                 200
```

<210> SEQ ID NO 15
<211> LENGTH: 209
<212> TYPE: PRT
<213> ORGANISM: Pseudoalteromonas atlantica

<400> SEQUENCE: 15

```
Trp Ser Ser Phe Ser Ile Pro Ala Gln Ala Gly Ala Gly Lys Ser Trp
 1               5                  10                  15

Gln Leu Gln Ser Val Ser Asp Glu Phe Asn Tyr Ile Ala Gln Pro Asn
                20                  25                  30

Asn Lys Pro Ala Ala Phe Asn Asn Arg Trp Asn Ala Ser Tyr Ile Asn
             35                  40                  45

Ala Trp Leu Gly Pro Gly Asp Thr Glu Phe Ser Ala Gly His Ser Tyr
 50                  55                  60

Thr Thr Gly Gly Ala Leu Gly Leu Gln Ala Thr Glu Lys Ala Gly Thr
 65                  70                  75                  80

Asn Lys Val Leu Ser Gly Ile Ile Ser Ser Lys Ala Thr Phe Thr Tyr
```

```
                85                  90                  95
Pro Leu Tyr Leu Glu Ala Met Val Lys Pro Thr Asn Asn Thr Met Ala
            100                 105                 110

Asn Ala Val Trp Met Leu Ser Ala Asp Ser Thr Gln Glu Ile Asp Ala
        115                 120                 125

Met Glu Ser Tyr Gly Ser Asp Arg Ile Gly Gln Glu Trp Phe Asp Gln
    130                 135                 140

Arg Met His Val Ser His His Ile Phe Ile Arg Asp Pro Phe Gln Asp
145                 150                 155                 160

Tyr Gln Pro Lys Asp Ala Gly Ser Trp Val Tyr Asn Asn Gly Glu Thr
                165                 170                 175

Tyr Arg Asn Lys Phe Arg Arg Tyr Gly Val His Trp Lys Asp Ala Trp
            180                 185                 190

Asn Leu Asp Tyr Tyr Ile Asp Gly Val Leu Val Arg Ser Val Ser Gly
        195                 200                 205

Pro

<210> SEQ ID NO 16
<211> LENGTH: 195
<212> TYPE: PRT
<213> ORGANISM: Zobellia galactanvorans

<400> SEQUENCE: 16

Gly Met Thr Trp Gln Leu Gln Asp Asn Val Ser Asp Ser Phe Asn Tyr
  1               5                  10                  15

Thr Ser Ser Glu Gly Asn Arg Pro Thr Ala Phe Thr Ser Lys Trp Lys
             20                  25                  30

Pro Ser Tyr Ile Asn Gly Trp Thr Gly Pro Gly Ser Thr Ile Phe Asn
         35                  40                  45

Ala Ala Gln Ala Trp Thr Asn Gly Ser Gln Leu Ala Ile Gln Ala Gln
     50                  55                  60

Pro Ala Gly Asn Gly Lys Ser Tyr Asn Gly Ile Ile Thr Ser Lys Asn
 65                  70                  75                  80

Lys Ile Gln Tyr Pro Val Tyr Met Glu Ile Lys Ala Lys Ile Met Asp
                 85                  90                  95

Gln Val Leu Ala Asn Ala Phe Trp Thr Leu Thr Asp Asp Glu Thr Gln
            100                 105                 110

Glu Ile Asp Ile Met Glu Gly Tyr Gly Ser Asp Arg Gly Gly Thr Trp
        115                 120                 125

Phe Ala Gln Arg Met His Leu Ser His His Thr Phe Ile Arg Asn Pro
    130                 135                 140

Phe Thr Asp Tyr Gln Pro Met Gly Asp Ala Thr Trp Tyr Tyr Asn Gly
145                 150                 155                 160

Gly Thr Pro Trp Arg Ser Ala Tyr His Arg Tyr Gly Cys Tyr Trp Lys
                165                 170                 175

Asp Pro Phe Thr Leu Glu Tyr Tyr Ile Asp Gly Val Lys Val Arg Thr
            180                 185                 190

Val Thr Arg
        195

<210> SEQ ID NO 17
<211> LENGTH: 210
<212> TYPE: PRT
<213> ORGANISM: Microbulbifer sp.

<400> SEQUENCE: 17
```

Trp Asp Gly Thr Pro Val Pro Ala Asp Ala Gly Pro Gly Asn Thr Trp
1               5                   10                  15

Glu Leu His Pro Leu Ser Asp Asp Phe Asn Tyr Ser Ala Pro Ala Ser
            20                  25                  30

Gly Lys Ser Ala Thr Phe Phe Glu Arg Trp Ser Glu Gly Phe Ile Asn
        35                  40                  45

Pro Trp Leu Gly Pro Gly Glu Thr Glu Tyr Tyr Gly Pro Asn Ser Ser
    50                  55                  60

Val Glu Ser Gly Asn Leu Val Ile Lys Ala Ser Arg Lys Ala Gly Thr
65                  70                  75                  80

Thr Lys Ile His Ala Gly Ala Ile His Ser Asn Glu Ser Val Thr Tyr
                85                  90                  95

Pro Leu Tyr Met Glu Ala Arg Val Gln Val Thr Asn Leu Thr Met Ala
            100                 105                 110

Asn Ala Phe Trp Leu Leu Ser Ser Asp Ser Thr Gln Glu Ile Asp Val
        115                 120                 125

Leu Glu Ser Tyr Gly Ser Asp Arg Pro Ser Glu Thr Trp Phe Asp Glu
    130                 135                 140

Arg Leu His Leu Ser His His Val Phe Ile Arg Glu Pro Phe Gln Asp
145                 150                 155                 160

Tyr Gln Pro Lys Asp Asp Gly Ser Trp Tyr Pro Asn Pro Asn Gly Gly
                165                 170                 175

Thr Trp Arg Asp Gln Trp Ile Arg Ile Gly Thr Tyr Trp Val Asp Pro
            180                 185                 190

Trp Thr Leu Glu Tyr Tyr Val Asn Gly Glu His Val Arg Thr Val Thr
        195                 200                 205

Gly Pro
    210

<210> SEQ ID NO 18
<211> LENGTH: 196
<212> TYPE: PRT
<213> ORGANISM: Saccharophagus degradans

<400> SEQUENCE: 18

Thr Trp Glu Leu Gln Ser Leu Ser Asp Asp Phe Asn Tyr Ala Ala Pro
1               5                   10                  15

Ala Asn Gly Lys Arg Thr Thr Phe Tyr Ser Arg Trp Ser Glu Gly Phe
            20                  25                  30

Ile Asn Ala Trp Leu Gly Pro Gly Gln Thr Glu Phe Tyr Gly Pro Asn
        35                  40                  45

Ala Ser Val Glu Gly Gly His Leu Ile Ile Lys Ala Thr Arg Lys Pro
    50                  55                  60

Gly Thr Thr Gln Ile Tyr Thr Gly Ala Ile His Ser Asn Glu Ser Phe
65                  70                  75                  80

Thr Tyr Pro Leu Tyr Leu Glu Ala Arg Thr Lys Ile Thr Asn Leu Thr
                85                  90                  95

Leu Ala Asn Ala Phe Trp Leu Leu Ser Ser Asp Ser Thr Glu Glu Ile
            100                 105                 110

Asp Val Leu Glu Ser Tyr Gly Ser Asp Arg Ala Thr Glu Thr Trp Phe
        115                 120                 125

Asp Glu Arg Leu His Leu Ser His His Val Phe Ile Arg Gln Pro Phe
    130                 135                 140

Gln Asp Tyr Gln Pro Lys Asp Ala Gly Ser Trp Tyr Pro Asn Pro Asp

```
                145                 150                 155                 160
Gly Gly Thr Trp Arg Asp Gln Phe Phe Arg Ile Gly Val Tyr Trp Ile
                    165                 170                 175
Asp Pro Trp Thr Leu Glu Tyr Tyr Val Asn Gly Glu Leu Val Arg Thr
                180                 185                 190
Val Ser Gly Pro
        195
```

<210> SEQ ID NO 19
<211> LENGTH: 208
<212> TYPE: PRT
<213> ORGANISM: Pseudomonas sp.

<400> SEQUENCE: 19

```
Asp Gly Leu Ala Val Pro Ala Asp Ala Gly Asp Gly Lys Thr Trp Gln
 1               5                  10                  15
Leu Gln Ser Ser Leu Ser Asp Asp Phe Ser Tyr Ser Ala Pro Ala Glu
            20                  25                  30
Gly Lys Ser Gln Ala Phe Tyr Glu Arg Trp Ser Glu Gly Phe Ile Asn
        35                  40                  45
Ala Trp Gln Gly Pro Gly Leu Thr Asp Tyr His Asn Pro Asn Ser Arg
    50                  55                  60
Val Glu Asn Gly Glu Leu Val Ile Thr Ala Thr Arg Lys Ala Gly Thr
65                  70                  75                  80
Asn Glu Val Tyr Thr Gly Ala Ile His Thr Asn Glu Ser Val Gln Tyr
                85                  90                  95
Pro Val Tyr Ile Glu Thr Ser Ser Lys Ile Met Asp Gln Val Leu Ala
            100                 105                 110
Asn Ala Val Trp Met Leu Ser Ser Asp Ser Thr Gln Glu Ile Asp Ile
        115                 120                 125
Val Glu Ala Tyr Gly Ser Ser Arg Ala Asp Gln Thr Trp Phe Ala Glu
    130                 135                 140
Arg Met His Leu Ala His His Val Phe Ile Arg Asp Pro Phe Gln Asp
145                 150                 155                 160
Tyr Gln Pro Lys Asp Ala Gly Ala Trp Tyr Ala Asp Gly Arg Leu Trp
                165                 170                 175
Arg Glu Gln Tyr Ser Arg Val Gly Val Tyr Trp Arg Asp Pro Trp His
            180                 185                 190
Leu Glu Tyr Tyr Ile Asp Gly Gln Leu Val Arg Thr Val Ser Gly Val
        195                 200                 205
```

<210> SEQ ID NO 20
<211> LENGTH: 209
<212> TYPE: PRT
<213> ORGANISM: Microbulbifer sp.

<400> SEQUENCE: 20

```
Asp Gly Val Pro Val Pro Ala Asn Pro Gly Ser Gly Lys Thr Trp Glu
 1               5                  10                  15
Leu His Pro Leu Ser Asp Asp Phe Asn Tyr Glu Ala Pro Ala Ala Gly
            20                  25                  30
Lys Ser Thr Arg Phe Tyr Glu Arg Trp Lys Glu Gly Phe Ile Asn Pro
        35                  40                  45
Trp Thr Gly Pro Gly Leu Thr Glu Trp His Pro His Tyr Ser Tyr Val
    50                  55                  60
Ser Gly Gly Lys Leu Ala Ile Thr Ser Gly Arg Lys Pro Gly Thr Asn
```

```
                65                  70                  75                  80
Gln Val Tyr Leu Gly Ser Ile Thr Ser Lys Ala Pro Leu Thr Tyr Pro
                85                  90                  95

Val Tyr Met Glu Ala Arg Ala Lys Leu Ser Asn Met Val Leu Ala Ser
            100                 105                 110

Asp Phe Trp Phe Leu Ser Ala Asp Ser Thr Glu Ile Asp Val Ile
            115                 120                 125

Glu Ala Tyr Gly Ser Asp Arg Pro Gly Gln Glu Trp Tyr Ala Glu Arg
        130                 135                 140

Leu His Leu Ser His His Val Phe Ile Arg Asp Pro Phe Gln Asp Tyr
145                 150                 155                 160

Gln Pro Thr Asp Ala Gly Ser Trp Tyr Ala Asp Gly Lys Gly Thr Lys
                165                 170                 175

Trp Arg Asp Ala Phe His Arg Val Gly Val Tyr Trp Arg Asp Pro Trp
                180                 185                 190

His Leu Glu Tyr Tyr Val Asp Gly Lys Leu Val Arg Thr Val Ser Gly
                195                 200                 205

Gln

<210> SEQ ID NO 21
<211> LENGTH: 206
<212> TYPE: PRT
<213> ORGANISM: Pseudomonas sp.

<400> SEQUENCE: 21

Pro Val Pro Ala Asn Ala Gly Asn Gly Lys Val Trp Glu Leu Gln Ala
  1               5                  10                  15

Val Ser Asp Asp Phe Asn Tyr Ser Ser Ser Leu Asp Asn Tyr His Ser
                 20                  25                  30

Glu Phe Thr Arg Arg Trp His Glu Gly Phe Ile Asn Pro Trp Thr Gly
             35                  40                  45

Pro Gly Leu Thr Glu Trp Ile Asp Gly His Ala Tyr Val Thr Asp Gly
         50                  55                  60

Asn Leu Gly Ile Ala Ala Thr Arg Lys Pro Gly Thr Asp Lys Val Arg
 65                  70                  75                  80

Ala Gly Ser Ile Thr Ser His Asp Thr Phe Thr Tyr Pro Leu Tyr Val
                 85                  90                  95

Glu Thr Lys Ala Lys Ile Ser Lys Leu Val Leu Ala Ser Asp Val Trp
            100                 105                 110

Leu Leu Ser Ala Asp Ser Thr Gln Glu Ile Asp Val Leu Glu Ala Tyr
            115                 120                 125

Gly Ser Asp Arg Ala Gly Gln Glu Trp Phe Ala Glu Arg Ile His Leu
        130                 135                 140

Ser His His Val Phe Ile Arg Asp Pro Phe Gln Asp Tyr Gln Pro Thr
145                 150                 155                 160

Asp Ala Gly Ser Trp Tyr Thr Asp Gly Gln Gly Thr Val Trp Ser Asp
                165                 170                 175

Asp Phe His Arg Ile Gly Val His Trp Lys Asp Pro Trp Asn Leu Asp
                180                 185                 190

Tyr Tyr Ile Asp Gly Gln Leu Val Arg Ser Val Ser Gly Pro
                195                 200                 205

<210> SEQ ID NO 22
<211> LENGTH: 219
<212> TYPE: PRT
```

<213> ORGANISM: Zobellia galactanvorans

<400> SEQUENCE: 22

Leu Val Glu Glu Val Asp Trp Lys Asp Ile Pro Val Pro Ala Asp Ala
1               5                   10                  15

Gly Pro Asn Met Lys Trp Glu Phe Gln Glu Ile Ser Asp Asn Phe Glu
            20                  25                  30

Tyr Glu Ala Pro Ala Asp Asn Lys Gly Ser Glu Phe Leu Glu Lys Trp
        35                  40                  45

Asp Asp Phe Tyr His Asn Ala Trp Ala Gly Pro Gly Leu Thr Glu Trp
    50                  55                  60

Lys Arg Asp Arg Ser Tyr Val Ala Asp Gly Glu Leu Lys Met Trp Ala
65                  70                  75                  80

Thr Arg Lys Pro Gly Ser Asp Lys Ile Asn Met Gly Cys Ile Thr Ser
                85                  90                  95

Lys Thr Arg Val Val Tyr Pro Val Tyr Ile Glu Ala Arg Ala Lys Val
            100                 105                 110

Met Asn Ser Thr Leu Ala Ser Asp Val Trp Leu Leu Ser Ala Asp Asp
        115                 120                 125

Thr Gln Glu Ile Asp Ile Leu Glu Ala Tyr Gly Ala Asp Tyr Ser Glu
    130                 135                 140

Ser Ala Gly Lys Asp His Ser Tyr Phe Ser Lys Lys Val His Ile Ser
145                 150                 155                 160

His His Val Phe Ile Arg Asp Pro Phe Gln Asp Tyr Gln Pro Lys Asp
                165                 170                 175

Ala Gly Ser Trp Phe Glu Asp Gly Thr Val Trp Asn Lys Glu Phe His
            180                 185                 190

Arg Phe Gly Val Tyr Trp Arg Asp Pro Trp His Leu Gly Tyr Tyr Ile
        195                 200                 205

Asp Gly Val Leu Val Arg Thr Val Ser Gly Lys
    210                 215

<210> SEQ ID NO 23
<211> LENGTH: 288
<212> TYPE: PRT
<213> ORGANISM: Microscilla sp.

<400> SEQUENCE: 23

Thr Leu Leu Ile Thr Trp Ile Ala Phe Leu Gly Ala Lys Ala Gln Asp
1               5                   10                  15

Trp Ser Gly Ile Pro Val Pro Ala Ser Ala Gln Gly Lys Thr Trp
            20                  25                  30

Gln Leu Gln Ser Ala Ala Ser Asp Asp Phe Asn Tyr Thr Phe Asn Glu
        35                  40                  45

Thr Ser Gln Leu Thr Asn Phe Gly Ser Asn Lys Trp Tyr Asn Phe Tyr
    50                  55                  60

His Asn Gly Trp Asp Gly Pro Gly Thr Thr Tyr Trp Gln Tyr Asn His
65                  70                  75                  80

Val Ser Val Ser Gly Gly Asn Leu Val Leu Arg Ala Ser Arg Asn Pro
                85                  90                  95

Ser Thr Thr Lys Met Gly Val Pro Gly Val Asn Ala Gly Cys Ile Thr
            100                 105                 110

Ser Asn Asn Arg Val Lys Tyr Pro Val Phe Val Glu Ala Ser Val Ser
        115                 120                 125

Val Ala Asn Ile Ala Leu Ala Ser Asp Val Trp Leu Leu Ser Pro Asp

```
Asp Thr Gln Glu Ile Asp Ile Ile Glu Cys Tyr Gly Gly Ala Gly Ser
145                 150                 155                 160

Asn Asn Ala Tyr Phe Ala Gln Phe Ile His Leu Ser His His Ser Phe
            165                 170                 175

Val Arg Asn Pro Phe Gln Asp Tyr Gln Pro Arg Asp Leu Asn Ser Trp
            180                 185                 190

Trp Gly Lys Ser Gly Val Ser Ser Trp Gly Asp Tyr Cys Trp Asn Asn
            195                 200                 205

Gly Asn Arg Lys Tyr Val Arg Val Gly Val Asn Trp Val Gly Pro Lys
    210                 215                 220

His Phe Glu Tyr Tyr Ile Asp Gly Glu Leu Val Arg Val Leu Tyr Asp
225                 230                 235                 240

Lys Ala Phe Ala Thr Lys Val Asn Gly Thr Trp Tyr Tyr Thr Tyr Pro
                245                 250                 255

Thr Met Thr Asn Gly Ser Leu Asp Phe Ser Gly Gly Tyr Gln Ser Val
            260                 265                 270

Val Gln Tyr Ala Thr Gly Ser Ser Tyr Ser Phe Ser Thr Leu Gln Ala
            275                 280                 285

<210> SEQ ID NO 24
<211> LENGTH: 178
<212> TYPE: PRT
<213> ORGANISM: Pseudoalteromonas sp.

<400> SEQUENCE: 24

Ser Gly Lys Pro Ser Ser Phe Thr Ser Lys Trp Lys Asp Ala Tyr Phe
1               5                   10                  15

His Asn Trp Thr Gly Pro Gly Leu Thr Tyr Trp Ser Ser Asp Glu Ser
                20                  25                  30

Trp Val Gly Asp Gly Asn Leu Ile Ile Ser Ala Ser Arg Arg Gln Gly
            35                  40                  45

Thr Asn Gln Val Asn Ala Gly Val Val Thr Ser Lys Thr Lys Val Lys
    50                  55                  60

Tyr Pro Ile Phe Leu Glu Ala Asn Ile Lys Val Ser Asn Leu Glu Leu
65                  70                  75                  80

Ser Ser Asn Phe Trp Leu Leu Ser Glu Asn Asp Gln Arg Glu Ile Asp
                85                  90                  95

Val Leu Glu Val Tyr Gly Gly Ala Arg Gln Asp Trp Phe Ala Lys Asn
            100                 105                 110

Met Ser Thr Asn Phe His Val Phe Arg Asn Asn Asp Asn Ser Ile
            115                 120                 125

Ser Ser Asp Phe Asn Asp Gln Thr His Asn Thr Pro Thr Trp Gly Asn
    130                 135                 140

Tyr Trp Arg Glu Gly Phe His Arg Phe Gly Val Tyr Trp Lys Ser Pro
145                 150                 155                 160

Thr Glu Val Thr Phe Tyr Ile Asn Gly Gln Lys Thr Thr Lys Gly Ala
                165                 170                 175

Trp Ser

<210> SEQ ID NO 25
<211> LENGTH: 222
<212> TYPE: PRT
<213> ORGANISM: Streptomyces coelicolor

<400> SEQUENCE: 25
```

```
Ala Ala Asp Leu Glu Trp Glu Gln Tyr Pro Val Pro Ala Ala Pro Gly
 1               5                  10                  15

Gly Asn Arg Ser Trp Gln Leu Leu Pro Ser His Ser Asp Asp Phe Asn
                20                  25                  30

Tyr Thr Gly Lys Pro Gln Thr Phe Arg Gly Arg Trp Leu Asp Gln His
            35                  40                  45

Lys Asp Gly Trp Ser Gly Pro Ala Asn Ser Leu Tyr Ser Ala Arg His
        50                  55                  60

Ser Trp Val Ala Asp Gly Asn Leu Ile Val Glu Gly Arg Arg Ala Pro
 65                  70                  75                  80

Asp Gly Arg Val Tyr Cys Gly Tyr Val Thr Ser Arg Thr Pro Val Glu
                85                  90                  95

Tyr Pro Leu Tyr Thr Glu Val Leu Met Arg Val Ser Gly Leu Lys Leu
                100                 105                 110

Ser Ser Asn Phe Trp Leu Leu Ser Arg Asp Asp Val Asn Glu Ile Asp
            115                 120                 125

Val Ile Glu Cys Tyr Gly Asn Glu Ser Leu His Gly Lys His Met Asn
    130                 135                 140

Thr Ala Tyr His Ile Phe Gln Arg Asn Pro Phe Thr Glu Leu Ala Arg
145                 150                 155                 160

Ser Gln Lys Gly Tyr Phe Ala Asp Gly Ser Tyr Gly Tyr Asn Gly Glu
                165                 170                 175

Thr Gly Gln Val Phe Gly Asp Gly Ala Gly Gln Pro Leu Leu Arg Asn
                180                 185                 190

Gly Phe His Arg Tyr Gly Val His Trp Ile Ser Ala Thr Glu Phe Asp
                195                 200                 205

Phe Tyr Phe Asn Gly Arg Leu Val Arg Arg Leu Asn Arg Ser
    210                 215                 220

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (20)
<223> OTHER INFORMATION: Any amino acid

<400> SEQUENCE: 26

Glu Leu Ile Val Asp Leu Ile Val Phe Xaa Glu Xaa Xaa Gly Gln Lys
 1               5                  10                  15

Arg Asn Phe Xaa Pro Ser Thr Ala
                20

<210> SEQ ID NO 27
<211> LENGTH: 415
<212> TYPE: PRT
<213> ORGANISM: Vibrio sp.

<400> SEQUENCE: 27
```

```
Ser Glu Ser Ala Leu Arg Gln Ser Met Phe Thr Glu Ile Pro Ser Asp
 1               5                  10                  15

Tyr Val Asn Glu Asn Tyr Gly Pro Val His Ser Gly Pro Val Ser Gln
            20                  25                  30

Gly Gln Ala Val Ser Phe Tyr Ala Asn Asn Leu Ile Thr Arg His Ala
        35                  40                  45

Ser Glu Asp Val Trp Arg Asp Ile Thr Val Lys Arg Met Lys Asp Trp
 50                  55                  60

Gly Phe Asn Thr Leu Gly Asn Trp Thr Asp Pro Ala Leu Tyr Ala Asn
 65              70                  75                  80

Gly Asp Val Pro Tyr Val Ala Asn Gly Trp Ser Thr Ser Gly Ala Asp
                85                  90                  95

Arg Leu Pro Val Lys Gln Ile Gly Ser Gly Tyr Trp Gly Pro Leu Pro
            100                 105                 110

Asp Pro Trp Asp Ala Asn Phe Ala Thr Asn Ala Ala Thr Met Ala Ala
        115                 120                 125

Glu Ile Lys Ala Gln Val Glu Gly Asn Glu Glu Tyr Leu Val Gly Ile
    130                 135                 140

Phe Val Asp Asn Glu Met Ser Trp Gly Asn Val Thr Asp Val Glu Gly
145                 150                 155                 160

Ser Arg Tyr Ala Gln Thr Leu Ala Val Phe Asn Thr Asp Gly Thr Asp
                165                 170                 175

Ala Thr Thr Ser Pro Ala Lys Asn Ser Phe Ile Trp Phe Leu Glu Asn
            180                 185                 190

Gln Arg Tyr Thr Gly Gly Ile Ala Asp Leu Asn Ala Ala Trp Gly Thr
        195                 200                 205

Asp Tyr Ala Ser Trp Asp Ala Thr Ser Pro Ala Gln Glu Leu Ala Tyr
210                 215                 220

Val Ala Gly Met Glu Ala Asp Met Gln Phe Leu Ala Trp Gln Phe Ala
225                 230                 235                 240

Phe Gln Tyr Phe Asn Thr Val Asn Thr Ala Leu Lys Ala Glu Leu Pro
                245                 250                 255

Asn His Leu Tyr Leu Gly Ser Arg Phe Ala Asp Trp Gly Arg Thr Pro
            260                 265                 270

Asp Val Val Ser Ala Ala Ala Val Val Asp Val Met Ser Tyr Asn
        275                 280                 285

Ile Tyr Lys Asp Ser Ile Ala Ala Asp Trp Asp Ala Asp Ala Leu
    290                 295                 300

Ser Gln Ile Glu Ala Ile Asp Lys Pro Val Ile Ile Gly Glu Phe His
305                 310                 315                 320

Phe Gly Ala Leu Asp Ser Gly Ser Phe Ala Glu Gly Val Val Asn Ala
                325                 330                 335

Thr Ser Gln Gln Asp Arg Ala Asp Lys Met Val Ser Phe Tyr Glu Ser
            340                 345                 350

Val Asn Ala His Lys Asn Phe Val Gly Ala His Trp Phe Gln Tyr Ile
        355                 360                 365

Asp Ser Pro Leu Thr Gly Arg Ala Trp Asp Gly Glu Asn Tyr Asn Val
370                 375                 380

Gly Phe Val Ser Asn Thr Asp Thr Pro Tyr Thr Leu Met Thr Asp Ala
385                 390                 395                 400

Ala Arg Glu Phe Asn Cys Gly Met Tyr Gly Thr Asp Cys Ser Ser
                405                 410                 415
```

<210> SEQ ID NO 28
<211> LENGTH: 417
<212> TYPE: PRT
<213> ORGANISM: Agarivorans sp.

<400> SEQUENCE: 28

```
Ser Ala Leu Arg Gln Ser Met Phe Thr Glu Ile Pro Ser Asp Tyr Val
 1               5                  10                  15

Asn Glu Asn Tyr Gly Pro Val His Ser Gly Pro Val Ser Gln Gly Gln
             20                  25                  30

Ala Val Ser Phe Tyr Ala Asn Asn Leu Ile Thr Arg His Ala Ser Glu
         35                  40                  45

Asp Val Trp Arg Asp Ile Thr Val Lys Arg Met Lys Asp Trp Gly Phe
     50                  55                  60

Asn Thr Leu Gly Asn Trp Thr Asp Pro Ala Leu Tyr Ala Asn Gly Asp
 65                  70                  75                  80

Val Pro Tyr Val Ala Asn Gly Trp Ser Thr Ser Gly Ala Asp Arg Leu
                 85                  90                  95

Pro Val Lys Gln Ile Gly Ser Gly Tyr Trp Gly Pro Leu Pro Asp Pro
            100                 105                 110

Trp Asp Ala Asn Phe Ala Thr Asn Ala Ala Thr Met Ala Ala Glu Ile
        115                 120                 125

Lys Ala Gln Val Glu Gly Asn Glu Glu Tyr Leu Val Gly Ile Phe Val
    130                 135                 140

Asp Asn Glu Met Ser Trp Gly Asn Val Thr Asp Val Glu Gly Ser Arg
145                 150                 155                 160

Tyr Ala Gln Thr Leu Ala Val Phe Asn Thr Asp Gly Thr Asp Ala Thr
                165                 170                 175

Thr Ser Pro Ala Lys Asn Ser Phe Ile Trp Phe Leu Glu Asn Gln Arg
            180                 185                 190

Tyr Thr Gly Gly Ile Ala Asp Leu Asn Ala Ala Trp Gly Thr Asp Tyr
        195                 200                 205

Ala Ser Trp Asp Ala Met Arg Pro Ala Gln Glu Leu Ala Tyr Val Ala
    210                 215                 220

Gly Met Glu Ala Asp Met Gln Phe Leu Ala Trp Gln Phe Ala Phe Gln
225                 230                 235                 240

Tyr Phe Asn Thr Val Asn Thr Ala Leu Lys Ala Glu Leu Pro Asn His
                245                 250                 255

Leu Tyr Leu Gly Ser Arg Phe Ala Asp Trp Gly Arg Thr Pro Asp Val
            260                 265                 270

Val Ser Ala Ala Ala Val Val Asp Val Met Ser Tyr Asn Ile Tyr
        275                 280                 285

Lys Asp Ser Ile Ala Ala Asp Trp Asp Ala Asp Ala Leu Ser Gln
    290                 295                 300

Ile Glu Ala Ile Asp Lys Pro Val Ile Gly Glu Phe His Phe Gly
305                 310                 315                 320

Ala Leu Asp Ser Gly Ser Phe Ala Glu Gly Val Val Asn Ala Thr Ser
                325                 330                 335

Gln Gln Asp Arg Ala Asp Lys Met Val Ser Phe Tyr Glu Ser Val Asn
            340                 345                 350

Ala His Lys Asn Phe Val Gly Ala His Trp Phe Gln Tyr Ile Asp Ser
        355                 360                 365

Pro Leu Thr Gly Arg Ala Trp Asp Gly Glu Asn Tyr Asn Val Gly Phe
    370                 375                 380
```

```
Val Ser Asn Thr Asp Thr Pro Tyr Thr Leu Met Thr Asp Ala Ala Arg
385                 390                 395                 400

Glu Phe Asn Cys Gly Met Tyr Gly Thr Asp Cys Ser Ser Leu Ser Asn
                405                 410                 415

Ala

<210> SEQ ID NO 29
<211> LENGTH: 420
<212> TYPE: PRT
<213> ORGANISM: Unknown
<220> FEATURE:
<223> OTHER INFORMATION: Description of Unknown Organism: Uncultured
      bacterium

<400> SEQUENCE: 29

Lys Ser Ala Trp Ser Ser Arg His Ile Ser Ser Gln Leu Arg Ala Asp
  1               5                  10                  15

Met Phe Thr Trp Leu Pro Ser Tyr Asn Glu Ala Gly Ala Asn Tyr
                 20                  25                  30

Gly Tyr Arg Arg Ser Val His Ser Gly Ser Leu Lys His Gly Glu Thr
                 35                  40                  45

Phe Ser Phe Tyr Arg Ala Asn Leu Ala Arg Lys Tyr Ala Thr Gln Asp
     50                  55                  60

Glu Glu Thr Leu Met Gln Tyr Trp Arg Asp Ala Thr Ile Lys Arg Met
 65                  70                  75                  80

His Asn Trp Gly Phe Thr Ser Phe Gly Asn Trp Val Asp Ala Ser Phe
                 85                  90                  95

Tyr Gln Met Asn Arg Leu Pro Tyr Phe Ala Asn Gly Trp Ile Ile Gly
                100                 105                 110

Asp Phe Lys Thr Val Asn Ser Gly Asn Asp Tyr Trp Gly Ala Met Pro
                115                 120                 125

Asp Pro Phe Asp Pro Val Phe Thr Gln Arg Thr Asp Lys Val Ile Ala
                130                 135                 140

Gln Ile Ala Asn Glu Val Lys Asn Asn Pro Trp Cys Val Gly Val Phe
145                 150                 155                 160

Ile Asp Asn Glu Lys Ser Trp Gly Ser Met Gly Thr Pro Ser Leu Gln
                165                 170                 175

Tyr Gly Ile Val Ile Asn Gly Leu Lys Lys Lys Ala Asn Asp Ser Pro
                180                 185                 190

Leu Lys Gln Glu Phe Ile Arg His Leu Lys Asn Lys Tyr Gln Asn Ile
                195                 200                 205

Glu Asn Leu Asn Thr Ala Trp Asp Leu Lys Asn Thr Ser Trp Ala Gln
                210                 215                 220

Leu Ser Gln Pro Val Glu Leu Val Leu Phe Asn Glu Lys Met Leu Gly
225                 230                 235                 240

Asp Phe Ser Glu Leu Leu Tyr Leu Tyr Ala Asp Ala Tyr Phe Ser Arg
                245                 250                 255

Val Asn Gln Ala Phe Arg Lys His Met Pro Asn His Leu Tyr Met Gly
                260                 265                 270

Pro Arg Phe Ala His Trp Ala Met Thr Pro Glu Val Leu Lys Ala Ala
                275                 280                 285

Ala Lys Tyr Thr Asp Val Met Ser Tyr Asn Tyr Tyr Arg Glu Gly Ile
                290                 295                 300

Asp Gln Pro Tyr Trp Asp Phe Leu Ala Glu Leu Asp Lys Pro Ser Ile
305                 310                 315                 320
```

```
Ile Gly Glu Phe His Asn Gly Ala Ile Asp Ser Gly Leu Leu Asn Pro
                325                 330                 335

Gly Leu Ile His Ala Glu Ser Gln Phe Asp Arg Gly Glu Lys Tyr Lys
            340                 345                 350

Ser Tyr Leu Asn Ser Val Ile Asp Asn Pro Tyr Phe Val Gly Ala His
        355                 360                 365

Trp Phe Gln Tyr Ile Asp Ser Pro Leu Thr Gly Arg Ala Tyr Asp Gly
370                 375                 380

Glu Asn Tyr Asn Val Gly Phe Val Ser Val Ala Asp Ile Pro Tyr Pro
385                 390                 395                 400

Pro Leu Val Lys Ala Ala Gln Glu Val Asn Arg Asn Leu Tyr Gln Lys
            405                 410                 415

Arg Phe Gly Lys
            420

<210> SEQ ID NO 30
<211> LENGTH: 420
<212> TYPE: PRT
<213> ORGANISM: Saccharophagus degradans

<400> SEQUENCE: 30

Asp Ala Ala Leu Pro Thr Arg His Ile Ser Ser Pro Leu Arg Ala Glu
1               5                   10                  15

Met Phe Thr Trp Leu Pro Gln Tyr Asp Glu Pro Leu Gly Leu Asn Phe
            20                  25                  30

Gly Tyr Arg Arg Glu Val His Thr Gly Ala Ile Glu Arg Gly Glu Thr
        35                  40                  45

Phe Ser Phe Tyr Arg Ala Asn Leu Gln Arg Lys Tyr Gly Ile Ser Asp
    50                  55                  60

Glu Ala Ala Leu Met Glu Lys Trp Arg Glu Thr Thr Val Asn Arg Met
65                  70                  75                  80

Leu Ser Trp Gly Phe Thr Ser Phe Gly Asn Trp Ile Asp Pro Ala Tyr
                85                  90                  95

Tyr Gln Met Asp Arg Ile Pro Tyr Phe Ala Asn Gly Trp Ile Ile Gly
            100                 105                 110

Asn Phe Lys Thr Val Ser Ser Gly Asn Asp Tyr Trp Ser Pro Leu Pro
        115                 120                 125

Asp Pro Phe Asp Pro Leu Phe Lys Glu Arg Ala Tyr Ile Ile Ala Glu
    130                 135                 140

Gln Ile Gly Arg Glu Val Lys Asn Asn Pro Trp Cys Val Gly Val Phe
145                 150                 155                 160

Ile Asp Asn Glu Lys Ser Trp Gly Gln Glu Gly Ala Val Gln Thr Gln
                165                 170                 175

Tyr Gly Leu Val Ile Asn Thr Leu Ser Arg Ala Ala Glu Asp Ser Pro
            180                 185                 190

Thr Lys Ala Gln Phe Val Met Leu Met Gln Lys Tyr Gly Ala Ile
        195                 200                 205

Thr Glu Leu Asn Arg Ala Trp Asn Val Glu Leu Asn Ser Trp Gln Glu
    210                 215                 220

Phe Ala Asn Gly Val Val Leu Thr Gln Phe Ser Asp Ala Val Val Ala
225                 230                 235                 240

Asp Leu Ser Val Met Leu Glu His Tyr Ala Gly Gln Tyr Phe Lys Ile
                245                 250                 255

Val Arg Glu Ala Val Lys His Tyr Leu Pro Asn His Met Tyr Leu Gly
```

```
                260                 265                 270
Ala Arg Phe Ala Asp Trp Gly Met Thr Pro Glu Ile Arg Arg Ser Ala
            275                 280                 285

Ala Lys Tyr Ala Asp Val Val Ser Tyr Asn Tyr Tyr Lys Glu Gly Val
        290                 295                 300

Ser Asn Lys Phe Trp His Phe Leu Glu Glu Leu Asp Lys Pro Ser Ile
305                 310                 315                 320

Ile Gly Glu Phe His Asn Gly Ala Leu Asp Ser Gly Leu Leu Asn Pro
                325                 330                 335

Gly Val Val His Ala Ser Ser Gln Ala Asp Arg Gly Lys Lys Tyr Ala
            340                 345                 350

Glu Tyr Met Asn Ser Val Ile Asp Asn Pro Tyr Phe Val Gly Ala His
        355                 360                 365

Trp Phe Gln Tyr Ile Asp Ser Pro Leu Thr Gly Arg Ala Tyr Asp Gly
    370                 375                 380

Glu Asn Tyr Asn Val Gly Phe Val Ser Ile Thr Asp Ile Pro Tyr Thr
385                 390                 395                 400

Ser Leu Val Asp Ala Ala Arg Glu Val Asn Lys Ala Leu Tyr Ser Arg
                405                 410                 415

Arg Phe Gly Glu
            420

<210> SEQ ID NO 31
<211> LENGTH: 423
<212> TYPE: PRT
<213> ORGANISM: Saccharophagus degradans

<400> SEQUENCE: 31

Glu Lys Ser Phe Ala Thr Arg His Leu Ala Ser Pro Thr Arg Ala Ala
  1               5                  10                  15

Met Phe Asn Trp Leu Pro Asp Tyr Asp His Pro Leu Ala Asn His Tyr
             20                  25                  30

Asn Tyr Arg Arg Ser Ala His Ser Gly Pro Leu Lys Arg Gly Glu Ala
         35                  40                  45

Tyr Ser Phe Tyr Ser Ala Asn Leu Glu Arg Lys Tyr Gly Glu Thr Tyr
     50                  55                  60

Pro Gly Ser Tyr Leu Asp Lys Trp Arg Glu Val Thr Val Asp Arg Met
 65                  70                  75                  80

Leu Asn Trp Gly Phe Thr Ser Leu Gly Asn Trp Thr Asp Pro Ala Tyr
                 85                  90                  95

Tyr Asp Asn Asn Arg Ile Pro Phe Phe Ala Asn Gly Trp Val Ile Gly
            100                 105                 110

Asp Phe Lys Thr Val Ser Ser Gly Ala Asp Phe Trp Gly Ala Met Pro
        115                 120                 125

Asp Val Phe Asp Pro Glu Phe Lys Val Arg Ala Met Glu Thr Ala Arg
    130                 135                 140

Val Val Ser Glu Glu Ile Lys Asn Ser Pro Trp Cys Val Gly Val Phe
145                 150                 155                 160

Ile Asp Asn Glu Lys Ser Phe Gly Arg Pro Asp Ser Asp Lys Ala Gln
                165                 170                 175

Tyr Gly Ile Pro Ile His Thr Leu Gly Arg Pro Ser Glu Gly Val Pro
            180                 185                 190

Thr Arg Gln Ala Phe Ser Lys Leu Leu Lys Ala Lys Tyr Lys Thr Ile
        195                 200                 205
```

```
Ala Ala Leu Asn Asn Ala Trp Gly Leu Lys Leu Ser Ser Trp Ala Glu
    210                 215                 220

Phe Asp Leu Gly Val Asp Val Lys Ala Leu Pro Val Thr Asp Thr Leu
225                 230                 235                 240

Arg Ala Asp Tyr Ser Met Leu Leu Ser Ala Tyr Ala Asp Gln Tyr Phe
                245                 250                 255

Lys Val Val His Gly Ala Val Glu His Tyr Met Pro Asn His Leu Tyr
            260                 265                 270

Leu Gly Ala Arg Phe Pro Asp Trp Gly Met Pro Met Glu Val Val Lys
        275                 280                 285

Ala Ala Ala Lys Tyr Ala Asp Val Val Ser Tyr Asn Ser Tyr Lys Glu
    290                 295                 300

Gly Leu Pro Lys Gln Lys Trp Ala Phe Leu Ala Glu Leu Asp Lys Pro
305                 310                 315                 320

Ser Ile Ile Gly Glu Phe His Ile Gly Ala Met Asp His Gly Ser Tyr
                325                 330                 335

His Pro Gly Leu Ile His Ala Ala Ser Gln Ala Asp Arg Gly Glu Met
            340                 345                 350

Tyr Lys Asp Tyr Met Gln Ser Val Ile Asp Asn Pro Tyr Phe Val Gly
        355                 360                 365

Ala His Trp Phe Gln Tyr Met Asp Ser Pro Leu Thr Gly Arg Ala Tyr
    370                 375                 380

Asp Gly Glu Asn Tyr Asn Val Gly Phe Val Asp Val Thr Asp Thr Pro
385                 390                 395                 400

Tyr Gln Glu Met Val Asp Ala Ala Lys Glu Val Asn Ala Lys Ile Tyr
                405                 410                 415

Thr Glu Arg Leu Gly Ser Lys
            420

<210> SEQ ID NO 32
<211> LENGTH: 423
<212> TYPE: PRT
<213> ORGANISM: Streptomyces coelicolor

<400> SEQUENCE: 32

Lys Ser Ala Leu Pro Thr Arg Thr Lys Met Ser Glu Thr Arg Ala Asp
1               5                   10                  15

Leu Phe Ser Lys Leu Pro Lys Tyr Arg Thr Arg Ala Gly Glu Gly Phe
            20                  25                  30

Gly Tyr Ala Pro Asp Thr Leu Ala Gly Pro Val Ala Gln Gly Glu Thr
        35                  40                  45

Tyr Ser Phe Tyr Lys Ala Asn Val Ala Arg Lys Tyr Pro Gly Ser Asn
    50                  55                  60

Tyr Met Glu Arg Trp Arg Asp Asn Thr Val Asp Arg Met Leu Ser Trp
65                  70                  75                  80

Gly Phe Thr Ser Phe Gly Asn Trp Thr Asp Pro Glu Met Tyr Asp Asn
                85                  90                  95

Asp Arg Ile Pro Tyr Phe Ala His Gly Trp Ile Lys Gly Asp Phe Lys
            100                 105                 110

Thr Val Ser Thr Gly Gln Asp Tyr Trp Gly Pro Met Pro Asp Pro Phe
        115                 120                 125

Asp Pro Ala Phe Ser Asp Ala Ala Arg Thr Ala Arg Ala Val Ala
    130                 135                 140

Asp Glu Val Ala Asp Ser Pro Leu Ala Ile Gly Val Phe Met Asp Asn
145                 150                 155                 160
```

```
Glu Leu Ser Trp Gly Asn Ala Gly Ser Phe Ser Thr Arg Tyr Gly Val
            165                 170                 175

Val Ile Asp Thr Met Ser Arg Asp Ala Ala Glu Ser Pro Thr Lys Ser
        180                 185                 190

Ala Phe Ser Asp Glu Leu Glu Glu Lys Tyr Gly Thr Ile Asp Ala Leu
            195                 200                 205

Asn Ala Ala Trp Gln Thr Thr Val Pro Ser Trp Glu Ala Leu Arg Ser
210                 215                 220

Gly Ser Ala Asp Leu Gly Ser Asp Glu Thr Ala Lys Glu Ser Asp Tyr
225                 230                 235                 240

Ser Ala Leu Met Thr Leu Tyr Ala Thr Gln Tyr Phe Lys Thr Val Asp
                245                 250                 255

Ala Glu Leu Asp Lys Val Met Pro Asp His Leu Tyr Ala Gly Ser Arg
            260                 265                 270

Phe Ala Ser Trp Gly Arg Thr Pro Glu Val Val Glu Ala Ala Ser Lys
        275                 280                 285

Tyr Val Asp Ile Met Ser Tyr Asn Glu Tyr Arg Glu Gly Leu His Pro
    290                 295                 300

Ser Glu Trp Ala Phe Leu Glu Glu Leu Asp Lys Pro Ser Leu Ile Gly
305                 310                 315                 320

Glu Phe His Met Gly Thr Thr Thr Gly Gln Pro His Pro Gly Leu
                325                 330                 335

Val Ser Ala Gly Thr Gln Ala Glu Arg Ala Arg Met Tyr Ala Glu Tyr
            340                 345                 350

Met Glu Gln Leu Ile Asp Asn Pro Tyr Met Val Gly Gly His Trp Phe
        355                 360                 365

Gln Tyr Ala Asp Ser Pro Val Thr Gly Arg Ala Leu Asp Gly Glu Asn
    370                 375                 380

Tyr Asn Ile Gly Phe Val Ser Val Thr Asp Arg Pro Tyr Pro Glu Ile
385                 390                 395                 400

Val Ala Ala Arg Asp Val Asn Gln Arg Leu Tyr Asp Arg Tyr
                405                 410                 415

Gly Asn Leu Ala Thr Ala Glu
            420

<210> SEQ ID NO 33
<211> LENGTH: 422
<212> TYPE: PRT
<213> ORGANISM: Vibrio sp.

<400> SEQUENCE: 33

Lys Asp Lys Arg Ser Gly Lys Glu Val Ala Ser Glu Val Arg Arg Ser
1               5                   10                  15

Met Phe Thr Trp Leu Pro Glu Asp Asp Val Leu Ala Glu Asn Tyr
            20                  25                  30

Asp Tyr Ala Asn Trp Val His Ser Gly Ala Leu Lys Lys Gly Glu Val
        35                  40                  45

Phe Ser Phe Tyr Gly Ala Asn Leu Gln Arg Lys Tyr Gly Gly Thr Phe
    50                  55                  60

Ser Glu Ala Glu Lys Val Trp Lys Asp Ile Thr Ile Asp Arg Met Val
65                  70                  75                  80

Asp Trp Gly Phe Thr Thr Leu Gly Asn Trp Ala Asp Pro Met Phe Tyr
                85                  90                  95

Asp Asn Lys Lys Val Ala Tyr Val Ala Asn Gly Trp Ile Phe Gly Asp
```

```
            100                 105                 110
His Ala Arg Ile Ser Thr Gly Asn Asp Tyr Trp Gly Pro Ile His Asp
            115                 120                 125

Pro Phe Asp Pro Glu Phe Val Asn Ser Val Lys Ala Met Thr Lys Lys
            130                 135                 140

Leu Met Thr Glu Val Asp Lys Asn Asp Pro Trp Met Met Gly Val Phe
145                 150                 155                 160

Val Asp Asn Glu Ile Ser Trp Gly Asn Thr Lys Asn Asp Ala Asn His
            165                 170                 175

Tyr Gly Leu Val Val Asn Ala Leu Ser Tyr Asp Met Lys Lys Ser Pro
            180                 185                 190

Ala Lys Ala Ala Phe Thr Glu His Leu Lys Glu Lys Tyr Trp Ala Ile
            195                 200                 205

Glu Asp Leu Asn Thr Ser Trp Gly Val Lys Val Ala Ser Trp Ala Glu
            210                 215                 220

Phe Glu Lys Ser Phe Asp His Arg Ser Arg Leu Ser Lys Asn Met Lys
225                 230                 235                 240

Lys Asp Tyr Ala Glu Met Leu Glu Met Leu Ser Ala Lys Tyr Phe Ser
            245                 250                 255

Thr Val Arg Ala Glu Leu Lys Lys Val Leu Pro Asn His Leu Tyr Leu
            260                 265                 270

Gly Ala Pro Phe Ala Asp Trp Gly Val Thr Pro Glu Ile Ala Lys Gly
            275                 280                 285

Ala Ala Pro Tyr Val Asp Val Met Ser Tyr Asn Leu Tyr Ala Glu Asp
            290                 295                 300

Leu Asn Ser Lys Gly Asp Trp Ser Lys Leu Ala Glu Leu Asp Lys Pro
305                 310                 315                 320

Ser Ile Ile Gly Glu Phe His Phe Gly Ser Thr Asp Ser Gly Leu Phe
            325                 330                 335

His Gly Gly Ile Val Ser Ala Ala Ser Gln Gln Asp Arg Ala Lys Lys
            340                 345                 350

Tyr Thr Asn Tyr Met Asn Ser Ile Ala Asp Asn Pro Tyr Phe Val Gly
            355                 360                 365

Ala His Trp Phe Gln Tyr Ile Asp Ser Pro Thr Thr Gly Arg Ala Trp
            370                 375                 380

Asp Gly Glu Asn Tyr Asn Val Gly Phe Val Ser Ile Thr Asp Thr Pro
385                 390                 395                 400

Tyr Val Pro Leu Val Glu Ala Ala Lys Lys Phe Asn Gln Asp Val Tyr
            405                 410                 415

Met Leu Arg Tyr Lys Lys
            420

<210> SEQ ID NO 34
<211> LENGTH: 408
<212> TYPE: PRT
<213> ORGANISM: Azotobacter vinelandii

<400> SEQUENCE: 34

Tyr Gly Gln Ser Cys Lys Pro Pro Val Glu Gln Ala Ala Glu Pro Glu
1               5                   10                  15

Arg Val Leu Pro Ala Ala Pro Met Glu Glu Glu Pro Asp Asn Val Gln
            20                  25                  30

Val Ala Pro Glu Gly Gly Thr Pro Ala Pro Gly Gln Pro Ala Pro Ala
            35                  40                  45
```

Lys Gln Pro Thr Ala Ala Pro Pro Cys Val Val Gln Phe Phe Asp Ala
    50                  55                  60

Leu Arg Trp Arg Gly His Thr Leu Asp Arg Leu Gln Ala Trp Gly Phe
 65                  70                  75                  80

Asn Thr Leu Gly Asn Trp Ser Asp Leu Ser Leu Gly Ala Met His Arg
                 85                  90                  95

Ile Pro Tyr Thr Ile Pro Leu Leu Ile Arg Gly Asp Tyr Ala Thr Ile
            100                 105                 110

Ser Thr Gly His Asp Trp Trp Gly Gly Met Pro Asp Pro Phe Asp Pro
            115                 120                 125

Arg Phe Ala Met Ala Val Glu Arg Ala Ile Ala Ile Ala Thr Arg Asp
130                 135                 140

His Arg Asn Asp Pro Trp Val Ile Gly Tyr Phe Ala Asp Asn Glu Leu
145                 150                 155                 160

Ser Trp Ala Ala Pro Gly Thr Asp Pro Lys Ala Arg Tyr Ala Leu Ala
                165                 170                 175

Tyr Gly Thr Leu Arg Gln Thr Thr Asp Met Pro Ala Lys Arg Ala Phe
            180                 185                 190

Leu Lys Leu Leu Arg Asp Arg Tyr Arg Asn Gln Gln Gly Leu Ser Ala
            195                 200                 205

Ala Trp Gly Ile Glu Leu Pro Ala Trp Glu Leu Met Glu Asp Pro Gly
210                 215                 220

Phe Glu Ala Pro Leu Pro Ser Pro Glu His Pro Ala Ile Glu Glu Asp
225                 230                 235                 240

Leu Gln Arg Phe Gln Gln Leu Phe Ala Asp Thr Tyr Phe Lys Thr Ile
                245                 250                 255

Ala Glu Ser Leu Lys Trp His Ala Pro Asp His Leu Leu Leu Gly Gly
            260                 265                 270

Arg Phe Ala Ile Ser Thr Pro Glu Ala Val Glu Ala Cys Ala Lys Tyr
            275                 280                 285

Cys Asp Val Leu Ser Phe Asn Phe Tyr Thr Arg Glu Pro Gln His Gly
290                 295                 300

Tyr Asp Phe Glu Ala Leu Arg Lys Leu Asp Lys Pro Met Leu Val Ser
305                 310                 315                 320

Glu Phe His Phe Gly Ser Arg Asp Arg Gly Pro Phe Trp Gly Gly Val
                325                 330                 335

Ala Glu Val Tyr Lys Glu Glu Arg Gly Pro Ala Tyr Ala His Phe
            340                 345                 350

Leu Glu Arg Ala Leu Ala Glu Pro Phe Ile Val Gly Met His Trp Phe
            355                 360                 365

Gln Tyr Leu Asp Gln Pro Ala Thr Gly Arg Leu Leu Asp Gly Glu Asn
370                 375                 380

Gly His Ile Gly Leu Val Gly Val Thr Asp Arg Pro Phe Ala Gly Phe
385                 390                 395                 400

Val Glu Ala Leu Arg Lys Ala Asn
                405

<210> SEQ ID NO 35
<211> LENGTH: 641
<212> TYPE: PRT
<213> ORGANISM: Saccharophagus degradans

<400> SEQUENCE: 35

Ile Asp Val Asn Pro Tyr Ile Arg His Ser Val Gly Gly Val Asp Ser
  1               5                  10                  15

```
Phe Asp Arg Arg Lys Phe Ile Thr Ile His Ala Ser Asn Thr Glu Asn
                20                  25                  30

Asp Trp Phe Gly Gly Asn Asp Ala Ser Leu Gly Phe Ala Asn Glu Ser
            35                  40                  45

Asp Asp Leu Ile Thr Glu Phe Leu Glu Gly Tyr Asp Val Tyr Phe Gly
 50                  55                  60

Arg Asp Thr Gly Gly Ile Ser Trp His Leu Ser Gln Thr Leu Glu Asp
 65                  70                  75                  80

Pro Ala Lys Pro Gly Phe Ala Asp Glu Ala Asn Met Thr Ser Arg Gly
                85                  90                  95

Asn Asp Thr Lys Gly Trp Tyr Thr Val Asn Pro Ser Glu Ile Ala Ile
                100                 105                 110

Lys Gln Arg Gln His Glu His Arg Asn Thr Asp Met Ile Ile Gly Ser
                115                 120                 125

Gln Gln His Pro Phe Trp Pro Asp Gly Lys Leu Thr Gly Gln Gly Trp
    130                 135                 140

Ala Leu Ser Gln Thr Glu Thr Glu Ala Glu Pro Phe Gly Thr Ala Thr
145                 150                 155                 160

Gly His Tyr Met Ala Asn Phe Leu Ala Lys Phe Tyr Lys Gln Ser Glu
                165                 170                 175

Ser Asp Pro Asn Gly Gln Pro Lys Pro Val Tyr Val Glu Val Met Asn
                180                 185                 190

Glu Pro Leu Tyr Asp Leu Val Asp Ala Ala Thr Asn Pro Thr Thr Pro
            195                 200                 205

Glu Lys Val Phe Leu Phe His Asn Thr Val Ala Asp Glu Ile Arg Lys
            210                 215                 220

Leu Asn Asp Asp Val Leu Ile Gly Gly Tyr Thr Val Ala Phe Pro Asp
225                 230                 235                 240

Phe Asp Ser Asn Asn Phe Glu Arg Trp Glu Asn Arg Asp Lys Ala Phe
                245                 250                 255

Ile Asp Ile Ala Gly Glu Lys Met Asp Phe Ile Ser Ile His Leu Tyr
                260                 265                 270

Asp Phe Pro Asn Phe Gln Asn Thr Gln Arg Tyr Arg Lys Gly Ser Asn
                275                 280                 285

Val Glu Ala Thr Phe Asp Met Leu Asp His Tyr Thr Thr Leu Thr Leu
    290                 295                 300

Gly Ala Pro Leu Pro Leu Ile Val Ser Glu Tyr Gly Ala Pro Asp His
305                 310                 315                 320

Ala Leu Phe Lys Ala Pro Trp Thr Pro Tyr Arg Asp Gly Leu Lys Leu
                325                 330                 335

Lys Ala Leu Asn Ser Leu Leu Met Ser Met Leu Glu Arg Pro Asp Thr
                340                 345                 350

Leu Leu Lys Thr Ile Pro Phe Ile Pro Val Lys Ala Glu Trp Gly Arg
                355                 360                 365

Asp Gly Val Pro Tyr Asn Asp Arg Leu Met Arg Gln Lys Phe Glu Ala
                370                 375                 380

Glu Gly Glu Thr Gly Asn Glu Trp Val Tyr Thr Asp Leu Val Lys Phe
385                 390                 395                 400

Tyr Gln Leu Trp Ala Asp Val Asn Gly Thr Arg Val Asp Ser Tyr Ala
                405                 410                 415

Ala Asp Met Asp Ile Leu Val Asp Ser Tyr Val Asp Gly Ser Thr Leu
                420                 425                 430
```

```
Tyr Leu Ile Leu Asn Asn Leu Glu Phe Asn Asp Glu Thr Leu Thr Leu
            435                 440                 445

Thr Asp Leu Gly Leu Asn Asn Ser Phe Val Ser Gly Thr Met Arg
450                 455                 460

His Leu His Thr Val Asp Gly Asn Pro Val Leu Ser Glu Ser Ala Leu
465                 470                 475                 480

Ala Asn Ile Pro Thr Asn Leu Thr Ile Gly Gly Ala Thr Ile Val
                485                 490                 495

Leu Ala Leu Asn Phe Glu Asn Asp Ile Ala Ile Ser Glu Thr Ser Glu
                500                 505                 510

Glu Thr Lys Tyr Tyr Ala Thr Thr Tyr Lys Gln Ala Ile Thr Ala Asn
            515                 520                 525

Thr Asp Ile Ser Phe Ala Ile Asn Asn Val Ala Leu Gly Asp Gln Gly
            530                 535                 540

Glu Ala Ile Leu Arg Leu Gly Ile Gly Arg Asp His Gly Leu Ser Leu
545                 550                 555                 560

Gln Pro Ser Val Ser Val Asn Gly Val Asp Val Glu Val Pro Ser Asp
                565                 570                 575

Tyr Arg Gly Tyr Asp Gln Phe His Asn Gly Thr Gly Arg Pro Asn Phe
                580                 585                 590

Tyr Gly Val Ile Glu Ile Pro Val Pro Tyr Ser Ala Leu Gln Thr Ser
            595                 600                 605

Asn Thr Val Val Val Asn Phe Pro Asp Ser Thr Gly Phe Val Thr Thr
            610                 615                 620

Ala Ala Leu Gln Val Phe Asn Thr Ser Thr Ser Ile Thr Arg Pro Met
625                 630                 635                 640

Gln

<210> SEQ ID NO 36
<211> LENGTH: 618
<212> TYPE: PRT
<213> ORGANISM: Microscilla sp.

<400> SEQUENCE: 36

Val Asp Val Gln Phe Asn Val Lys His Val Gly Asn Val Ser Met
 1               5                  10                  15

Phe Asp Arg Asn Lys Phe Val Thr Ile His Ala Asp Val Pro Glu Arg
                20                  25                  30

Glu Trp Glu Gly Asp Asn Phe Thr Thr Asp Leu Arg Lys Asp Phe Leu
            35                  40                  45

Asp Arg Tyr Asp Val Tyr Leu Gly Arg Asn Thr Gly Ile Thr Trp
 50                  55                  60

Tyr Leu Asn Asn Gln Val Thr Glu Asp Pro Glu Arg Pro Gly Tyr Ala
 65                  70                  75                  80

Asn Pro Ala Asp Val Glu Ala Ile Gly Arg Asn Leu Lys Asn Gln Tyr
                85                  90                  95

Ala Val Asn Ser Val Trp Gln Ala Tyr Glu His Arg Asn Asp Gln Ile
                100                 105                 110

Ile Ala Ala Gln Leu His Pro Phe Trp Pro Asp Gly Gln Leu Thr Asn
            115                 120                 125

Gln Gly Trp Ala Phe Ser Gln Thr Asp Thr Glu Val Glu Pro Phe Gly
130                 135                 140

Thr Ala Thr Gly Glu Tyr Met Gly Arg Phe Ile Arg Asp Ala Phe Gly
145                 150                 155                 160
```

-continued

Glu Gly Gly Thr Ala Gly Gln Pro Arg Pro Asp Tyr Val Glu Ile Ile
              165                 170                 175

Asn Glu Pro Val Trp His Leu Val Asp Tyr Gly Asp Glu Ser Ala Glu
              180                 185                 190

Lys Val Phe Arg Phe His Asn Gly Val Ala Lys Ala Ile Arg Gln Thr
              195                 200                 205

Val Pro Asp Ile Gln Ile Gly Gly Tyr Cys Thr Ala Phe Pro Asn His
210                 215                 220

Glu Thr Asn Gly Phe Gln Glu Trp Asn Asn Arg Trp Lys Leu Phe Met
225                 230                 235                 240

Asp Ile Ser Gly Glu Tyr Met Asp Tyr Trp Ser Ile His Leu Tyr Asp
              245                 250                 255

Phe Pro Ser Ile Asn Asn Gly Lys Gln Leu Tyr Arg Lys Gly Ser Asn
              260                 265                 270

Met Glu Ala Thr Phe Asp Met Met Glu Gln Tyr Ser Phe Leu Lys Phe
              275                 280                 285

Gly Glu Val Lys Pro Phe Met Ile Ser Glu Tyr Gly Ala Gln Met His
              290                 295                 300

Asp Tyr Phe Gly Ala Trp Ser Pro Tyr Arg Asp Trp Leu His Leu Lys
305                 310                 315                 320

Ser Val Asn Ser Met Met Leu Gln Phe Met Glu Arg Pro His Ile Ile
              325                 330                 335

Asn Lys Thr Ile Asn Phe Leu Pro Val Lys Ala Glu Trp Gly Thr Lys
              340                 345                 350

Gly Val Asn Asp Thr Tyr Asn His Arg Leu Met Arg Arg Glu Asn Glu
              355                 360                 365

Pro Glu Ser Tyr Thr Gly Gln Trp Val Tyr Ser Glu Leu Val Lys Thr
              370                 375                 380

Tyr Gln Leu Trp Ser Glu Val Asn Gly Thr Arg Ile Asp Thr Tyr Ser
385                 390                 395                 400

Pro Asn Ala Asp Ile Leu Val Asp Gly Tyr Val Glu Gly Lys Asn Ala
              405                 410                 415

Tyr Leu Ile Leu Asn Asn Leu Asn Phe Glu Pro Ala Glu Ile Asp Leu
              420                 425                 430

Lys Ser His Gly Leu Ser Asp Asn Asn Ile Val Ser Ile Glu Ile Lys
              435                 440                 445

His Leu Tyr Leu Asp Gly Asp Ala Pro Val Leu Ser Thr Ser Val Glu
              450                 455                 460

Ser Ser Val Pro Glu Ser Leu Leu Leu Ala Ala Glu Gly Thr Met Ile
465                 470                 475                 480

Leu Glu Leu Thr Met Glu Glu Pro Ile Glu Pro Val Gln Ser Ser Ile
              485                 490                 495

Glu Lys Lys Tyr Tyr Ala Asp Thr Tyr Leu Gln Glu Ile Val Ser Glu
              500                 505                 510

Thr Pro Ile Thr Phe Asn Ile Asp Asn Val Glu Val Gly Glu Tyr Gly
              515                 520                 525

Glu Ala Val Leu Arg Val Gly Ile Gly Arg Gln His Gly Lys Ser Leu
530                 535                 540

Ala Pro Ser Val Leu Phe Asn Gly Gln Asn Ile His Val Pro Lys Asn
545                 550                 555                 560

Phe Arg Gly Asp Asp Gln Glu Asp Arg Ala Thr Phe Phe Gly Val Leu
              565                 570                 575

Glu Ile Pro Val Ser Tyr Asp Leu Ile Lys Gln Lys Asn Glu Val Gln

```
                    580             585             590
Ile Thr Phe Ser Asp Asp Gly Gly His Val Ser Ser Val Ala Met Gln
                595             600             605

Val Phe Asn Phe Ser Val Pro Ile Glu Arg
            610             615

<210> SEQ ID NO 37
<211> LENGTH: 688
<212> TYPE: PRT
<213> ORGANISM: Microbulbifer sp.

<400> SEQUENCE: 37

Val Thr Val Asn Ala Asn Ile Lys His Ser Val Lys Gly Ile Ser Asp
 1               5                  10                  15

Phe Gly Arg Asn Arg His Ile Thr Ala His Thr Thr Ile Tyr Glu Lys
                20                  25                  30

Asp Trp Glu Gly His Ala Asp Lys Leu Asn Tyr Leu Val Asn Thr Leu
            35                  40                  45

Asp Val Thr Leu Gly Arg Asp Asn Gly Thr Ala Thr Trp Lys Phe Gln
 50                  55                  60

Asp Thr Lys Glu Asp Pro Asn Arg Glu Asn Trp Pro Asp Leu Asp Tyr
 65                  70                  75                  80

Met Val Thr Arg Gly Lys Glu Leu Arg Glu Asn Tyr Glu Ala Asn Pro
                85                  90                  95

Phe Tyr Lys Arg Phe Ser Ala Asp Arg Thr Glu Leu Ile Ala Gly Thr
            100                 105                 110

Asn Pro His Pro Thr Tyr Pro Thr Leu Ser Trp Asn Ala Asn Gly Ser
        115                 120                 125

Thr Trp His Asp Trp Gln Pro Met His Ile Glu Thr Ser Ala Ala Trp
130                 135                 140

Met Gly Gln Tyr Leu Lys His Tyr Tyr Ala Asn Ser Ser Asn Gly Tyr
145                 150                 155                 160

Ile Gly Asp Pro Met Pro Lys Phe Trp Glu Val Ile Asn Glu Pro Asp
                165                 170                 175

Met Glu Met Lys Thr Gly Lys Phe Met Val Thr Asn Gln Glu Ala Ile
            180                 185                 190

Trp Glu Tyr His Asn Leu Val Ala Gln Glu Ile Arg Ser Lys Leu Gly
        195                 200                 205

Asn Glu Ala Pro Leu Ile Gly Gly Met Thr Trp Gly Gln His Asp Phe
210                 215                 220

Tyr Arg Arg Asp Gly Ile Ser Arg Tyr Ala Asp Asn Ala Tyr Asp Gln
225                 230                 235                 240

Trp Ile Val Ala Asp Pro Ala Glu Glu Ala Ala Glu Glu Phe
                245                 250                 255

Phe Arg Gln Ala Met Ala Thr Thr Val Asp Asp Thr Arg Asp Gln Asn
            260                 265                 270

Trp Tyr Gln Trp Asp Val Met Trp Lys Gly Phe Met Asp Ala Ala Gly
        275                 280                 285

His Asn Met Asp Phe Tyr Ser Val His Val Tyr Asp Trp Pro Gly Val
290                 295                 300

Asn Ser Asp Ala Lys Ser Thr Leu Arg Arg Asn Gly His Leu Pro Ala
305                 310                 315                 320

Met Leu Asp Met Ile Glu Trp Tyr Asp Val Tyr Gln Asn Gly Gln Ala
                325                 330                 335
```

```
Asn Arg Lys Pro Ile Val Ile Ser Glu Tyr Gly Ala Val Gln Gly Gly
                340                 345                 350

Trp Asn Thr Leu Ala His Gln Pro Arg Phe Glu Ser Glu Val Leu Lys
            355                 360                 365

Ser Phe Asn Ala Met Leu Met Gln Ile Leu Glu Arg Pro Asp Tyr Val
    370                 375                 380

Ile Lys Ser Met Pro Phe Thr Pro Ala Lys Pro Leu Trp Gly Tyr Tyr
385                 390                 395                 400

Pro Gly Gly Cys Gly Tyr Glu Glu Val Arg Asn Cys Thr Ala Pro Tyr
                405                 410                 415

His Tyr Ser Leu Leu Ile Glu Pro Val Leu Asn Ser Asp Asn Trp Gln
            420                 425                 430

Trp Ser Asp Tyr Ile Lys Phe Tyr Glu Leu Trp Ala Asp Ile Asp Gly
    435                 440                 445

Thr Arg Val Asp Ser Val Ser Ser Asp Pro Asp Val Gln Val Gln Ser
450                 455                 460

Tyr Val Asn Asn Asn Glu Leu Phe Ile Ile Asn Asn Leu Glu Thr
465                 470                 475                 480

Val Asp Thr Thr Ile Asp Leu Thr Val Ala Gly Leu Asn Asn Ala Gln
                485                 490                 495

Leu Gln Asn Val Glu Leu Arg Asn Met His Phe Asp Asn Asn Phe Asp
            500                 505                 510

Thr Gln Leu Glu Arg His His Met Lys Gln Met Pro Thr Lys Val Thr
    515                 520                 525

Leu Ala Ala Asp Ala Thr Leu Val Leu Arg Tyr Thr Leu Asn Ser Thr
530                 535                 540

Ile Ala Ile Asn Gln Ser Val Asp Glu Lys Lys Tyr Phe Gly Asn Ser
545                 550                 555                 560

Val Ser Gly Gly Ser Val Pro His Arg Ile Ser Val Ala Gly Gly Ala
                565                 570                 575

Lys Asn Leu Gln Val Asn Asn Val Ser Val Pro Ser Gly Tyr Ala Glu
            580                 585                 590

Ser Gln Leu Arg Leu Thr Val Ala Leu Tyr Pro Ser Gln Asp Asp Thr
    595                 600                 605

Pro Asp Ser Leu Leu Gln Ile Asp Thr Leu Thr Ile Asn Gly His Thr
610                 615                 620

Ile Glu Thr Pro Ile Asp Trp Arg Gly Arg Lys Glu Asn Ser Val Glu
625                 630                 635                 640

Arg Tyr Phe Asn Thr Leu Glu Ile Pro Val Pro Val Asp Val Leu Gln
                645                 650                 655

Lys Asn Asn Thr Ile Ser Val Asp Phe Arg His Asn Gly Glu Leu Thr
            660                 665                 670

Val Ala Asn Leu Val Ile Lys Glu Tyr Thr Thr Thr Pro Val Arg His
    675                 680                 685

<210> SEQ ID NO 38
<211> LENGTH: 684
<212> TYPE: PRT
<213> ORGANISM: Saccharophagus degradans

<400> SEQUENCE: 38

Val Ser Val Asn Ala Asn Phe Lys Arg Ser Val Asn Gly Val Phe Asp
 1               5                  10                  15

Phe Gly Arg Arg Arg His Met Thr Ala His Thr Ala Ile His Glu Pro
            20                  25                  30
```

```
Asp Trp Val Gly His Thr Asp Lys Leu Asn Tyr Leu Phe Asn Thr Leu
         35                  40                  45
Asp Val Tyr Met Gly Arg Asp Asn Gly Ser Ala Thr Trp Lys Phe Asn
 50                  55                  60
Asp Thr Thr Glu Asp Pro Asn Lys Pro Asn Trp Pro Asn Met Asp Tyr
 65                  70                  75                  80
Met Val Glu Arg Gly Lys Gly Leu Arg Glu Ala His Asp Gln Asn Pro
                 85                  90                  95
Leu Phe Lys Arg Phe Ser Ala Glu Lys Gln Leu Leu Ile Ala Gly Thr
                100                 105                 110
Asn Pro His Ala Leu Tyr Pro Thr Leu Ser Trp Phe Pro Asn Ala Phe
                115                 120                 125
Thr Trp Ser Gly Trp Gln Pro Lys Asn Ile Glu Thr Ser Ala Ala Trp
        130                 135                 140
Val Gly Gln Tyr Met Glu His Tyr Phe Ala Asn Ala Ser Asn Gly Tyr
145                 150                 155                 160
Val Gly Glu Gln Leu Pro Glu Tyr Trp Glu Val Asn Glu Pro Asp
                165                 170                 175
Met Lys Met Lys Thr Gly Gln Phe Met Val Thr Asn Gln Glu Ala Ile
                180                 185                 190
Trp Glu Tyr His Asn Leu Val Ala Gln Glu Ile Arg Asp His Leu Gly
                195                 200                 205
Ala Glu Ala Pro Pro Ile Gly Gly Met Thr Trp Gly Gln His Asp Phe
        210                 215                 220
Tyr Arg Arg Asp Gly Ile Ser Arg Phe Ala Asp Ser Tyr Asp Gln
225                 230                 235                 240
Trp Ile Thr Asn Asp Asp Gln Val Leu Gln Ala Glu Ala Arg Ala Phe
                245                 250                 255
Tyr Arg Asn Ala Met Ala Thr Thr Val Asp Asp Thr Arg Asp Gln Asp
                260                 265                 270
Trp Tyr Gln Trp Asp Val Met Trp Lys Gly Phe Met Asp Ala Ala Gly
        275                 280                 285
Asp Asn Met Asp Phe Tyr Ser Val His Ile Tyr Asp Trp Pro Gly Glu
        290                 295                 300
Asn Val Gly Asp Thr Thr Val Val Arg Arg Gly Gly His Thr Ser Ala
305                 310                 315                 320
Met Leu Glu Met Met Glu Trp Tyr Asp Val Lys Arg Asn Gly Phe Asn
                325                 330                 335
Asn Arg Lys Pro Ile Val Leu Ser Glu Tyr Gly Ser Val Asn Gly Ala
                340                 345                 350
Trp Asp Asn Arg Ala His Glu Glu Arg Tyr Asp Ile Ala Ser Ile Lys
        355                 360                 365
Ala Phe Asn Gly Met Leu Met Gln Phe Leu Glu Arg Pro Asp Tyr Val
        370                 375                 380
Ile Lys Ser Leu Pro Phe Thr Pro Ala Lys Pro Leu Trp Gly Tyr Leu
385                 390                 395                 400
Pro Gly Gly Cys Gly Tyr Asp Asp Ala Val Ala Cys Thr Thr Arg Tyr
                405                 410                 415
His Tyr Ala Met Leu Ile Glu Asp Glu Leu Asn Ser Gly Asn Trp Glu
                420                 425                 430
Trp Ser Ser Tyr Ile Lys Phe Tyr Glu Leu Trp Ala Asp Ile Asp Gly
        435                 440                 445
```

```
Thr Arg Val Asp Ser Lys Ser Ser Asp Val Asp Val Gln Val Asp Ser
    450                 455                 460
Tyr Val Lys Gly Asn Glu Leu Phe Val Ile Leu Asn Asn Leu Glu Ala
465                 470                 475                 480
Ala Asp Thr Thr Val Asn Leu Asp Val Ser Gly Ile Ala Ser Val Gln
            485                 490                 495
Asn Val Glu Leu Arg Asn Met His Phe Asp Ile Gln Glu Thr His Leu
        500                 505                 510
Asp Arg His His Met Ser Ala Ala Pro Lys Thr Val Thr Leu Ala Ala
    515                 520                 525
Asp Ala Thr Val Val Leu Arg Tyr Thr Leu Ala Ser Ser Val Ala Val
530                 535                 540
Asn Asn Thr Val Val Glu Lys Lys Tyr Phe Gly Ser Val Ser Gly
545                 550                 555                 560
Gly Ile Glu Pro His Arg Ile Ser Val Ala Gly Ala Lys Thr Leu
            565                 570                 575
Tyr Ile Asn Asn Val Ser Val Pro Ser Gly Tyr Ser Glu Ala Ile Leu
        580                 585                 590
Arg Leu Thr Val Ser Leu Tyr Pro Asp Glu Asp Lys Val Gly Gly
    595                 600                 605
His Leu Ser Leu Asp Ser Ile Thr Val Asn Gly Thr Ala Ile Glu Ala
    610                 615                 620
Pro Ile Asp Trp Lys Gly Pro Lys Ala Asn Arg Ala Glu Arg Phe Phe
625                 630                 635                 640
Gly Val Leu Asp Ile Pro Val Pro Val Glu Leu Leu Gln Ser Thr Asn
            645                 650                 655
Thr Ile Ala Val Asp Phe Arg His Asn Gly Glu Leu Thr Val Ala Asn
        660                 665                 670
Leu Ile Val Ser Glu Phe Thr Ser Glu Pro Asn Arg
    675                 680

<210> SEQ ID NO 39
<211> LENGTH: 677
<212> TYPE: PRT
<213> ORGANISM: Microscilla sp.

<400> SEQUENCE: 39

Val Gln Val Asp Val Asn Leu Asn Val Lys His Ser Val Gly Gly Val
1               5                   10                  15
Ser Asp Phe Gly Arg Asp Arg His Met Thr Val His Ser Ser Leu Thr
            20                  25                  30
Glu Pro Asp Trp Gln Gly Glu Ala Lys Met Asp Tyr Leu Leu Thr
        35                  40                  45
Asp Leu Asp Thr Tyr Leu Gly Arg Asp Asn Gly Ser Ala Thr Trp Lys
    50                  55                  60
Phe Ala Ser Thr Pro Gln Asp Pro Asn Asn Pro His His Pro Ser Val
65                  70                  75                  80
Asp Ser Met Gln Ala Phe Gly Asp Trp Leu Lys Gly Glu Tyr Glu Ser
            85                  90                  95
Leu Thr Asn Arg His Gln Tyr Glu Ser Arg Ala Ser Gly Met Ile Met
        100                 105                 110
Gly Thr Asn Ala His Pro Thr Tyr Pro Thr Leu Ser Trp Tyr Ala Asn
    115                 120                 125
Gly Ser Thr Trp Thr Asp Pro Gln Trp Gln Pro Lys Asp Val Gln Thr
130                 135                 140
```

```
Ser Ala Asp Trp Val Thr Glu Tyr Leu Asp Lys Phe Phe Ala His Ser
145                 150                 155                 160

Pro Ser Val Asp Gly Glu Pro Leu Pro Lys Tyr Trp Glu Val Val Asn
            165                 170                 175

Glu Pro Asp Met Glu Tyr Met Thr Gly Lys Phe Met Val Thr Ser Gln
            180                 185                 190

Glu Lys Ile Trp Glu Tyr His Asn Leu Val Ala Gln Gly Val Lys Glu
            195                 200                 205

Arg Leu Gly Thr Asp Ala Pro Leu Ile Gly Gly Met Thr Trp Gly Leu
            210                 215                 220

His Asp Leu Phe Ala Gly Asp Gly Leu Ser Arg Tyr Gln Pro Asp Tyr
225                 230                 235                 240

Leu Asp Gln Tyr Leu Asp Ala Glu Thr Ala Glu Phe Tyr Arg Asn Ala
                245                 250                 255

Ala Ala Thr Gln Trp Pro Gly Asn Gln Asn Gln Pro Trp Tyr Gln Trp
            260                 265                 270

Asp Val Gln Trp Lys Gly Phe Ile Asp Ala Ala Gly Ala Asn Met Asp
            275                 280                 285

Phe Tyr Ser Val His Phe Tyr Asp Trp Pro Thr Tyr Asn Ala Ser Gly
            290                 295                 300

Gly Ala Val Arg Ser Gly Gly His Val Glu Ala Thr Leu Asp Met Leu
305                 310                 315                 320

Glu Trp Tyr Asp Val Gln Lys Phe Gly Val Ser Asn Arg Lys Pro Val
                325                 330                 335

Val Ile Ser Glu Tyr Gly Ala Val Gln Gly Ser Trp Thr Tyr Leu Pro
            340                 345                 350

His Asp Asn Arg Tyr Asp Trp Glu Cys Ile Lys Pro Phe Asn Ser Met
            355                 360                 365

Leu Met Gln Phe Leu Glu Arg Pro Asp Tyr Ile Ile Tyr Thr Leu Pro
370                 375                 380

Phe Thr Pro Ile Lys Ala Gln Trp Gly Asp Val Asp Gln Asn Gly Asp
385                 390                 395                 400

Gly Thr Pro Glu Tyr Val Tyr Gln Tyr Lys Leu Met Arg Asp Asp
                405                 410                 415

His Asp Gly Asn Trp Glu Trp Ser Asp Tyr Ile Lys Phe Tyr Glu Leu
            420                 425                 430

Trp Ser Glu Val Lys Gly Thr Arg Ile Asp Thr Lys Ser Thr Asp Pro
            435                 440                 445

Asp Ile Gln Ile Asp Ala Tyr Val Asp Gly Lys Asp Val Phe Leu Ile
            450                 455                 460

Leu Asn Asn Leu Glu Asn Gln Ala Thr Thr Ile His Leu Asn Leu Tyr
465                 470                 475                 480

Glu Asp Phe Gly Asn Asn Val Gln Asn Val Asn Ile Lys His Leu His
            485                 490                 495

Leu Thr Gly Thr Ser Thr Val Thr Leu Asp Asn Asn Asp His Ala Thr
            500                 505                 510

Ala Pro Glu Ser Val Gln Leu Ala Gly Asp Gly Thr Met Val Ile Lys
            515                 520                 525

Tyr Thr Tyr Gly Ser Ala Val Asn Ile Asn His Asn Ser Ile Glu Lys
            530                 535                 540

Lys Phe Tyr Gly Glu Ser Leu Ser Gly Thr Val Pro Asn Arg Val Ser
545                 550                 555                 560
```

```
Ile Pro Asn Gly Glu Met Thr Met Gln Ile Asn Gly Val Asp Val Pro
            565                 570                 575

Ala Asp Ala Ser Lys Ala Glu Ala Met Leu Arg Ile Thr Cys Ala Leu
        580                 585                 590

Tyr Asn Asp Asp Asn Gln Val Gly His Leu Ser Ile Asp Lys Leu
        595                 600                 605

Thr Val Asn Gly Thr Glu Ile Glu Thr Pro Leu Asp Trp Arg Gly Thr
        610                 615                 620

Asn Gln Val Arg Asn Arg Tyr Phe Ser Thr Leu Glu Ile Pro Val Pro
625                 630                 635                 640

Val Gly Leu Leu Gln Thr Asn Asn Thr Phe Thr Val Asp Phe His His
                645                 650                 655

Val Gly Glu Val Ala Val Val Asn Leu Gln Thr Trp Glu Phe Ser Lys
        660                 665                 670

Val Pro Gly Arg Ser
        675

<210> SEQ ID NO 40
<211> LENGTH: 479
<212> TYPE: PRT
<213> ORGANISM: Pseudoalteromonas atlantica

<400> SEQUENCE: 40

Val Val Val Asn Leu Asn Val Lys His Ser Val Glu Gly Lys Ser Glu
1               5                   10                  15

Phe Glu Arg Lys Asn His Ile Lys Leu His Ser Thr Leu Asn Asp Asn
            20                  25                  30

Asp Trp Gln Gly Glu Asp Lys Leu Lys Tyr Met Met Glu Glu Leu
        35                  40                  45

Asp Val Tyr Phe Gly Arg Asp Asn Gly Thr Val Trp Asn Phe Asn
    50                  55                  60

Gln Ala Ile Glu Asp Pro Ala Asn Ile Gly Tyr Ala Asp Pro Gln Asn
65                  70                  75                  80

Ile Ile Ala Arg Gly Gln Ala Gln Arg Glu Thr Asn Trp Gly Gln Asn
                85                  90                  95

Lys Ser Ala Leu His Gln Tyr Asp Gly Arg Gly Asp Leu Met Ile Gly
            100                 105                 110

Gly Gln Pro Arg Ala His Tyr Leu Gly Asn Thr Ser Pro Cys Cys Gly
        115                 120                 125

Gly Ser Ala Trp Gln Ala Lys Gly Gly Asp Ala Val Gly Asp Phe Leu
    130                 135                 140

Gly Gln Tyr Val Asn Glu Phe Phe Arg Ser Ala Gly Asp Pro Val Thr
145                 150                 155                 160

Lys Gly His Leu Ala Pro Val Tyr Phe Glu Val Leu Asn Glu Pro Leu
                165                 170                 175

Tyr Gln Val Thr Asp Ala Pro His Glu Leu Gly Leu Glu Gln Pro Ile
            180                 185                 190

Pro Pro Ile Asp Ile Phe Thr Phe His Asn Asp Val Ala Asp Ala Phe
        195                 200                 205

Arg Gln His Asn Thr His Ile Lys Ile Gly Gly Phe Thr Val Ala Phe
    210                 215                 220

Pro Ile Phe Glu Gln Arg Glu Phe Ala Arg Trp Glu Glu Arg Met Lys
225                 230                 235                 240

Leu Phe Ile Asp Thr Ser Gly Ser His Met Asp Val Tyr Ser Thr His
                245                 250                 255
```

```
Phe Tyr Asp Leu Glu Asp Asp Asn Arg Phe Lys Gly Ser Arg Leu Glu
            260                 265                 270

Ala Thr Leu Asp Met Ile Asp Gln Tyr Ser Leu Leu Ala Leu Gly Glu
        275                 280                 285

Thr Lys Pro His Val Ile Ser Glu Tyr Gly Arg Asn Arg Pro Met
    290                 295                 300

Glu Asn Ala Pro Trp Ser Ala Leu Arg Asp Trp Trp Phe Leu Lys Thr
305                 310                 315                 320

Ala Ser Pro Met Leu Met Gln Phe Leu Ser Arg Pro Asp Ser Val Leu
                325                 330                 335

Thr Ser Ile Pro Phe Val Pro Ile Lys Ala Leu Trp Gly Thr Ala Ala
            340                 345                 350

Asp Gly Thr Pro Tyr Asn Trp Arg Leu Leu Arg Gln Gln Lys Glu Ala
        355                 360                 365

Pro Asn Glu Thr Gly Glu Asn Trp Val Phe Thr Glu Met Val Lys Phe
    370                 375                 380

Tyr Gln Leu Trp Ser Asp Val Lys Gly Thr Arg Val Asp Thr Phe Ser
385                 390                 395                 400

Thr Asn Ser Asp Phe Leu Ile Asp Ser Tyr Val Gln Asn Asp Lys Ala
                405                 410                 415

Tyr Val Leu Ile Ser Asn Leu Thr Glu Gln Ala Glu Lys Ile Val Val
            420                 425                 430

His Lys Tyr Gly Ala Pro Ala Ser Ser Gln Pro Thr Thr Arg Ile Lys
        435                 440                 445

His Leu Tyr Leu Lys Gly Ala Ala Pro Arg Leu Met Lys Gln Val Met
    450                 455                 460

Arg Gln Ile Ser Lys Lys Ser Arg Leu Leu Lys Arg Leu Trp
465                 470                 475

<210> SEQ ID NO 41
<211> LENGTH: 623
<212> TYPE: PRT
<213> ORGANISM: Rhodopirellula baltica

<400> SEQUENCE: 41

Leu Pro Val Lys Phe Asp Asp Ile Pro Tyr Arg Thr Leu Gly Ala Asp
1               5                   10                  15

Arg Pro Arg Val Pro Val Asn Val Arg Val Asp Leu Gln His Glu Leu
            20                  25                  30

Ser Ile Ala Gly His Val Asp Leu Glu Arg Gln Lys Phe Phe Arg Tyr
        35                  40                  45

Tyr Ala Ala Pro Gly Thr Ser Asp Pro Ser Phe Glu Arg Trp Ala Ser
    50                  55                  60

Glu Arg Asn Phe Ser Pro Gly Arg Gln Ile Phe Lys Leu Asp Pro Ala
65                  70                  75                  80

Leu Val Val Gly Tyr Gly Pro Gly Glu Lys Leu Lys Glu Asp Pro Asn
                85                  90                  95

Asn Lys Gly Ala Ala Asp Leu Thr Phe Phe Asp Arg His Asp Ser Ser
            100                 105                 110

Pro Pro Lys Thr Ile Pro Glu Phe Glu Ala Thr Asp Tyr Ala Met Cys
        115                 120                 125

Leu Asn Asp Tyr Pro Glu Phe Met Ser Val Glu His Val Gly Arg Gly
    130                 135                 140

Thr Pro Leu Ile Glu His Phe Gly Asp Ala Ala Asn Leu Ala Ala Ala
```

-continued

```
                145                 150                 155                 160
        His Ile Ala Asp Gln Gln Arg Asp Gly Gly Arg Thr Ala Lys Trp Trp
                        165                 170                 175
        Glu Val Lys Asn Glu Ser Thr Ile Lys Ala Glu Trp Asp Tyr His Tyr
                        180                 185                 190
        Gln Lys Glu His Asp Ser Trp Ala Leu Leu Ala Glu Phe His Asn Ala
                        195                 200                 205
        Val Ala Glu Ala Val His Ala Lys Thr Pro Ser Val Asn Val Gly Gly
        210                 215                 220
        Pro Thr Ser Ala Trp Met Gln Leu His Val Asn Gln Phe Gly Leu Tyr
        225                 230                 235                 240
        Arg Asp Gln Thr Arg Phe Met Asp Leu Thr Arg Asp His Leu Asp Phe
                        245                 250                 255
        Tyr Ser Arg His Phe Tyr Glu Asp Met Gly Ser Leu Gly Ala Trp Glu
                        260                 265                 270
        Arg Arg Asp Lys Gly Tyr Ser Gly Tyr Leu Leu Gly Arg Leu Glu Ala
                        275                 280                 285
        Thr Leu Asp Met Leu Gln Ala His Met Glu Glu Thr Asp Asn Val Lys
                        290                 295                 300
        Pro Ile Leu Ile Thr Glu Cys Gly Ser Leu Gln Ala Gly Arg Gly Ala
        305                 310                 315                 320
        Ala Asp Tyr Trp Leu Arg Leu Arg Ser Phe Ser Ala Phe Leu His Lys
                        325                 330                 335
        Leu Met Ser Arg Pro His Gln Ile Asp Leu Ser Val Pro Phe Val Phe
                        340                 345                 350
        Thr Asn Met His Trp Asn Pro Thr Ser Gly Asn Val Ala Phe Val Pro
                        355                 360                 365
        Thr Glu Gly Ala Ser Ala Arg Gly Pro Leu Ala Asp Phe Gln Pro Thr
                        370                 375                 380
        Pro Val Ala Asp Phe Phe Glu Leu Trp Arg Asp Phe Asp Gly Arg Arg
        385                 390                 395                 400
        Leu Pro Val Ala Thr Asn Asp Leu Ala Glu Val Gly Leu Asn Ala Thr
                        405                 410                 415
        Ala Val Tyr Gln Gly Asn Arg Leu Gln Ile Ala Leu Thr Asn Met Thr
                        420                 425                 430
        Ser His Gln Leu Ser Val His Leu Ser Asp Ile Ala Gly Asp Ala Leu
                        435                 440                 445
        His Ala Ser Ser Ile Gln Gln Arg Arg Leu Arg Tyr Asn Asp Gly Glu
        450                 455                 460
        Val Ile Tyr Glu Asp Ala Ile Ser Leu Ser Asp Ser Asn Ala Ile Glu
        465                 470                 475                 480
        Val Asp Ala Glu Glu Thr Thr Val Leu Thr Phe Thr Phe Asp Gln Thr
                        485                 490                 495
        Ile Gln Pro Asn Arg Thr Leu Leu Arg Gln Phe Ala Tyr Ala Ala Gly
                        500                 505                 510
        Thr Ala Val Pro Ala Asp Gln Thr Gln Thr Phe Gln Ile Asp Ile Asp
                        515                 520                 525
        Asp Ala Ser Asp Ile Glu Ser Ala Glu Leu Val Val Gly Val His Arg
        530                 535                 540
        Ile Lys Gly Leu Glu Gln Ala Val Ser Gly Thr Phe Asn Gly His Arg
        545                 550                 555                 560
        Phe Glu Ser His Pro Glu Trp Thr His Gln Phe Asp Gln Leu Leu Ala
                        565                 570                 575
```

```
Pro Leu Glu Ile Pro Ile Ser Lys Asp Trp Leu Gln Asn Asn Asn Gln
            580                 585                 590

Ile Gln Ile Glu Pro Gln Pro Gly Leu Thr Ile Thr Ser Val His Leu
        595                 600                 605

Ile Cys Asp Ser Ile Ser Glu Ala Leu Asp Ser Lys His Ser Gln
    610                 615                 620

<210> SEQ ID NO 42
<211> LENGTH: 140
<212> TYPE: PRT
<213> ORGANISM: Saccharophagus degradans

<400> SEQUENCE: 42

Gly Ala Ala Asp Tyr Val Ile Glu Ala Glu Asn Phe Val Ala Gln Gly
1               5                   10                  15

Gly Thr Tyr Val Asp Gly Gln Pro Asn Lys Val Ser Val Tyr Ser Val
            20                  25                  30

Asn Gly Ala Thr Ala Ile Asn Tyr Val Asn Arg Ala Asp Tyr Thr Asp
        35                  40                  45

Tyr Gln Ile Asn Val Ala Thr His Gly Tyr Tyr Asn Val Gln Tyr Ala
    50                  55                  60

Ile Gly Thr Ser Val Ala Ser Gly Ala Ala Ile Glu Leu Leu Val Gln
65                  70                  75                  80

Asn Gly Ser Ser Trp Glu Ser Gln Gly Gln Thr Asn Val Pro Val Gly
                85                  90                  95

His Trp Asp Ser Phe Gln Pro Leu Asn Ala Ser His Glu Val Ile Leu
            100                 105                 110

Pro Ala Gly Thr Val Asn Leu Arg Val Tyr Gly Ala Gly Ser Asn Asp
        115                 120                 125

Trp Gln Trp Asn Leu Asp Ser Ile Ser Leu Thr Leu
    130                 135                 140

<210> SEQ ID NO 43
<211> LENGTH: 141
<212> TYPE: PRT
<213> ORGANISM: Saccharophagus degradans

<400> SEQUENCE: 43

Pro Ser Pro Gln Leu Val Lys Thr Glu Ala Glu Ala Phe Asn Ala Gln
1               5                   10                  15

Ser Gly Thr Phe Ala Asp Gly Gln Pro Thr Pro Val Ser Ile Tyr Thr
            20                  25                  30

Val Asn Gly Lys Thr Ala Ile Asn Phe Val Asn Lys Gly Asp Ala Val
        35                  40                  45

Glu Tyr Asn Leu Val Ala Pro Ala Ala Gly Ser Tyr Ala Leu Lys Tyr
    50                  55                  60

Ser Ile Gly Thr Ser Val Ala Ser Gly Ser Glu Val Glu Phe Phe Val
65                  70                  75                  80

Leu Lys Asn Asn Val Trp Val Ser Gln Gly Lys Thr Pro Val Pro Ala
                85                  90                  95

Val Gly Trp Asp Asn Phe Thr Ser Val Ala Ser Ala Gln Thr Val Glu
            100                 105                 110

Leu Ala Ala Gly Ser Asn Lys Val Lys Leu Val Gly Ala Gly Thr Asn
        115                 120                 125

Asp Trp Gln Trp Asn Leu Asp Phe Phe Glu Leu Thr Leu
    130                 135                 140
```

<210> SEQ ID NO 44
<211> LENGTH: 139
<212> TYPE: PRT
<213> ORGANISM: Saccharophagus degradans

<400> SEQUENCE: 44

```
Pro Ser Thr Ala Ser Ile Ala Val Glu Ala Glu Asn Phe Asn Ala Val
 1               5                  10                  15

Gly Gly Thr Phe Ser Asp Gly Gln Ala Gln Pro Val Ser Val Tyr Thr
            20                  25                  30

Val Asn Gly Asn Thr Ala Ile Asn Tyr Val Asn Gln Gly Asp Tyr Ala
        35                  40                  45

Asp Tyr Thr Ile Ala Val Ala Gln Ala Gly Asn Tyr Thr Ile Ser Tyr
    50                  55                  60

Gln Ala Gly Ser Gly Val Thr Gly Gly Ser Ile Glu Phe Leu Val Asn
65                  70                  75                  80

Glu Asn Gly Ser Trp Ala Ser Lys Thr Val Thr Ala Val Pro Asn Gln
                85                  90                  95

Gly Trp Asp Asn Phe Gln Pro Leu Asn Gly Gly Ser Val Tyr Leu Ser
            100                 105                 110

Ala Gly Thr His Gln Val Arg Leu His Gly Ala Gly Ser Asn Asn Trp
        115                 120                 125

Gln Trp Asn Leu Asp Lys Phe Thr Leu Ser Asn
    130                 135
```

<210> SEQ ID NO 45
<211> LENGTH: 135
<212> TYPE: PRT
<213> ORGANISM: Saccharophagus degradans

<400> SEQUENCE: 45

```
Pro Val Ser Gly Ser Phe Lys Leu Glu Ala Glu His Phe Gln Lys Val
 1               5                  10                  15

Gly Gly Glu Val Gln Ile Tyr Ser Leu Ser Pro Gly Asn Ala Val Asn
            20                  25                  30

Tyr Phe Asn Ser Gly Asp Tyr Leu Glu Phe Tyr Val Asp Leu Asp Ala
        35                  40                  45

Gly Gly Leu Tyr Glu Ala Ser Phe Arg Val Gly Thr Gly Val Ala Ser
    50                  55                  60

Asp Val Ala Val Gly Leu Met Val Thr Asp His Lys Gly Asp Leu Thr
65                  70                  75                  80

Leu Lys Ser Val Thr Pro Val Thr Asp Gln Gly Gly Trp Asp Ala Phe
                85                  90                  95

Tyr Asn Leu Thr Ala Gln Ser Gln Leu Asn Ile Tyr Ser Gly Ile Asn
            100                 105                 110

Thr Ile Arg Ile Thr Gly Ala Gly Ser Ala Asp Phe Gln Phe Asn Ile
        115                 120                 125

Asp Ser Ile Thr Leu Thr Arg
    130                 135
```

<210> SEQ ID NO 46
<211> LENGTH: 124
<212> TYPE: PRT
<213> ORGANISM: Saccharophagus degradans

<400> SEQUENCE: 46

```
Gly Lys Glu Gly Ser Ala Val Ala Gly Asp Thr Phe Thr Gly Phe Asn
 1               5                  10                  15

Pro Ser Gly Ala Asn Asn Ile Asn Tyr Asn Thr Leu Gly Asp Trp Ala
            20                  25                  30

Asp Tyr Thr Val Asn Phe Pro Ala Ala Gly Asn Tyr Thr Val Asn Leu
        35                  40                  45

Ile Ala Ala Ser Pro Val Thr Ser Gly Leu Gly Ala Asp Ile Leu Val
50                  55                  60

Asp Ser Ser Tyr Ala Gly Thr Ile Pro Val Ser Ser Thr Gly Ala Trp
65                  70                  75                  80

Glu Ile Tyr Asn Thr Phe Ser Leu Pro Ser Ser Ile Tyr Ile Ala Ser
                85                  90                  95

Ala Gly Asn His Thr Ile Arg Val Gln Ser Ser Gly Gly Ser Ala Trp
            100                 105                 110

Gln Trp Asn Gly Asp Glu Leu Arg Phe Thr Gln Thr
            115                 120
```

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
aactgcagat ccatgaaaac cacaaatgc                                    29

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ccatcgatct tatctaggtt ccactgcca                                    29

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ccatcgatac ctgtggcaga gaagttg                                      27

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ccatcgatgt agaatcgcac ccagtcaat                                    29

<210> SEQ ID NO 51
<211> LENGTH: 29

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cttggcgcgc cggcgcgacg aacaaggta                                       29

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccatcgaatg tactgggtgg attggtg                                         27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cttggcgcgc cgagtcgctt ttatcat                                         27

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccatcgattc tatttggctc agaagt                                          26

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccatcgatgc gccaaggctg atgctgt                                         27

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctctcatcaa ccgtggcgag gtcggcgcaa actgtca                              37

<210> SEQ ID NO 57
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 57
acacattgcg atagtcacgc                                                      20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccgctgcgct gtgagtatc                                                       19

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctctcatcaa ccgtgggctt atttacgcag tgttagg                                   37

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctctttcgcg ttagcatcta a                                                    21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagagccttc tttacctgtg                                                      20

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgatgatggt tgagatgtgt ttatgtctga tggctaaacg a                              41

<210> SEQ ID NO 63
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (4)
<223> OTHER INFORMATION: Any amino acid
<220> FEATURE:
<221> NAME/KEY: MOD_RES
<222> LOCATION: (6)
<223> OTHER INFORMATION: Any amino acid
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (10)
<223> OTHER INFORMATION: Any amino acid
<220> FEATURE:
<221> NAME/KEY: MOD_RES
<222> LOCATION: (12)
<223> OTHER INFORMATION: Any amino acid
<220> FEATURE:
<221> NAME/KEY: MOD_RES
<222> LOCATION: (14)
<223> OTHER INFORMATION: Any amino acid
<220> FEATURE:
<221> NAME/KEY: MOD_RES
<222> LOCATION: (16)
<223> OTHER INFORMATION: Any amino acid
<220> FEATURE:
<221> NAME/KEY: MOD_RES
<222> LOCATION: (18)
<223> OTHER INFORMATION: Any amino acid
<220> FEATURE:
<221> NAME/KEY: MOD_RES
<222> LOCATION: (20)
<223> OTHER INFORMATION: Any amino acid
<220> FEATURE:
<221> NAME/KEY: MOD_RES
<222> LOCATION: (22)
<223> OTHER INFORMATION: Any amino acid
<220> FEATURE:
<221> NAME/KEY: MOD_RES
<222> LOCATION: (24)
<223> OTHER INFORMATION: Any amino acid
<220> FEATURE:
<221> NAME/KEY: MOD_RES
<222> LOCATION: (26)
<223> OTHER INFORMATION: Any amino acid
<220> FEATURE:
<221> NAME/KEY: MOD_RES
<222> LOCATION: (28)
<223> OTHER INFORMATION: Any amino acid
<220> FEATURE:
<221> NAME/KEY: MOD_RES
<222> LOCATION: (30)
<223> OTHER INFORMATION: Any amino acid
<220> FEATURE:
<221> NAME/KEY: MOD_RES
<222> LOCATION: (32)
<223> OTHER INFORMATION: Any amino acid
<220> FEATURE:
<221> NAME/KEY: MOD_RES
<222> LOCATION: (34)
<223> OTHER INFORMATION: Any amino acid

<400> SEQUENCE: 63

Pro Xaa Pro Xaa Pro Xaa Pro Xaa Pro Xaa Pro Xaa Pro Xaa Pro Xaa
 1               5                  10                  15

Pro Xaa Pro Xaa Pro Xaa Pro Xaa Pro Xaa Pro Xaa Pro Xaa Pro Xaa
            20                  25                  30
```

```
Pro Xaa

<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Pro Glu Pro Glu Pro Glu Pro Glu Pro Glu Pro Glu Pro Glu Pro
 1               5                  10                  15

Glu Pro Glu Pro Glu Pro Glu Pro Glu Pro Glu Pro Glu Pro Glu Pro
            20                  25                  30

Glu Pro

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 65

His His His His His His
 1               5
```